United States Patent
Biermann et al.

(10) Patent No.: US 11,352,604 B2
(45) Date of Patent: Jun. 7, 2022

(54) METHOD OF MAKING CARDIOMYOCYTES FROM HUMAN PLURIPOTENT CELLS

(71) Applicant: Wisconsin Alumni Research Foundation, Madison, WI (US)

(72) Inventors: Mitch James Biermann, Madison, WI (US); Timothy Joseph Kamp, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/721,076

(22) Filed: Sep. 29, 2017

(65) Prior Publication Data
US 2018/0094246 A1 Apr. 5, 2018

Related U.S. Application Data

(60) Provisional application No. 62/402,785, filed on Sep. 30, 2016.

(51) Int. Cl.
| | |
|---|---|
| *C12N 5/00* | (2006.01) |
| *C12N 5/077* | (2010.01) |
| *A61K 35/34* | (2015.01) |
| *C12N 5/0735* | (2010.01) |
| *C12N 5/074* | (2010.01) |

(52) U.S. Cl.
CPC ............ *C12N 5/0657* (2013.01); *A61K 35/34* (2013.01); *C12N 5/0606* (2013.01); *C12N 5/0696* (2013.01); *C12N 2501/056* (2013.01); *C12N 2501/33* (2013.01); *C12N 2501/415* (2013.01); *C12N 2501/50* (2013.01); *C12N 2501/727* (2013.01); *C12N 2506/02* (2013.01); *C12N 2506/45* (2013.01)

(58) Field of Classification Search
USPC ....................................................... 435/325
See application file for complete search history.

(56) References Cited

U.S. PATENT DOCUMENTS

| | | | | |
|---|---|---|---|---|
| 8,318,489 | B2 * | 11/2012 | Davidson ............. | G01N 33/502 435/377 |
| 9,238,795 | B2 * | 1/2016 | Sinha ................... | C12N 5/0661 |
| 2013/0189785 | A1 | 7/2013 | Palecek | |
| 2014/0134733 | A1 | 5/2014 | Wu | |
| 2016/0068814 | A1 | 3/2016 | Palecek et al. | |

FOREIGN PATENT DOCUMENTS

WO 2013/109763 A1 7/2013

OTHER PUBLICATIONS

Zhao ("Efficient differentiation of TBX18+/WT1+ epicardial-like cells from human pluripotent stem cells using small molecular compounds." Stem Cells Dev 2017;26(7):528-540.*
Witty "Generation of the epicardial lineage from human pluripotent stem cells." Nat Biotechnol. 2014;32(10):1026-1035.*
Iyer ("Robust derivation of epicardium and its differentiated smooth muscle cell progeny from human pluripotent stem cells." Development. 2015; 142(8): 1528-1541.*
Shenje (eLIFE, 2013, vol. 3, e02164).*
Francou (Biochimica et Biophysica ACTA—Molecular Cell Research, Apr. 2013, vol. 1833, No. 4, p. 795-798).*
Kwon (The Scientist, Sep. 2018, "Adult cardiac stem cells don't exist: Study").*
Kattman (Cell Stem Cell, 2011, vol. 8, p. 228-240).*
Lian (Nat. Protoc., 2013, vol. 8, p. 162-175).*
Tran (Protein Sci., 2017, vol. 26, p. 650-661).*
Gwak, Cell Res., 2012, vol. 22, p. 237-247.*
Lian (PNAS, 2012, E1848-E1857).*
Pavlovic (Cytotherapy, 2015, vol. 17, p. 1763-1776).*
Barry, et al. (2017). Species-specific developmental timing is maintained by pluripotent stem cells ex utero. Dev. Biol. 423, 101-110.
Bu, et al. (2009) Human ISL1 heart progenitors generate diverse multipotent cardiovascular cell lineages. Nature 460, 113-117.
Camus, et al. (2006). Absence of Nodal signaling promotes precocious neural differentiation in the mouse embryo. Dev. Biol. 295, 743-755.
Connell, et al. Therapeutic Transdifferentiation: A Novel Approach For Ischemic Syndromes, houstonmethodist.org/debakey-journal, MDCVJ | XI (3) 2015, pp. 176-180.
Cooke, et al., Innate immunity and epigenetic plasticity in cellular reprogramming, CurrOpin Genet Dev. Oct. 2014, pp. 89-91.
D'Amato, et al. (2016). Sequential Notch activation regulates ventricular chamber development Nat Cell Biol 18, 7-20.
Han, et al. (2010). Tbx3 improves the germ-line competency of induced pluripotent stem cells. Nature 463, 1096-1100.
Han, et al. (2016). Coordinating cardiomyocyte interactions to direct ventricular chamber morphogenesis Nature 534, 700-704.
Horn, et al. (2011). The Permeability Transition Pore Controls Cardiac Mitochondrial Maturation and Myocyte Differentiation. Dev. Cell 21, 469-478.
Huber, et al. (2013). Costimulation-Adhesion Blockade is Superior to Cyclosporine A and Prednisone Immunosuppressive Therapy for Preventing Rejection of Differentiated Human Embryonic Stem Cells Following Transplantation. Stem Cells Dayt. Ohio 31, 2354-2363.

(Continued)

*Primary Examiner* — Michael C Wilson
(74) *Attorney, Agent, or Firm* — McDonnell Boehnen Hulbert and Berghoff LLP

(57) ABSTRACT

An improvement to the GiWi protocol for differentiating human pluripotent cells to developmentally mature cardiomyocytes includes a step of activating innate immunity in mesoderm stage cells in the in vitro differentiation culture. When the mesoderm cells, which are precursors to cardiac progenitor cells, are primed by exposure to an activator of innate immunity, a population of cardiomyocytes is generated that is more developmentally mature than is generated in the GiWi protocol without the primed step. Also provided herein are in vitro ventricular conductive microtissues and isolated, in vitro populations of ventricular conduction system-like cells and methods for making the same.

10 Claims, 20 Drawing Sheets
(20 of 20 Drawing Sheet(s) Filed in Color)

Specification includes a Sequence Listing.

(56) References Cited

OTHER PUBLICATIONS

Jiang, et al. (2015). Network analysis of gene essentiality in functional genomics experiments. Genome Biol. 16, 239.

Kamakura, et al. (2013). Ultrastructural maturation of human-induced pluripotent stem cell-derived cardiomyocytes in a long-term culture. Circ. J. Off. J. Jpn. Circ. Soc. 77, 1307-1314.

Lang, et al. (2015). Arrhythmogenic Remodeling of β2 versus β1 Adrenergic Signaling in the Human Failing Heart. Circ. Arrhythm. Electrophysiol. CIRCEP.114.002065.

Lee, et al. Activation of Innate Immunity is Required for Efficient Nuclear Reprogramming. Cell 151, 547-558 (2012).

Lian, et al., Robust cardiomyocyte differentiation from human pluripotent stem cells via temporal modulation of canonical Wnt signaling, Proc. Nat. Acad. Sci. 109:27, E1848-E1857, published online May 29, 2012.

Maass, et al. (2015). Isolation and characterization of embryonic stem cell-derived cardiac Purkinje cells. Stem Cells Dayt. Ohio 33, 1102-1112.

Nelson, et al. (2016). Irx4 Marks a Multipotent, Ventricular-Specific Progenitor Cell. Stem Cells 34, 2875-2888.

O'Brien, et al. (1993). Positional specification of ventricular myosin light chain 2 expression in the primitive murine heart tube. Proc. Natl. Acad. Sci. U. S. A. 90, 5157-5161.

Oates, et al. (2012). Patterning embryos with oscillations: structure, function and dynamics of the vertebrate segmentation clock. Dev. Camb. Engl. 139, 625-639.

Robertson, et al. Concise Review: Maturation Phases of Human Pluripotent Stem Cell-Derived Cardiomyocytes. Stem Dells Dayt. Ohio 31, (2013).

Sayed, et al. (2015). Transdifferentiation of Human Fibroblasts to Endothelial Cells: Role of Innate Immunity. Circulation 131, 300-309.

Später, et al. (2013). A HCN4+ cardiomyogenic progenitor derived from the first heart field and human pluripotent stem cells. Nat. Cell Biol. 15, 1098-1106.

Tohyama, et al. (2013). Distinct metabolic flow enables large-scale purification of mouse and human pluripotent stem cell-derived cardiomyocytes. Cell Stem Cell 12, 127-137.

Tsuchimochi, et al. (1986). Expression of myosin isozymes during the developmental stage and their redistribution induced by pressure overload. Jpn. Circ. J. 50, 1044-1052.

Witty, et al. Generation of the epicardial lineage from human pluripotent stem cells. Nat. Biotechnol. 32, 1026-1035 (2014).

Yang, et al. (2014). Engineering Adolescence: Maturation of Human Pluripotent Stem Cell-derived Cardiomyocytes. Circ. Res. 114, 511-523.

Yang, et al. The functional expression of TLR3 in EPCs impairs cell proliferation by induction of cell apoptosis and cell cycle progress inhibition, Int'l Immunophramacology, vol. 11 (2011) pp. 2118-2124.

Zhang, et al. (2012). Extracellular matrix promotes highly efficient cardiac differentiation of human pluripotent stem cells: the matrix sandwich method. Circ. Res. 111, 1125-1136.

Kracklauer, et al. (2013). Discontinuous thoracic venous cardiomyocytes and heart exhibit synchronized developmental switch of troponin isoforms. FEBS J. 280, 880-891.

Lian et al., "Robust cardiomyocyte differentiation from human pluripotent stem cells via temporal modulation of canonical Wnt signaling," PNAS, 2012, vol. 109, E1848-1857 and Supporting Information.

Wei and Jin, "Troponin T isoforms and posttranscriptional modifications: evolution, regulation, and function," Arch Biochem Biophys, 2011, 5050(2):144-154.

* cited by examiner

FIGS. 1A-1F, CONTINUED
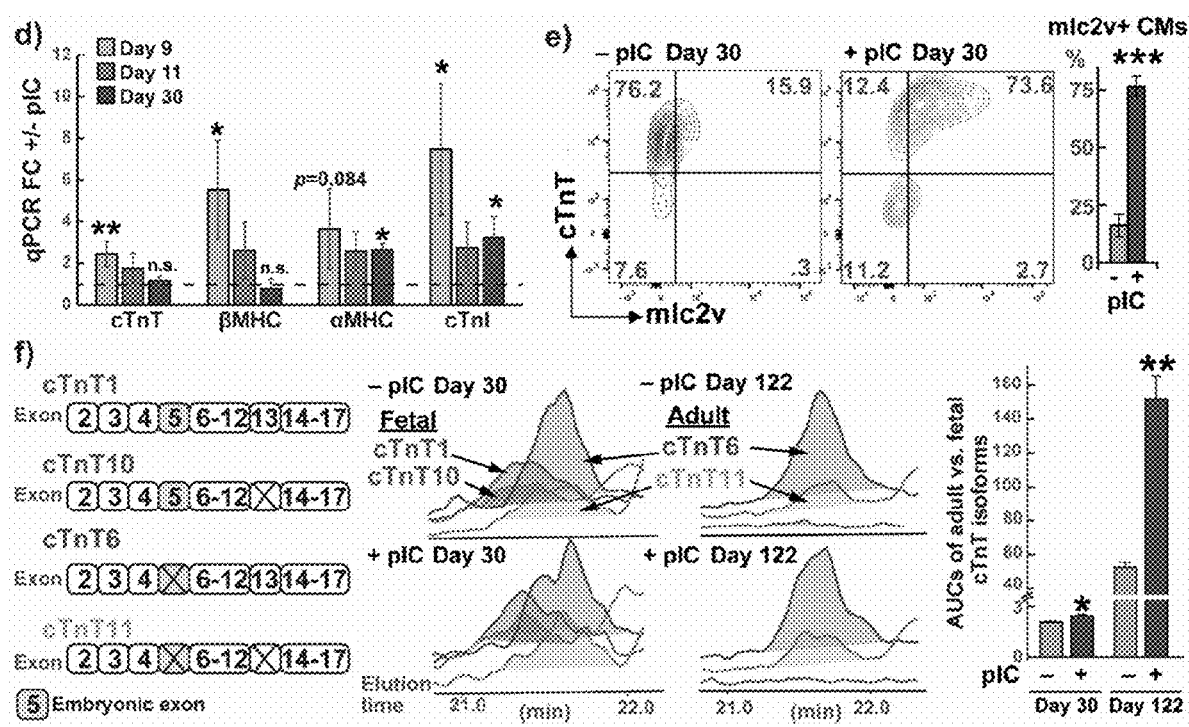

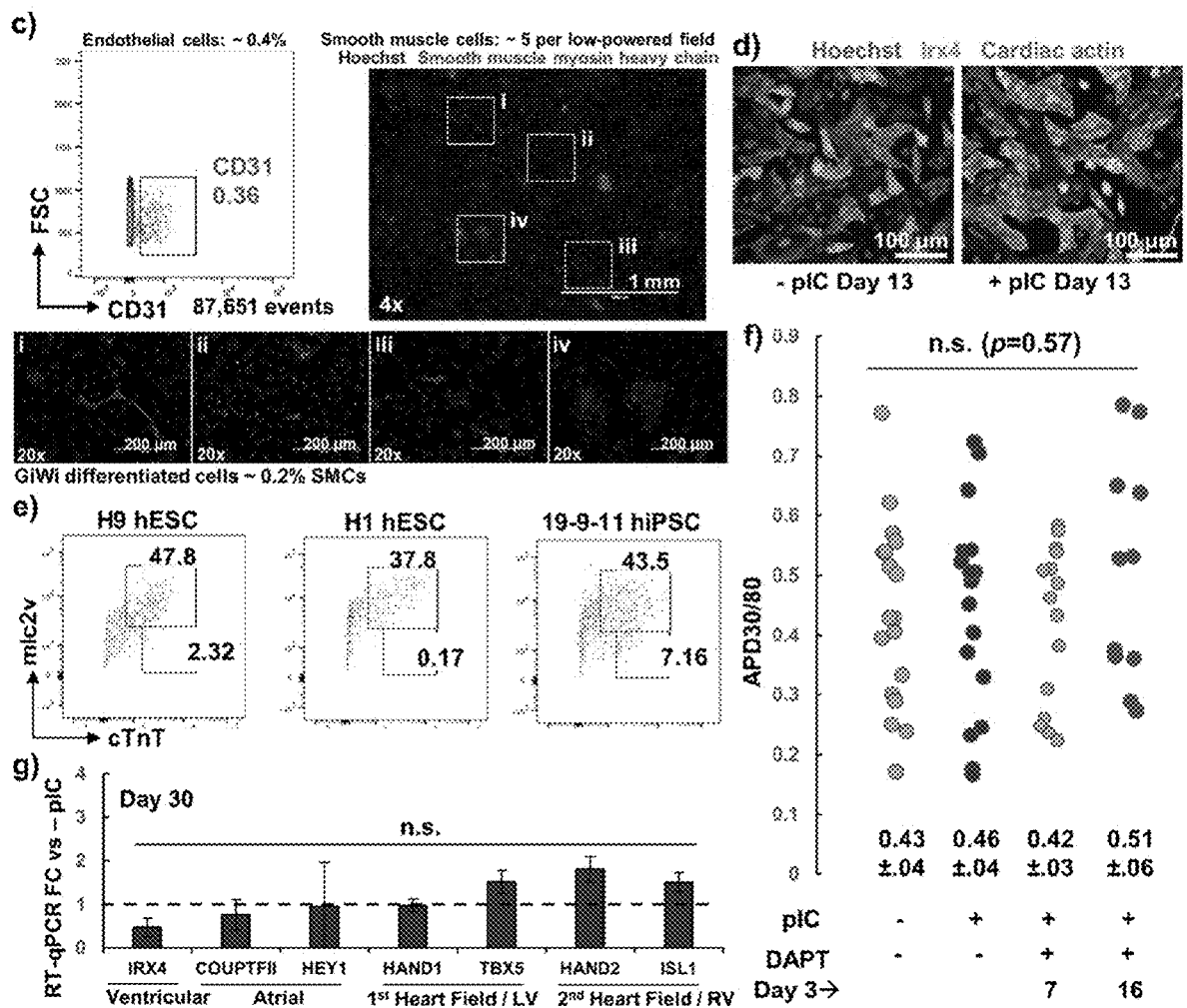
FIGS. 2A-2G, CONTINUED

FIGS. 3A-3G, CONTINUED
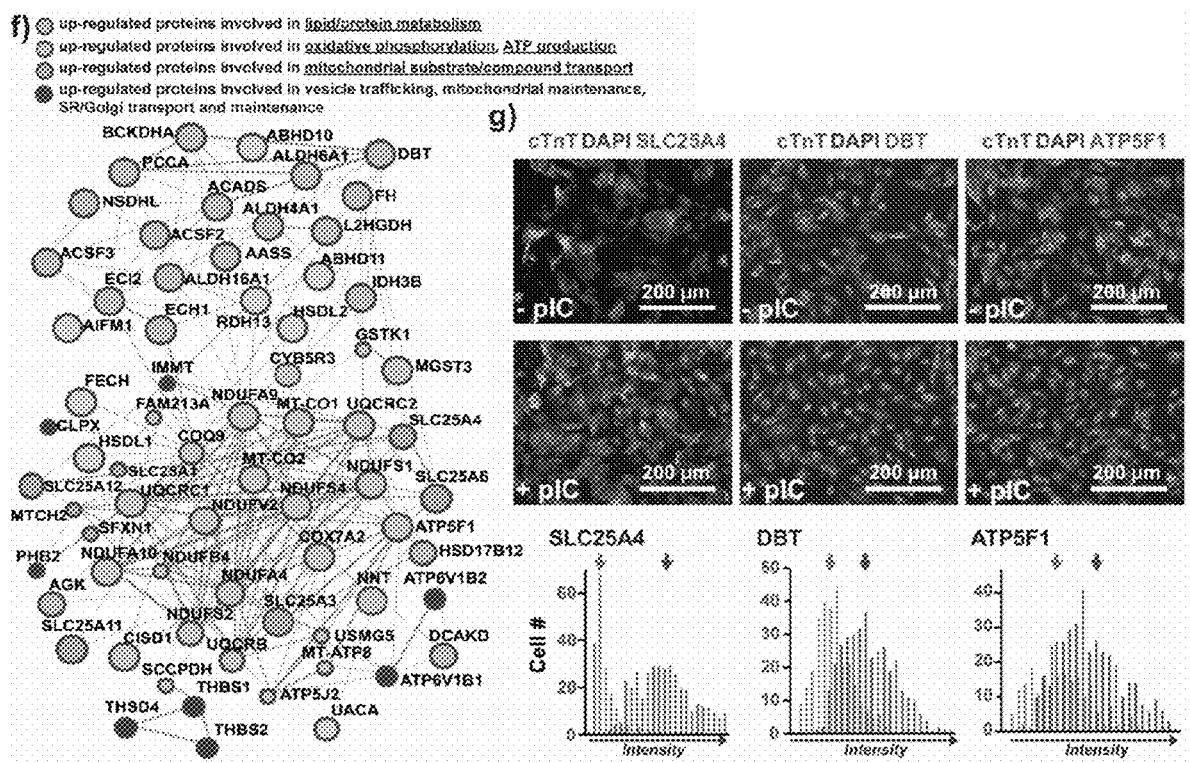

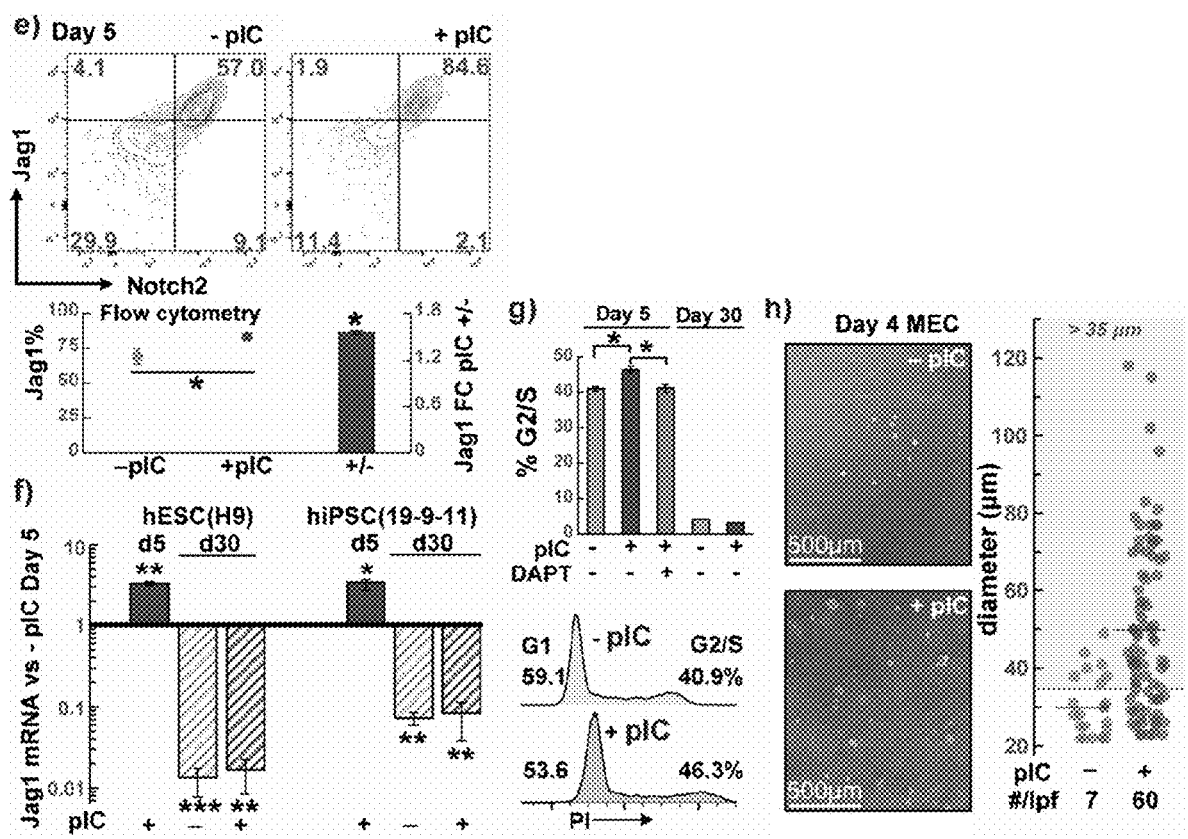
FIGS. 5A-5H, CONTINUED

FIGS. 8A-8E, CONTINUED
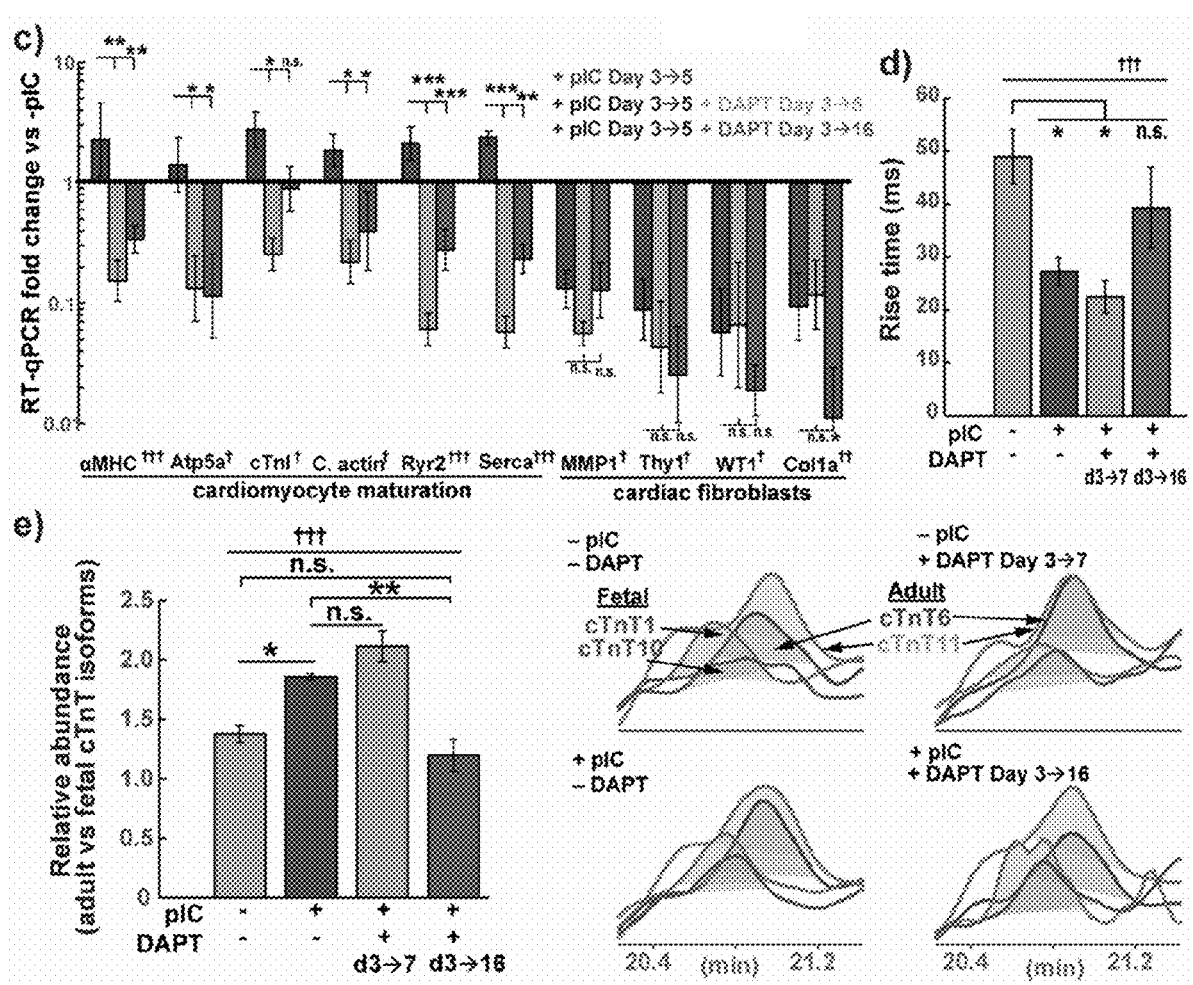

FIGS. 9A-9G, CONTINUED
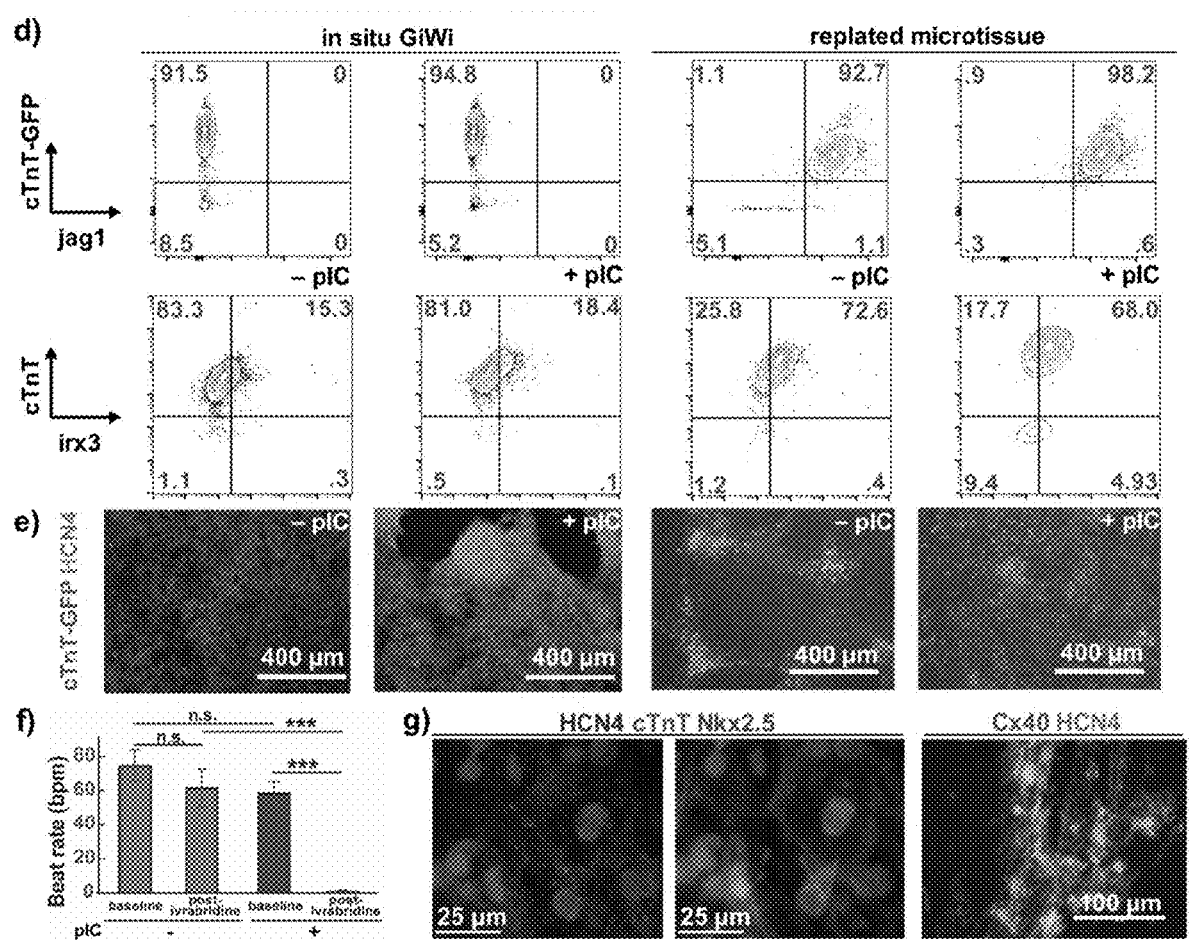

FIGS. 10A-10B, CONTINUED
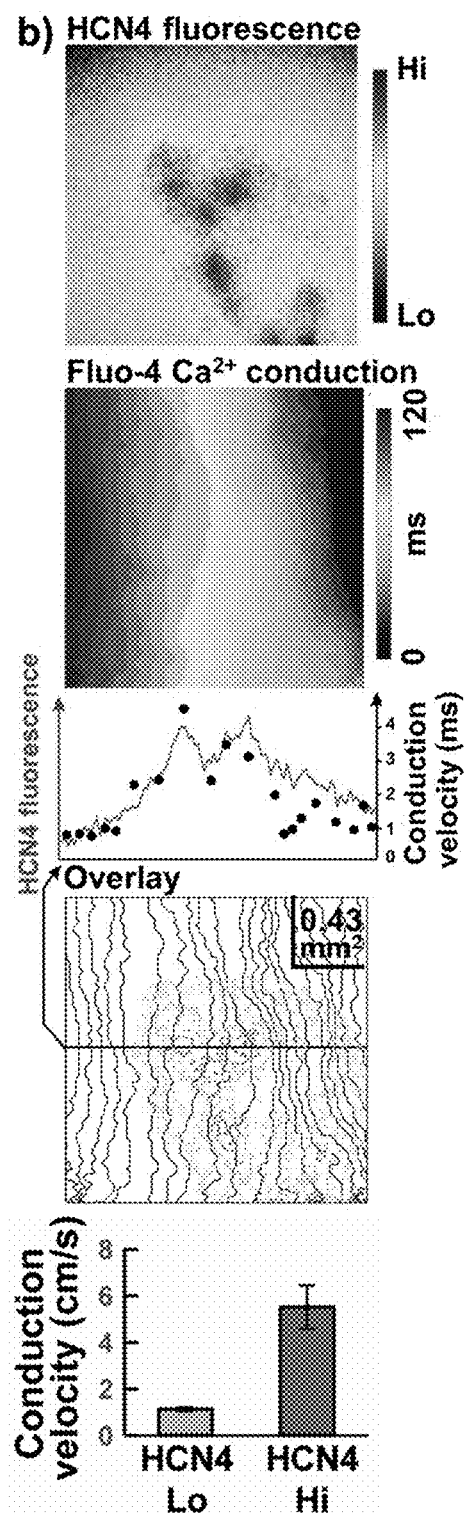

FIGS. 11A-11D, CONTINUED
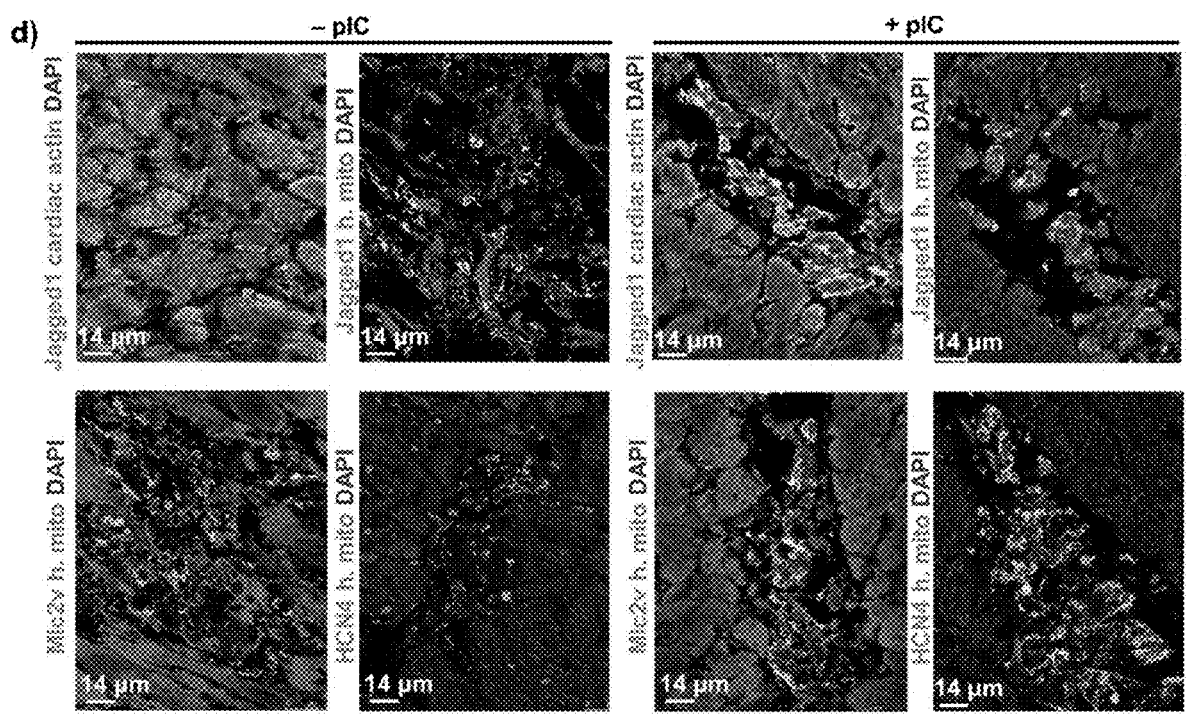

```
SEQUENCE LISTING

<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: synthetic

<400> SEQUENCE: 1
ccggaggtgc tatctgtctg ctctactcga gtagagcaga cagatagcac cttttt      57

<210> SEQ ID NO 2
<211> LENGTH: 57
<212> TYPE: DNA
<213> ORGANISM: Artificial Sequence
<220> FEATURE:
<223> OTHER INFORMATION: synthetic

<400> SEQUENCE: 2
ccgggcttgg aatgagactg ctgatctcga gatcagcagt ctcattccaa gctttt      57
```

METHOD OF MAKING CARDIOMYOCYTES FROM HUMAN PLURIPOTENT CELLS

CROSS-REFERENCE TO RELATED APPLICATION

This application claims priority to U.S. Provisional Application Ser. No. 62/402,785, filed Sep. 30, 2016, which is incorporated by reference in its entirety for all purposes.

STATEMENT REGARDING FEDERALLY SPONSORED RESEARCH OR DEVELOPMENT

This invention was made with government support under HL129798, HL099773, and HL126452 awarded by the National Institutes of Health. The government has certain rights in the invention.

BACKGROUND OF THE INVENTION

Directed differentiation of human induced pluripotent stem cells to somatic cell lineages can create billions of patient-specific human cells for the study of development and disease, high-throughput drug screening, and therapy. However, the final differentiated cells from these protocols often have immature characteristics relative to their adult counterparts. Similarly, developmentally intermediate progenitor cells isolated from these protocols may hold promise for therapy because they retain degrees of cell proliferation and plasticity, but thus far progenitors have been largely analyzed in terms of the fate- or cell-type potency of their derivatives rather than their capacity for maturation.

BRIEF SUMMARY

In the developing field of cardiac regenerative medicine, a temporal Wnt-modulation protocol (the "GiWi protocol") is used to differentiate human pluripotent stem cells (embryonic stem cells or induced pluripotent cells) into cardiomyocytes (CMs) in in vitro culture using small molecules. See, e.g., Lian, X, et al., Robust cardiomyocyte differentiation from human pluripotent stem cells via temporal modulation of canonical Wnt signaling, Proc. Nat. Acad. Sci. 109:27, E1848-E1857, published online May 29, 2012, incorporated herein by reference as if set forth herein, and US Published Patent Application Publication Numbers 2013/0189785, 2014/0134733, 2016/0068814, each incorporated herein by reference as if set forth herein. An improvement to the GiWi protocol, disclosed herein, includes a step of priming mesoderm stage cells in the in vitro differentiation culture by exposing the cells to an activator of innate immunity. When the cardiac mesoderm cells, precursors to cardiac progenitor cells, are subjected to innate immunity activation, a population of cardiomyocytes is generated that is more developmentally mature than is generated in the GiWi protocol without the priming step. The primed cardiac progenitors are fate-matched with (i.e., give rise in the protocol to the same cell types as) the progenitors present in cultures processed according to the existing protocol. Both types of progenitors (primed and unprimed) differentiate in the protocol to cardiomyocytes. However, the cardiomyocytes obtained from primed cardiac progenitors are more mature and more organized, and are able to form micro-cardiac organoids that appear resistant to spontaneous and provoked arrhythmias, and are expected to be better able to engraft or home to the heart when delivered to a subject after heart injury.

In one approach, priming can be achieved by stimulating innate immunity of cells at an appropriate stage of differentiation, namely during the period of transition of mesoderm cells to cardiac progenitor cells (CPCs), known to occur between days 3 and 5 of the GiWi protocol. Cellular innate immunity can be activated by exposing the mesoderm cells to a TLR3 ligand or activator of NF-Kb signaling. Following activation, the primed cardiac progenitors differ from cardiac progenitors produced without this activating or "priming" step. The differences are evident in the cardiomyocytes generated following continued differentiation according to the GiWi protocol, where the cardiac progenitors are primed (+Poly I:C) or not primed (−Poly I:C). The +Poly I:C progenitors are also referred to herein as "primed cardiac progenitors" or simply as "primed progenitors," whereas the −Poly I:C progenitors are referred to as "conventional cardiac progenitors" or as "conventional progenitors." Occasional reference to "activated" rather than "primed" is intended to refer to the same cells. Cardiomyocytes obtained by further differentiation of both primed- and conventional cardiac progenitors can be characterized by standard measures of cardiomyocyte maturity. Cardiomyocytes generated after 30 days in the GiWi differentiation protocol from activated cardiac progenitors are referred to as being "from primed progenitors," as opposed to the "conventional cardiomyocytes" obtained in the GiWi protocol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B demonstrates hPSC-CM cell size as quantified by area of cardiac troponin T (cTnT) immunofluorescence, n=4 passages ea. >50 cells.

FIG. 1C shows transmission electron micrographs of hPSC-CMs demonstrating myofilaments (yellow arrows) and plotted individual sarcomere length measurements. Mean illustrated.

FIG. 1D demonstrates RT-qPCR of myofilament genes for day 9, 11, and 30 cardiomyocytes, fold change +/−pI:C-treated progenitors.

FIG. 1E shows flow cytometry plots for day 30 hPSC-CMs co-stained with cTnT and myosin light chain 2v (MLC2v) from the different progenitors with average data, n=3.

FIG. 1F demonstrates top-down mass spectrometry for cTnT isoforms area-under-the-curve (AUC) ratio of adult to fetal isoforms for day 30 and day 122 hPSC-CMs, n=3. t TestP*<0.05, <0.01, *<0.001.

FIG. 2B. Left: Thy1$^+$ cells represented 60-70% of non-cardiomyocytes in GiWi differentiation by flow cytometry, which did not change between primed and untreated progenitors. Right: Thy1$^+$ cells were co-stained with other markers of fibroblasts (fibroblast-specific protein 1 and fibroblast collagenase) as well as WT1, a marker of epicardium and derived cells from human pluripotent stem cells, including fibroblasts (Witty et al., 2014).

FIG. 2C. Left: Flow cytometry of differentiated GiWi cells for CD31$^+$ endothelial cells showed less than 0.5% of cells in the GiWi protocol. Right: Smooth muscle myosin heavy chain was evaluated by immunofluorescence in differentiated cells and found to be <0.2% of cells.

FIG. 2D demonstrates positive Irx4 immunostaining in early day 13 hPSC-CMs derived from both pI:C-primed and unprimed progenitors.

FIG. 2E demonstrates flow cytometry for myosin light chain 2v (MLC2v) and cTnT in day 200+ hPSC-CMs from untreated progenitors reveals the vast majority of cardiomyocytes from untreated progenitors eventually become positive for MLC2v expression as well.

FIG. 2F demonstrates that hPSC-CMs from primed and untreated progenitors did not differ in APD30/80 (ratio of action potential duration at 30% of repolarization over action potential duration at 80% of repolarization) as assessed using optical voltage-sensitive dye RH237, a distinguishing measure of action potential shape between atrial and ventricular cardiomyocytes.

FIG. 2G demonstrates that chamber-specific gene quantification by RT-qPCR in day 30 hPSC-CMs from primed progenitors, with fold change relative to cardiomyocytes from untreated progenitors, revealed no cell type differences in cardiomyocytes between different progenitors.

FIG. 3B demonstrates quantification of Oxygen Consumption Rate (OCR) using a Seahorse analyzer. Data were normalized to total protein fold change of hPSC-CMs from primed to untreated progenitors, n=4.

FIG. 3C demonstrates a volcano plot of global quantitative bottom up proteomic analysis of up- and downregulated proteins from hPSC-CMs treated with pI:C as compared to no treatment.

FIG. 3D demonstrates ontology analysis revealed majority of the up-regulated proteins involved in primary metabolic process and cell communication.

FIG. 3E is a heat-map of the top 34 upregulated proteins involved in metabolic processes and mitochondrial function.

FIG. 3F demonstrates the protein-protein interaction network of upregulated metabolic proteins, predominantly involved in oxidative phosphorylation and ATP production (yellow), as well as lipid/amino acid metabolism (green). Proteins important for mitochondrial substrate/compound transport (blue) and the crosstalk of mitochondrial and SR/Golgi compartments (red) were also upregulated. Full interactome see FIG. 4C.

FIG. 3G demonstrates immunostaining and quantification of mean fluorescence of three top upregulated metabolic proteins. Means labeled. Unmerged images see FIG. 4C. t TestP*<0.05, <0.01, *<0.001.

FIG. 4A shows analysis of RH237 optical action potentials from day 30-60 hPSC-CMs from primed and untreated progenitors.

FIG. 4B is a Venn diagram showing the number of proteins identified by mass spectrometry in day 30 hPSC-CMs from pI:C primed or untreated progenitors.

FIG. 4C demonstrates a protein-protein interaction network of the pI:C up-regulated and down-regulated proteins in hPSC-CMs and their molecular function.

FIG. 4D shows unmerged images of immunostaining of top hits obtained from bottom-up proteomics.

FIG. 5A is a RNA-seq volcano plot of primed vs. untreated cardiac progenitors. Significantly altered genes with fold change >±2 in green, >±1 in red.

FIG. 5B demonstrates pI:C enriched gene neighborhood protein-protein interactome analysis highlighting classical mitogen and replication components.

FIG. 5C demonstrates RT-qPCR validation of RNA-seq candidates in the TGFβ and Notch pathways, n=4.

FIG. 5D shows a cardiac crescent-stage mouse embryo in transverse section, immunolabeled for Jagged-1 (Jag1). ys—yolk sac, cc—cardiac crescent, n—notochord, e—endoderm.

FIG. 5E demonstrates flow cytometry data for day 5 progenitors for Jag1 and Notch 2, which shows that pI:C treatment increased the number of Jag1 positive cells and median fluorescence signal-to-noise.

FIG. 5F demonstrates RT-qPCR for Jag1 in day 5 cardiac progenitors and day 30 hPSC-CMs plotted as fold change relative to day 5 untreated progenitors from iPS and ES pluripotent cell lines, n=4.

FIG. 5G demonstrates propidium iodide staining and linear mode flow cytometry for cell cycle quantification in day 5 cells, n=3, and comparison to day 30 cardiomyocytes.

FIG. 5H demonstrates phase images and colony quantification of cardiac progenitors 4 days after dissociation and suspension in three-dimensional 1% methylcellulose medium shows more numerous colonies in +pI:C progenitors (defined as object diameter >35 μn). t TestP*<0.05, <0.01, *<0.001; ANOVA P †<0.05, ††<0.01.

FIG. 7A demonstrates Jag1 expression in untreated and pI:C primed cardiac progenitors. The images reveal Jag1 surface expression as well as nuclear localization.

FIG. 7B demonstrates near-infrared (Licor) immunoblotting of Jag1 and GAPDH in day 5 progenitors revealed a significant, 1.5-fold increase in Jag1 expression in primed progenitors consistent with the fold-change measured by flow cytometry (FIG. 5E).

FIG. 7C demonstrates that Jag1 and Notch2 were the majorly expressed Notch receptors and ligands in absolute expression in RNA-seq of day 5 cardiac progenitors. t TestP*<0.05, <0.01, *<0.001.

FIG. 8B. Left: Multiphoton projection image of cTnT-GFP reporter hPSC-CMs from progenitors that were dissociated and replated in defined conditions. Right: Yield and purity of hPSC-CMs from replated primed and untreated progenitors at high and low seeding density, n=3-5.

FIG. 8C demonstrates cardiac maturation and fibroblast gene quantification by RT-qPCR in hPSC-CMs from primed progenitors, or dual treated with Notch inhibitor DAPT, fold change relative to hPSC-CMs from untreated progenitors, referenced to cTnT expression, n=3-5.

FIG. 8D demonstrates optical upstroke velocity as measured using the voltage-sensitive dye RH237 (quantified by time required to traverse 10 to 90% action potential amplitude, rise time) from hPSC-CM differentiated from primed and untreated progenitors, in the presence or absence of the Notch inhibitor DAPT at times indicated, n=17 individual cells from 4 passages.

FIG. 8E demonstrates Top-down mass spectrometry for cTnT isoforms, AUC ratio of adult to fetal isoforms for day 30 hPSC-CMs from primed and untreated progenitors, in the presence or absence of the Notch inhibitor DAPT. n=3. t TestP*<0.05, <0.01, *<0.001; ANOVA P †<0.05, ††<0.01, †††<0.001.

FIG. 9B. Beat angle range (the maximum deviation over a video in mean beat vector angle) was decreased in primed progenitor derived sheets, n=3.

FIG. 9C demonstrates Motion velocity analysis of hPSC-CM sheets from replated progenitors over time from primed and untreated progenitors. Motion velocity (pixels/s) increases from blue (0) to red.

FIG. 9D. Top, Jag1 and cTnT-GFP and, bottom, Irx3 and cTnT flow cytometry of day 30 cells revealed that, compared to in situ-derived cardiomyocytes, replated progenitor-derived cardiomyocytes majorly expressed Jag1 and Irx3 markers of ventricular trabeculae.

FIG. 9E shows live cell immunostaining for HCN4 of cTNT-GFP cardiomyocyte reporter cell line following in situ differentiation or replated progenitor differentiation, with and without pI:C treatment. HCN4+ cells are evident only in sheets from replated progenitors.

FIG. 9F. Spontaneous beat rate of replated progenitor-derived cardiomyocyte sheets demonstrates primed progenitor sheets are specifically sensitive to the HCN4 channel blocker ivrabradine, n=3.

FIG. 9G demonstrates that HCN4+ cells were found to coexpress cTnT, Nkx2.5, and Cx40 as determined by immunostaining. t TestP*<0.05, <0.01, *<0.001

FIG. 10B demonstrates HCN4 and Fluo-4 Ca live co-imaging revealed that conduction velocity correlated with HCN4$^{Hi}$ staining. t TestP*<0.05, **<0.01.

FIG. 11B demonstrates immunostaining of mouse heart sections from mice not surviving the first week after myocardial infarction with antibodies to cTnT and for human mitochondria (h. mito).

FIG. 11C demonstrates that human mitochondria cells express nuclear Aurora B Kinase, a marker of cell division/proliferation.

FIG. 11D demonstrates that human mitochondria+ cells expressed Jag1, HCN4, and Mlc2v.

FIG. 12A shows near-infrared western blotting of NFκB and its phosphorylated (inactivated) inhibitor IκB in pI:C treated and untreated progenitors. The blot demonstrates an increase in NFκB activity in pI:C treated (primed) CPCs.

FIG. 12B. Epifluorescence images (left) and phase contrast images (right) of day 20 hPSC-CMs generated from H9-TnT-GFP cell line from pI:C treated progenitors, pI:C treated progenitors+QNZ (NFκB inhibitor), or untreated progenitors. Green fluorescence indicates the presence of hPSC-CMs.

FIG. 12C. RT-qPCR data for day 30 cardiomyocyte maturation gene expression of cardiomyocytes from pIC treated or pIC+QNZ-treated progenitors, fold change relative to cardiomyocytes from untreated progenitors (−). n=3-5, referenced to GAPDH expression.

DETAILED DESCRIPTION

Figures 1A, 1B, 1C, 1D, 1E, 1F:
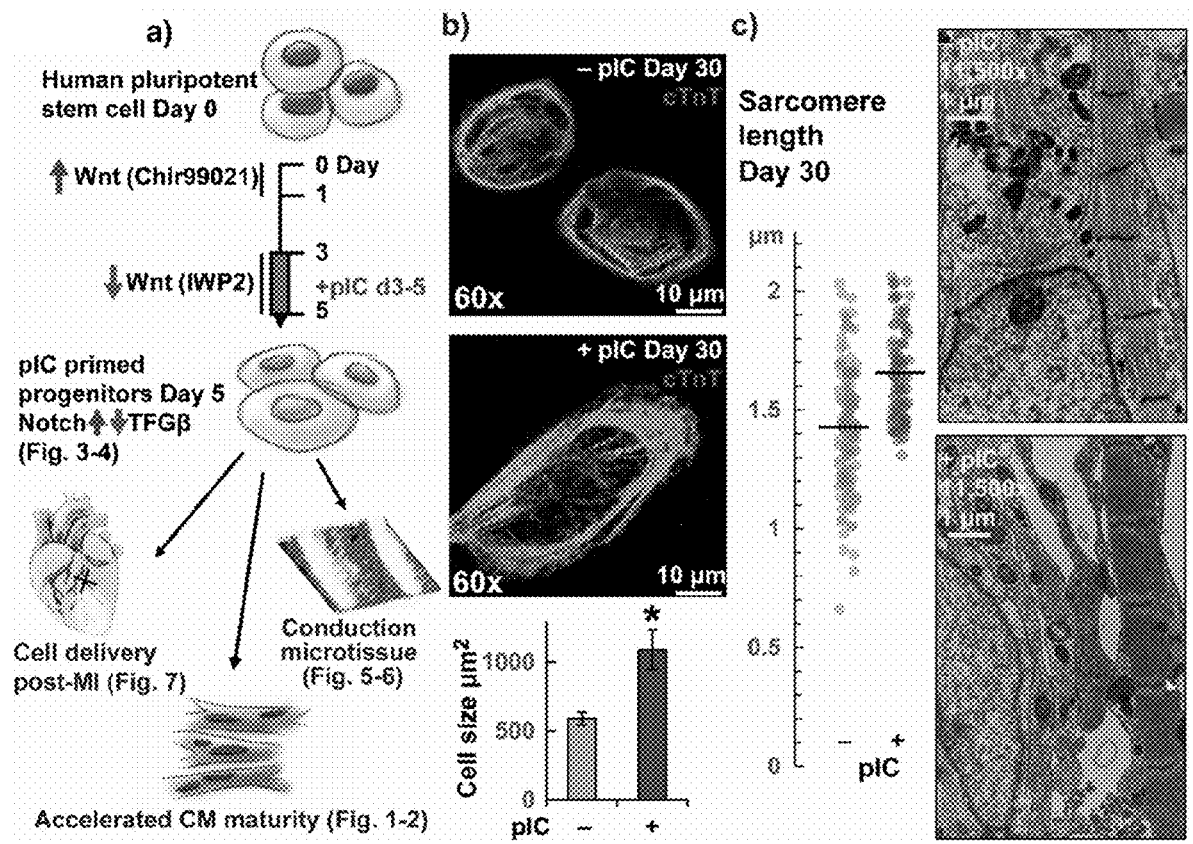
FIGS. 1A-1F—Increased maturation of myofilament proteins and structure in hPSC-CMs from primed cardiac progenitors FIG. 1A demonstrates that hPSC-derived cardiac progenitors generated in a small molecule biphasic Wnt modulation cardiac differentiation protocol treated with polyinosinic-polycytidylic acid (pI:C) demonstrate increased Notch signaling and decreased TGFβ signaling leading to accelerated hPSC-derived cardiomyocyte (hPSC-CM) maturation, formation of ventricular conduction microtissue, and improved mortality following transplantation in a preclinical animal model of myocardial infarction.

All publications, including but not limited to patents and patent applications, cited in this specification are herein incorporated by reference as though set forth in their entirety in the present application.

The methods provided herein are based at least in part on the inventors' development of methods for producing cardiomyocytes having accelerated maturation and capable of improving survival in a mouse myocardial infarction model. As described herein, the methods comprise priming human pluripotent stem cell-derived cardiac progenitor cells (CPCs) using an activator of Toll-Like Receptor-3 (TLR3) such as a double-stranded RNA mimetic. The inventors further developed methods for dissociating primed CPCs to generate cardiac conduction system-like cells that self-organize to form a ventricular conduction system microtissue. The methods have valuable applications such as inexpensive and reproducible generation of primed cardiac progenitors and more developmentally mature cardiomyocytes. Generating such primed cardiac progenitors and developmentally mature cardiomyocytes in completely chemically-defined conditions might facilitate translation of these cells to regenerative therapies.

Accordingly, in a first aspect, provided herein is a method of generating a population of primed cardiac progenitors from pluripotent stem cells, the method including the steps of: (i) activating Wnt/β-catenin signaling in cultured pluripotent stem cells (e.g., human pluripotent stem cells) to obtain a first cell population; (ii) culturing cells of the first cell population for a period following the end of the activating step until cardiac mesoderm cells are obtained; and (iii) after the culturing period in step (ii), inhibiting Wnt/β-catenin signaling in the cardiac mesoderm cells in the presence of an activator of innate immunity (e.g., a TLR3 ligand) until a second cell population comprising primed cardiac progenitors is obtained. While not wishing to be bound by theory, it is believed that, in various embodiments described herein, activation is achieved by stimulating innate immunity of cells at an appropriate stage of differentiation, namely during the period of transition of mesoderm cells to cardiac progenitor cells (CPCs), which is known to occur between days 3 and 5 of the GiWi protocol. Activating TLR3 can have potentially stable and long-lasting effects on gene expression. Accordingly, it is believed that changes in gene expression resulting from activation of TLR3 "prime" cardiac progenitor cells by increasing Notch signaling and proliferation networks, and by promoting differentiation of the primed CPCs into cardiomyocytes exhibiting accelerated maturation.

As used herein, the term "primed cardiac progenitor" refers to a cardiac progenitor cell (CPC) that has been altered by culture in the presence of an activator of innate immunity (e.g., a Toll Like Receptor 3 (TLR3) ligand, an activator of NF-κB-mediated signaling ("NF-κB activator")). The term also refers to human pluripotent stem cell-derived cardiac progenitor cells treated in a particular manner (i.e., cultured in the presence of a TLR3 ligand or a NF-κB activator) prior to differentiation of the cardiac progenitor cells. As described herein, primed cardiac progenitors exhibit increased surface expression of the ligand Jagged-1 (Jag1).

In some embodiments of the differentiation methods described herein, the TLR3 ligand which is a mimetic of a double stranded RNA (dsRNA). For example, the mimetic of a double stranded RNA can be a synthetic dsRNA such as polyinosinic-polycytidylic acid (polyI:C or "pI:C") or poly-adenylic-polyuridylic acid (poly A:U). Polyinosine-polycytidylic acid (Poly (I:C)) is a double stranded RNA molecule with a MW distribution up to 1,000,000 Daltons. PolyI:C is a Toll Like Receptor 3 (TLR3) ligand that mimics viral RNA and is a known stimulant of the innate immune response. In some cases, cells of the cultured first population are cultured in the presence of an activator of innate immunity (e.g., pI:C) for about two days. The average chain length for the Poly (I:C) ranges between 300 to 6,000 base pairs, corresponding to approximately 180,000 to about 3,600,000 daltons. The molecular formula is $(C_{10}H_{10}N_4NaO_7P)_x$ $(C_9H_{11}NaN_3O_7P)_x$. PolyI:C is commercially available in various forms (e.g., Polyinosinic-Polycytidylic Acid Sodium Salt, Product No. P-0913, Sigma), but can be produced using the individual homopolymers Poly Inosine (I) and Poly Cytidine (C). NF-κB activators include, without limitation, cytokines such as tumor necrosis factor alpha (TNF-α), pathogen-associated molecular patterns (PAMPs) such as lipopolysaccharide (LPS), and phorbol esters.

Typically, the second cell population obtained by the disclosed methods comprises a very high proportion of primed cardiac progenitors. In some embodiments, the second cell population comprises about 50% to about 99% primed cardiac progenitors, e.g., about 52%, 55% 67%, 70%, 72%, 75%, 80%, 85%, 90%, 95%, 98%, or another percent from about 50% to about 99% primed cardiac progenitors.

In some embodiments, after ending the inhibition of Wnt/β-catenin signaling initiated during step (iii), as described herein, the resulting second population of cells, comprising primed cardiac progenitors, is cultured for an additional period of time to obtain a cell population comprising developmentally mature cardiomyocytes. As used herein, the terms "developmentally mature cardiomyocyte" and "cardiomyocyte having accelerated maturation" are used interchangeably herein and refer to cardiomyocytes differentiated from (derived from) primed cardiac progenitor cells. The terms encompass cardiomyocytes that exhibit an earlier activation of the cardiomyogenic transcriptional program as revealed by increased expression of Jagged-1 (Jag1), which is a Notch ligand, and proliferative cell signaling networks as compared to expression of these markers in cardiomyocytes not derived from primed cardiac progenitor cells. A compared to cardiomyocytes derived from unprimed cardiac progenitors, developmentally mature cardiomyocytes are also structurally distinct. In particular, developmentally mature cardiomyocyte are larger (in some cases, twice as large) and exhibit longer, more organized sarcomeres, and higher expression of myofilaments found in the adult ventricular heart such as cardiac troponin I (cTnI), alpha-myosin heavy chain (αMHC), and myosin light chain 2v (MLC2v) as compared to those cardiomyocytes derived from unprimed cardiac progenitors (Kamakura et al., 2013; Kracklauer et al., 2013; Lian et al., 2012; O'Brien et al., 1993; Robertson et al., 2013; Tsuchimochi et al., 1986). Referring to FIGS. 1D-1E, cardiomyocytes derived from primed CPCs exhibit an increased ratio of adult myofilament isoforms to fetal myofilament isoforms, and ratio increased as the primed progenitor-derived cardiomyocytes were maintained in culture (FIG. 1F). Adult myofilament isoforms include, without limitation, cTnI, αMHC, and MLC2v. Expression of such biological markers can be detected at the mRNA level or protein level by standard methods in the art. Sarcomere length and organization can be measured using, for example, standard microscopy and laser diffraction methods in the art.

In some embodiments, where developmentally mature cardiomyocytes are to be generated, certain functional criteria are also assessed. For example, developmentally mature cardiomyocytes exhibit faster action potential upstroke velocity and increased oxidative metabolism as compared to cardiomyocytes derived from non-primed CPCs. Faster optical upstroke velocity can be quantified as a decrease in time for change of 10% to 90% depolarization voltage amplitude. Other functional cardiomyocyte criteria that can be assessed include, but are not limited to, spontaneous contractility, basal and maximal oxygen consumption, and response to electrical pacing, or a combination thereof.

In some embodiments, the additional cell culture period for the second cell population ranges from at least about 9 days to about 140 days, e.g., about 9 days, 10 days, 12 days, 15 days, 20 days, 25 days, 30 days, 35 days, 40 days, 60 days, 80 days, 100 days, 120 days, 140 days, or another culture period, after ending inhibition of Wnt/β-catenin signaling, from at least about 20 days to about 140 days following the end of Wnt/β-catenin signaling inhibition. In one embodiment, the second population of cells is cultured for a period of at least about 9 days after ending inhibition of Wnt/β-catenin signaling.

As demonstrated in the Examples that follow, a time course experiment of myofilament gene expression revealed that "day 9" cardiomyocytes differentiated from primed cardiac progenitors had increased expression of all myofilament genes studied as compared to untreated progenitor-derived cardiomyocytes, suggesting an earlier activation of the cardiomyogenic transcriptional program. It was also demonstrated that administration of primed CPCs to a mouse model of myocardial infarction can improve post-myocardial infarction survival. These data provide further evidence that early changes in gene expression in cardiac progenitors can accelerate cardiomyocyte maturation, promote tissue organization, and enhance the benefits of cardiac cell-based therapies.

In some embodiments, continued culture of the second population (in the absence of Wnt/β-catenin signaling inhibition) yields a cell population comprising about 50% to about 99% developmentally mature cardiomyocytes, e.g., about 52%, 55% 67%, 70%, 72%, 75%, 80%, 85%, 90%, 95%, 98%, or another percent of cardiomyocytes from about 50% to about 99% developmentally mature cardiomyocytes.

In some embodiments, no cell separation step or enrichment method is used to obtain a second cell population comprising at least 70% cardiac troponin T (cTnT)-positive cells. In some cases, the second cell population comprises 80-95% cTnT+ cells without a cell separation or sorting step. In other embodiments, cell separation or enrichment methods, e.g., FACS, MACS, or laser-targeted ablation of non-cardiomyocytes are used to obtain a second cell population further enriched in developmentally mature cardiomyocytes relative to the second cell population prior to application of a cell separation or enrichment method. Cardiomyocytes are identified by the presence of one or more cardiomyocyte markers (e.g., cTnT expression) or functional characteristics (e.g., spontaneous contractility).

As used herein, the term "pluripotent cell" means a cell capable of differentiating into cells of all three germ layers. Examples of pluripotent cells include embryonic stem cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells. Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs).

Defined media and substrate conditions for culturing pluripotent stem cells, as used in the methods described herein, are well known in the art. In some exemplary embodiments, pluripotent stem cells to be differentiated according to the methods disclosed herein are cultured in mTESR®-1 medium (StemCell Technologies, Inc., Vancouver, Calif.), or Essential 8® medium (Life Technologies, Inc.) on a Corning® Synthemax® surface or, in some cases, a Matrigel® substrate (BD Biosciences, NJ) according to the manufacturer's protocol.

Activation of Wnt/β-Catenin Signaling

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibition of Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen et al. (2002), *J Biol Chem*, 277 (26):23330-23335, which describes a Gsk3 comprising a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosphotransferase activity or Gsk3 binding interactions. Suitable small molecule Gsk3 inhibitors include, but are not limited to, CHIR 99021, CHIR 98014, BIO-acetoxime, BIO, LiCl, SB 216763, SB 415286, AR A014418, 1-Azakenpaullone, Bis-7-indolylmaleimide, and any combinations thereof. In some embodiments, any of CHIR 99021, CHIR 98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 5 µM to about 20 µM, e.g., about 6 µM, 8 µM, 10 µM, 12 µM, 14 µM, 16 µM, or another concentration of CHIR99021 from about 5 µM to about 20 In another embodiment, the small molecule Gsk3 inhibitor to be used is CHIR 98014 at a concentration ranging from about 0.2 µM to about 2 µM, e.g., about 0.6 µM, 0.8 µM, 1 µM, 1.2 µM, 1.4 µM, 1.6 µM, or another concentration of CHIR99021 from about 0.2 µM to about 2 µM.

In other embodiments, Gsk3 activity is inhibited by RNA interference knockdown of Gsk3. For example, Gsk3 expression levels can be knocked-down using commercially available siRNAs against Gsk3, e.g., SignalSilence GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNAi system from Clontech (Mountainview, Calif.) Catalog No. 630926, or a cumate-inducible system from Systems Biosciences, Inc. (Mountainview, Calif.), e.g., the SparQ® system, catalog no. QM200PA-2. In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any of the just-mentioned inducible expression systems. Alternatively, a constitutively active, stabilized isoform of β-catenin is used, which contains point mutations S33A, S37A, T41A, and S45A as described, e.g., in Baba et at (2005), Immunity, 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of Axin-β-catenin interaction allows β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-Catenin signaling ranges from about 10 µM to about 100 about 20 µM, 30 µM, 40 µM, 50 µM, 60 µM, 70 µM, 80 µM, 90 µM or another concentration of SKL2001 from about 10 µM to about 100 µM.

Inhibition of Wnt/β-Catenin Signaling

Inhibition of Wnt/β-catenin pathway signaling means inhibition of TCF/LEF-β-catenin mediated gene transcription Inhibition of Wnt/β-catenin pathway signaling can be achieved in a variety of ways including, but not limited to: providing small molecule inhibitors, RNA interference of, or blocking antibodies against functional canonical Wnt ligands or Wnt pathway receptors (e.g., Frizzled and LRP5/6); providing small molecules that promote degradation of β-catenin and/or TCF/LEF; gene interference knockdown of β-catenin and/or TCF/LEF; overexpression of a dominant negative form of β-catenin lacking the sequence for binding to TCF/LEF; overexpressing Axin2 (which increases β-catenin degradation); providing a small molecule inhibitor of a TCF/LEF and β-catenin interaction; and providing a small molecule inhibitor of a TCF/LEF-β-catenin and DNA promoter sequence interaction.

In some cases, inhibition of Wnt/β-catenin pathway comprising cells expressing mesendodermal or mesodermal markers is achieved by contacting the first cell population with one or more small molecule inhibitors of a Wnt ligand (e.g., a small molecule that inhibit secretion of the Wnt ligand) o or inhibit Wnt ligands and their corresponding receptors interaction. Suitable small molecule inhibitors include, but are not limited to, N-(6-Methyl-2-benzothiazolyl)-2-[(3,4,6,7-tetrahydro-4-oxo-3-phenylthieno[3,2-d]pyrimidin-2-yl)thio]-acetamide ("IWP2") available commercially, e.g., as Sigma catalog no. 10536; 2-(3,4,6,7-tetrahydro-3-(2-methoxyphenyl)-4-oxothieno[3,2-d]pyrimidin-2-ylthio)-N-(6-methylbenzo[d]thiazol-2-yl)acetamide ("IWP4") available commercially, e.g., as catalog no. 04-00306 from Stemgent (San Diego, Calif.); 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. 10161; Benzoic acid, 2-phenoxy-, 2-[(5-methyl-2-furanyl)methylene]hydrazide ("PNU-74654"), e.g., Sigma catalog no. P0052; or a combination thereof.

In some embodiments, the first population of cells is contacted with one or more small molecule compounds that promote degradation of β-catenin. In some cases, such small molecule compounds are compounds that, directly or indirectly, stabilize Axin, which is a member of the β-catenin destruction complex, and thereby enhance degradation of β-catenin. Examples of Axin-stabilizing compounds include, but are not limited to, 3,5,7,8-Tetrahydro-2-[4-(trifluoromethyl)phenyl]-4H-thiopyrano[4,3-d]pyrimidin-4-one ("XAV939"), e.g., Sigma catalog no. X3004; 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. 10161. In some cases, such small molecule compounds that, directly or indirectly, activate casein kinase 1α (CK1), which is a member of the β-catenin destruction complex, and thereby enhances degradation of β-catenin. Examples of CK1-stabilizing compounds include, but are not limited to, 6-(Dimethylamino)-2-[2-(2,5-dimethyl-1-phenyl-1H-pyrrol-3-yl)ethenyl]-1-methyl-4,4'-methylenebis[3-hydroxy-2-naphthalenecarboxylate](2:1)-quinolinium ("Pyrvinium pamoate salt hydrate"), e.g., Sigma catalog no. P0027.

A suitable working concentration range for such small molecule inhibitors is from about 0.1 µM to about 100 µM, e.g., about 2 µM, 5 µM, 7 µM, 10 µM, 12 µM, 15 µM, 18 µM, or another working concentration of one or more the foregoing small molecule inhibitors ranging from about 0.1 µM to about 100 µM. In one embodiment, IWP2 or IWP4 are used at a working concentration of about 5 µM. In other embodiments, the above-mentioned small molecule inhibitors are used at the corresponding target $IC_{50}$.

In other embodiments, inhibition of Wnt/β-catenin pathway signaling in the first cell population is enabled by RNA interference to decrease the expression of one or more targets in the Wnt/β-catenin pathway. For example in some cases, RNA interference is against β-catenin itself. In one embodiment, where one or more short hairpin interfering RNAs (shRNAs) are to be used to knock down β-catenin expression, at least one of the following shRNA sequences are used: (SEQ ID NO:1 5'-CCGGAGGTGC-TATCTGTCTGCTCTACTCGAGTAGAGCAGACAGA-TAGCACCTTTT T T-3' or (SEQ ID NO:2) 5'-CCGGGCTTGGAATGAGACTGCT-GATCTCGAGATCAGCAGTCTCAT TCCAAGCTTTTT-3'. Such shRNAs may be transfected as synthetic shRNAs into the first cell population by a number of standard methods known in the art. Alternatively, shRNA sequences may be expressed from an expression vector, e.g., from a plasmid expression vector, a recombinant retrovirus, or a recombinant lentivirus.

In some embodiments, the first cell population is generated from a genetically modified pluripotent stem cell line comprising an inducible expression cassette for expression of an interfering RNA, e.g., an shRNA against β-catenin, as exemplified herein. The use of an inducible expression cassette allows temporal control of β-catenin knockdown. Such temporal control is well suited to the timing of Wnt/β-catenin signaling inhibition used in the differentiation methods described herein.

As an alternative method for inhibiting Wnt/β-catenin signaling, the first cell population is contacted with at least one antibody that blocks activation of a Wnt ligand receptor. In some embodiments, the at least one antibody binds to one or more Wnt ligand family members and inhibits binding of the one or more Wnt ligands to their receptors. Such antibodies are known in the art, as described in, e.g. an anti-Wnt-1 antibody described in He et al. (2004), *Neoplasia*, 6(1):7-14. In other embodiments, the blocking antibody is targeted against a Wnt ligand receptor and blocks the interaction of Wnt ligands with the receptor, as described, e.g., in Gurney et al (2012), *Proc. Natl. Acad. Sci. USA*, 109(29):11717-11722.

In another aspect, provided herein is a method for producing ventricular conduction system cells and ventricular conduction system-like cells in vitro. As used herein, the term "ventricular conduction system-like cells" refers to cells having morphological and functional structure and features of natural Purkinje cells of the ventricular conduction system. Purkinje cells are specialized cardiomyocytes that enable more rapid conduction of electrical impulses based on their increase sodium current, relatively small size (<20 μm across the diameter of the main cell body), and excellent electrical coupling between cells that organize into chains or fibers that are distributed through the ventricles. In certain embodiments, the method comprises (i) activating Wnt/β-catenin signaling in cultured pluripotent stem cells to obtain a first cell population; (ii) culturing the first cell population for a period following the end of the activating step until cardiac mesoderm cells are present in the cultured first cell population; (iii) after the culturing period in step (ii), inhibiting Wnt/β-catenin signaling in the cardiac mesoderm cells in the presence of an activator of innate immunity until a second cell population comprising primed cardiac progenitors is obtained; and (iv) dissociating the second cell population and replating the dissociated cells on a substrate whereby the replated cells self-organize into a conductive microtissue comprising sheets of cardiomyocytes and ventricular conduction system-like cells positive for expression of Hyperpolarization-activated Cyclic Nucleotide-gated channel 4 (HCN4$^+$). HCN4 is an ion channel important for pacemaker potential and a marker useful for identifying an early cardiomyogenic progenitor pool as well as ventricular conduction system cells. As used herein, "HCN4" refers to a nucleic acid or peptide sequence corresponding to human HCN4, or an ortholog thereof An exemplary human HCN4 gene sequence is provided by GenBank sequence NM 005477.

In some cases, ventricular conduction system-like cells are produced using untreated/unprimed CPCs. In such cases, the method comprises (i) activating Wnt/β-catenin signaling in cultured pluripotent stem cells to obtain a first cell population; (ii) culturing the first cell population for a period following the end of the activating step until cardiac mesoderm cells are present in the cultured first cell population; (iii) after the culturing period in step (ii), inhibiting Wnt/β-catenin signaling in the cardiac mesoderm cells until a second cell population is obtained; and (iv) dissociating the second cell population and replating the dissociated cells on a substrate whereby the replated cells self-organize into a conductive microtissue comprising sheets of cardiomyocytes and ventricular conduction system-like cells positive for expression of HCN4$^+$. The replating step of the second population (regardless of whether that population comprises primed CPCs or unprimed CPCs) is particularly important to produce a conductive microtissue comprising HCN4$^+$ cells since these cells do not form in the absence of replating.

In some cases, HCN4$^+$ ventricular conduction system-like cells obtained as described herein are isolated cells or isolated populations of cells. The term "isolated" as used herein refers to a cell or cell population that has been removed from an organism in which it was originally found or a descendant of such a cell. The term also refers to cells cultured in vitro (e.g., in the presence of other cells) and removed and separated from a mixed or heterogeneous population of cells. In some cases, isolated HCN4+ ventricular conduction system-like cells are removed and separated from other cells of a conductive microtissue by any appropriate cell isolation method. In certain embodiments, at least 75%, 80%, 85%, 90%, 95%, 98%, or more of the cells in an isolated population of ventricular conduction system-like cells express HCN4 (i.e., are HCN4$^+$). In certain embodiments, HCN4 expression is detected using a nucleic acid that hybridizes to a nucleic acid sequence encoding HCN4 (e.g., HCN4 mRNA) or an antibody having specificity to HCN4, such as an antibody that binds to an extracellular portion of HCN4 (e.g., an extracellular peptide of HCN4 or an extracellular site of modification on HCN4, such as a glycosylation site).

Compositions

Figures 4A, 4B, 4C, 4D:
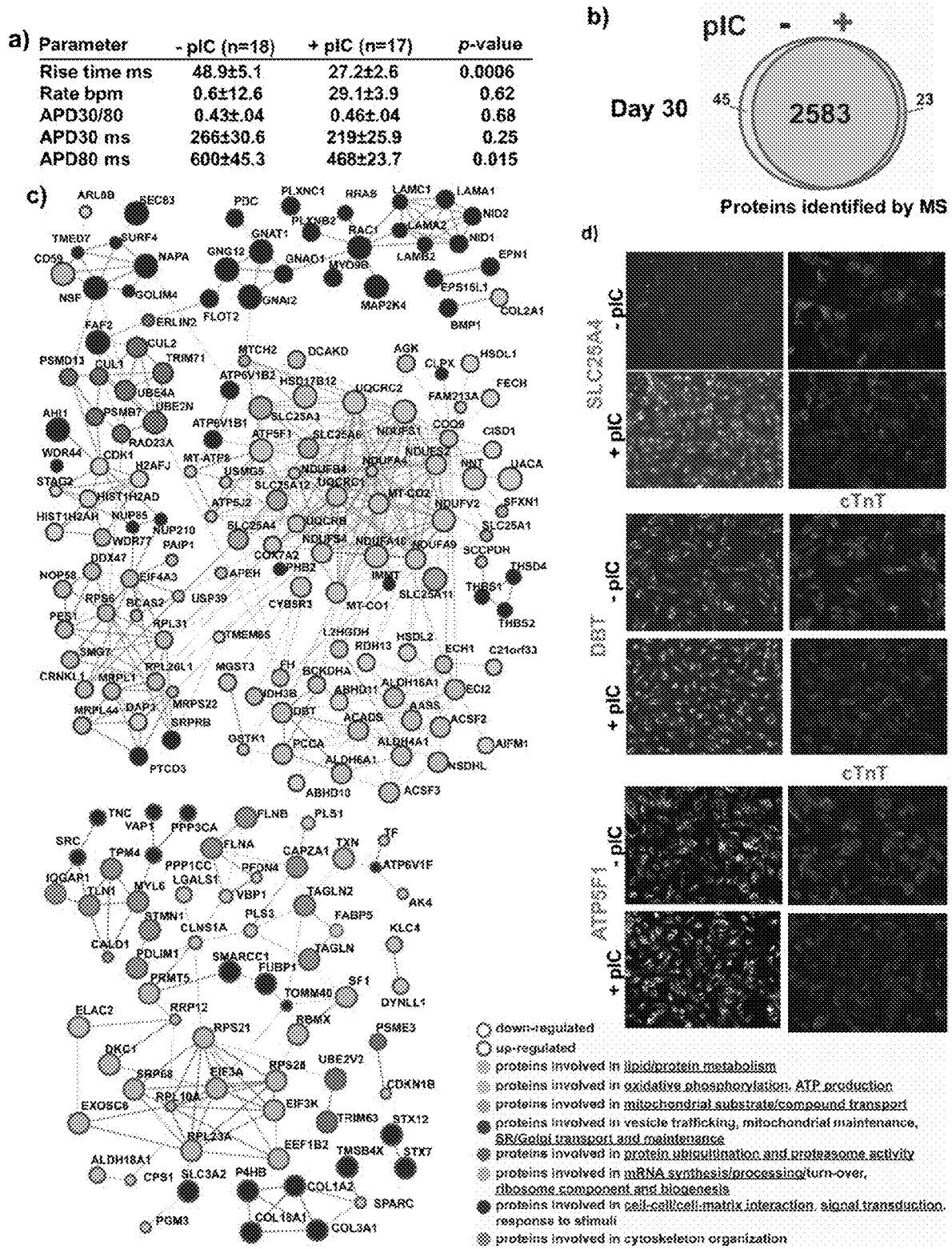
FIGS. 4A-4D—Electrophysiology and bottom-up proteomics characterization of hPSC-CMs from primed relative to untreated progenitors

In another aspect, provided herein are conductive microtissues and methods of producing the same in vitro. In some cases, a conductive microtissue is produced in vitro from developmentally mature cardiomyocytes obtained according to the methods provided herein. Conductive microtissue obtained according to the methods of this disclosure are in some instances referred to as ventricular conduction microtissue. In certain embodiments, dissociated and replated primed progenitors will self-organize into sheets of densely packed cTnT+ cardiomyocytes. The primed CPC-derived sheets are thicker and denser than the porous sheets of patchy aggregations of cardiomyocytes formed by untreated cardiac progenitors. As shown in FIG. 4B, primed progenitors yielded 4-fold more cardiomyocytes when replated at high cell density and 6-fold at lower cell density. As described in the Examples, the inventors determined that pI:C treatment produces networks of conduction system cells exhibiting more rapid conduction as compared to the surrounding cardiomyocytes. It was also determined that cardiomyocyte sheets obtained from primed cardiac progenitors exhibit a different pattern of contraction than the standard (non-replated) GiWi protocol with or without pI:C treatment. In this manner, trabeculation and conduction system formation following activation of innate immunity enable organized wave propagation comparable to ventricular conduction observed in vivo. Without wishing to be bound by any particular theory or mechanism of action, it is believed that dissociation and replating initiates a self-organizing process mimicking trabeculation and conduction system formation (i.e., the formation of trabeculae for development of internal structure of the ventricle for efficient conduction and contraction) which occurs during development of the embryonic heart.

In certain embodiments, a method of producing a conductive microtissue comprises dissociating a population of primed cardiac progenitors cells (CPCs), and replating the dissociated primed CPCs onto a solid substrate. In some cases, the method can further comprise a first step of obtaining primed CPCs according to the methods provided herein. In some cases, the primed CPCs are "day 5" progenitors, meaning they are collected by dissociation on day 5 of the differentiation protocols provided herein. In certain embodiments, dissociation comprises contacting the primed progenitors with a cell dissociation reagent such as Versene (Thermo Fisher Scientific), pipetting the contacted cells up and down to break up any aggregates, and resuspending the cells in a suitable culture medium for replating.

Dissociated cells can be replated at a cell density between about 0.5 million cells/plate to about 2.0 million cells/plate. In some cases, the cells are replated in a culture medium containing a ROCK inhibitor (e.g., Y-27632). In some cases, the solid substrate is a coated (e.g., recombinant vitronectin, Synthemax®-coated or coated by another matrix or protein solution) or uncoated tissue culture plate or dish. Differentiating CMs from replated primed cardiac progenitors will spontaneously beat by about 8 to about 15 days (e.g., about 8 days, 9 days, 10 days, 11 days, 12 days, 13 days, 14 days, 15 days) post-replating.

Following dissociation and replating, primed CPCs cells will self-organize and differentiate into sheets of primed cardiac progenitor-derived cardiomyocytes, where the primed progenitor-derived microtissues exhibit increased conduction velocity as compared to microtissues obtained using untreated/unprimed CPCs, which exhibit multifocal or reentrant conduction circuits (meaning, an abnormal or impaired conduction circuit) rather than the organized conduction patterns observed in the ventricular conductive microtissues provided herein. The primed progenitor-derived conductive microtissues also exhibit differentiation resembling trabeculation of embryonic cardiac muscle with increased Jag1 expression as well as the genesis of ventricular conduction system-like HCN4$^+$ cells. In particular, conductive microtissues (also known as ventricular conduction microtissues) generated from dissociated pI:C-primed progenitors exhibit organized conduction patterns with faster conduction in areas comprising ventricular conduction system-like cells as identified using a conduction cell surface marker such as HCN4 (hyperpolarization-activated cyclic nucleotide-gated channel) and Fluo-4 (a intracellular fluorescent dye to measure calcium levels) using optical mapping.

In certain embodiments, dissociation and replating of primed cardiac progenitors is performed under chemically defined conditions, thereby producing a chemically defined conductive microtissue. For example, in some embodiments dissociated cells are replated onto a substrate (e.g., tissue culture plate) coated with a chemically defined material such as recombinant human vitronectin or a defined synthetic coating such as Synthemax®. Differentiation of hPS cells into populations of cells comprising primed cardiac progenitors or developmentally mature cardiomyocytes under completely chemically defined conditions is particularly advantageous to facilitate translation of these cells to regenerative therapies or other clinical applications. By comparison, most, if not all, existing differentiation protocols require expression of transcription factors, integration of cardiac specific promoter driven selection cassettes, or application of serum and/or growth factors.

As used herein, the terms "chemically defined conditions" and "fully-defined conditions" indicate that the identity and quantity of all culture medium components and factors used in the differentiation protocol are known and the identity and quantity of a supportive surface is known. Likewise, the terms "defined culture medium," "defined medium," and the like, as used herein, indicate that the identity and quantity of each medium ingredient is known. A defined medium may also include solely constituents having known chemical compositions. A defined medium may further include constituents derived from known sources. Typically, serum that is normally added to culture medium for cell culture is replaced by known quantities of serum components, such as, e.g., albumin, insulin, transferrin and possibly specific growth factors (i.e., basis fibroblast growth factor, transforming growth factor or platelet-derived growth factor). Defined medium (DM) is therefore serum-free. As used herein, "serum-free" means that a medium does not contain serum, or that it contains essentially no serum. As used herein, "essentially" means a de minimus or reduced amount (i.e., less than 5%) of a component, such as serum, may be present.

In another aspect, provided herein is a population of HCN4$^+$ ventricular conduction system-like cells derived from primed cardiac progenitors according to the methods provided herein.

In another aspect, the materials described above as well as other materials can be packaged together in any suitable combination as a kit useful for performing, or aiding in the performance of, method provided herein. It is useful if the kit components in a given kit are designed and adapted for use together in the disclosed method. For example disclosed are kits comprising, for example, primed cardiac progenitors, developmentally mature cardiomyocytes, or a conductive microtissue produced by the disclosed methods. As another example, disclosed are kits comprising one or more TLR-3 ligands for priming of pluripotent stem cell-derived cardiac progenitors. In some embodiments, kits also can contain labels and other reagents for detection of biological markers, polypeptides, or nucleic acids. In certain embodiments, a kit for making a conductive microtissue in vitro comprises a coated cell culture substrate; an activator of innate immunity; a cell culture medium; and a cell dissociating solution.

As used herein, "about" means within 5% of a stated concentration range or within 5% of a stated time frame.

As used herein, "effective amount" means an amount of an agent sufficient to evoke a specified cellular effect according to the present invention.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

The assays and results described in this section demonstrate that priming of cardiac progenitors with polyinosinc cytidilic acid (pI:C) stimulates proliferation and leads to hPSC-CMs with accelerated maturation. This section also demonstrates that dissociated, primed progenitors formed ventricular conduction microtissue with highly organized patterns of excitation, and that primed cardiac progenitors improved survival when transplanted in mice after myocardial infarction relative to mice receiving untreated cardiac progenitors. Thus, early interventions on cardiac progenitors can accelerate maturation, promote tissue organization, and enhance therapy.

Methods

Cell Culture

Pluripotent cell lines used in this study were the hESC line H9 with a lentiviral cTnT-GFP reporter (H9 cTnT-GFP) (Wrighton et al., 2014 PNAS 111:18126) and the iPS cell line DF19-9-11 (Yu et al., 2009). Both lines were maintained and passaged as previously described in E8 media (Chen et al., 2011) on stem-cell verified Matrigel® (WiCell).

To differentiate cardiomyocytes from hPSCs, the small molecule temporal modulation of the Wnt pathway (GiWi) monolayer protocol was used essentially as previously described (Lian et al., 2012). Human embryonic or induced pluripotent stem cells were dissociated with Versene (Thermo Fisher Scientific) for 6 minutes at 37° C., pipetted up and down 40 times, counted with a hemocytometer, spun down at 100×g for 5 minutes, and resuspended and seeded for differentiation at 1.5 million cells per well in 6 well plates or 0.4 million per well in 12 well plates in mTeSR® on stem-cell verified Matrigel® (WiCell) containing 10 μM Y-27632 ROCK-inhibitor (Tocris). After four days in mTeSR® (WiCell), at which point cells grew to 100 percent confluence, medium was switched to RPMI supplemented with B27 supplement not containing insulin (Thermo Fisher Scientific) and containing 12 µM of the Wnt agonist CHIR99021 (Tocris) for exactly 24 hours. Media was then changed to RPMI supplemented with B27 not containing insulin for exactly 48 hours. Then medium was then switched at day 3 to RPMI supplemented with B27 not containing insulin and containing 5 µM IWP2 (Tocris). At day 5, media was switched to RPMI supplemented with B27 not containing insulin for two days. At day 7 and every three days afterward, medium was replaced with RPMI supplemented with B27 containing insulin (Thermo Fisher Scientific). Cardiomyocytes begin to beat at day 8-15 in the protocol. For the creation of day 5 primed progenitors, polyinosinic-cytidilic acid (pI:C, Sigma) was added at a dose of 95 µg/cm$^2$ per well at day 3 of differentiation (along with IWP2 in the cardiac mesoderm stage of the protocol). 500 nM DAPT (Abcam) was added at indicated time ranges only during days with routine medium changes in the differentiation protocol.

For dissociation of day 5 cells (for destructive analyses or live cell replating experiments), progenitors were dissociated with Versene (Thermo Fisher Scientific) for 10 minutes at 37° C., pipetted up and down 40 times, and then neutralized 1:1 v/v versene solution with "K20" medium (DMEM/F12 with 1×NEAA, 1× Glutamine, 0.1 mM (3-mercaptoethanol, and 20% Knockout Serum Replacer by volume, all Thermo Fisher Scientific). For destructive analyses, pellets were made by centrifugation at 1.1×1000 g for 5 minutes, aspiration of medium supernatant, snap-freezing in liquid nitrogen, and kept at –80° C. for until pellet lysis for DNA, protein, or RNA isolation.

For replating of progenitors and microtissue formation, after neutralization and cell counting, 0.8 million day-5 progenitors per well were spun down at 100×g as above and resuspended and plated in 1 mL K20 with 10 µM Y-27632 ROCK-inhibitor (Tocris) into Synthemax® II-SC coated 12 well plates (Corning). Media was then changed daily in 2 mL of "K2" (same formulation as K20 above, but with just 2% Knockout Serum Replacer), and changed daily. Differentiating hPSC-CMs from replated progenitors in this protocol beat by day 8 to 12.

hPSC-CMs were dissociated as described for progenitors above except that undiluted 10× TrypLE was used for 20 minutes. For immunofluorescence, action potential measurement, or metabolic assessment, cardiomyocytes were similarly replated in K20 with 10 µM Y-27632 ROCK-inhibitor (Tocris) (and media changed the next day and every other day after to K2) in Synthemax®-coated plates or coverslips.

Immunofluorescent Staining

For internal antigens, cells were rinsed of media two times in PBS, fixed for 10 minutes in 4% paraformaldehyde at RT, rinsed three times again in PBS, then blocked for 1 hour at room temperature (RT) in Licor blocking buffer containing 0.2% Triton x-100 (Sigma). Blocking solution was aspirated and antibodies added overnight at 4° C. in fresh blocking/permeabilization solution. Antibodies used were mouse cardiac troponin T (Thermo Fisher Scientific, 1:200), rabbit WT1 (Abcam 1:200), mouse smooth muscle myosin heavy chain (Abcam, 1:200), goat Jag1 c-terminal domain (1:200 Abcam), MMP1 (Abcam, 1:200), mouse cardiac actin (Sigma, 1:200), rabbit SLC25A4 (Proteintech, 1:100), rabbit DBT (Proteintech, 1:100), rabbit ATP5F1 (Proteintech, 1:100), rabbit Irx4 (Abcam, 1:200), goat nkx2.5 (Santa Cruz, 1:50), mouse connexin 40 (Thermo Fisher Scientific, 1:200), and fibroblast-specific protein (Abcam, 1:100). After primary and secondary antibodies, cells were rinsed two times in PBS with 0.2% triton x-100. Donkey secondaries conjugated to Alexa Fluor dyes were used at 1:1000 and incubated at RT for 1 h. DAPI or Hoechst was used to visualize nuclei. Cells were imaged either on an EVOS system in wells (Thermo Fisher Scientific) or a Leica confocal microscope in cover glass or ibidi 8-well microslides. Image J was used to quantify cell area by outer boundaries of cTnT staining.

For live cell immunostaining of ventricular conduction microtissue formed from cardiac progenitors, HCN4 (rabbit, 1:200, Millipore) antibody was incubated in warm K2 medium on live cells of the H9 cTnT-GFP (FIG. 5) or 19-9-11 iPS cell lines for 20 minutes at 37° C., rinsed two times with warm K2, and then incubated in 1:1000 secondary detection agents (donkey anti-rabbit AF647, Thermo Fisher Scientific) in K2 medium. After rinsing twice again, cells were visualized in an EVOS microscope equipped with GFP or Cy5 light cube sets (Thermo Fisher Scientific).

All live cell GFP images (FIGS. 8A, 8B) were obtained with hPSC-CMs from the H9 cTnT-GFP reporter cell line.

Electron Microscopy

Differentiated H9-cTnT-GFP line hPSC-CMs at day 30 were washed twice with sodium phosphate buffer and fixed and maintained in sodium phosphate buffer with 4% paraformaldehyde (PFA) until pelleting and processing for TEM as previously described (Raval et al., 2015).

Flow Cytometry

Flow cytometry for internal antigens was done on dissociated cells using the same blocking, washing, secondary antibodies, and buffers as internal antigen immunofluorescence described above using mlc2v (proteintech, 1:100) and cardiac troponin T (Thermo Fisher Scientific, 1:200) in the 19-9-11 iPS cell line. Between washes and staining steps, dissociated cells were pelleted at 1,100 g for 5 minutes. Blocking and antibody staining steps were done in a volume of 100 µL, and washing steps in 1 mL in Eppendorf™ tubes.

Flow cytometry for live cell surface antigens was done on dissociated cells of the 19-9-11 iPS cell line with Thy1 biotin (1:200 Biolegend, with Life Technologies streptavidin direct conjugate at 1:1000) and SIRPα (1:200, Biolegend) in K20 and then analyzed at the UWCCC Flow Cytometry Laboratory using a BD LSRII Fortessa flow cytometer. For progenitor flow experiments, cells were dissociated as above for progenitor dissociation, centrifuged at 200×g, subjected to FACS to concentrate cells, and resuspended in 100 µL, of K2 media+rockI/Jag1 PE, BD Biosciences (1:20); Notch2 APC R&D Biosystems (1:10) and analyzed on either a BD FACSariaII cell sorter or BD LSRII Fortessa flow cytometer.

Propidium iodide staining was performed on ethanol-fixed cells of the 19-9-11 iPS cell line with a low flow rate and linear mode fluorescence according to a previously published protocol (Darzynkiewicz and Juan, 2001).

Top-Down Myofilament Isoform Measurement

Freshly isolated CMs from the H9-cTnT-GFP (FIG. 1) or 19-9-11 (FIG. 2) hPSC cell lines were washed with Ca$^{2+}$-free DPBS and centrifuged at 1,100 g for 5 minutes (min) and the wash solvent was removed. The cells were first homogenized in 50 µl HEPES solution (25 mM HEPES, pH 7.4, 2.5 mM EDTA, 100 mM NaF, 1 mM DTT, 10 mM L-methionine, 1 mM PMSF, 1 mM Na$_3$VO$_4$, protease inhibitor (Abcam) and phosphatase inhibitors). The homogenates were centrifuged at 17,000 g for 20 min and the HEPES extract containing predominately cytosolic proteins was collected. The remaining pellets were homogenized in 40 µl trifluoroacetic acid (TFA) solution (1% TFA, 5 mM tris(2-carboxyethyl)phosphine, 5 mM L-methionine) and centrifuged at 17,000 g for 20 min. The TFA extract containing predominantly the sarcomeric proteins was collected. Bradford protein assays were performed to determine the protein concentration. The sarcomeric protein-enriched extracts were diluted to 100 ng/µl for Liquid chromatography (LC)-MS analysis.

500 ng of each sarcomeric protein-enriched extract was injected to a home-packed reverse phase chromatography (RPC) column (PLRP-S, 10 µm particle size, 1000 A pore size, 500 µm inner diameter, 25 cm long), and the proteins were separated with a gradient of 5-95% mobile phase B (0.1% formic acid in 50:50 acetonitrile:ethanol) (mobile phase A: 0.1% formic acid in $H_2O$) at a constant flowrate of 12 µl/min. The eluting proteins were analyzed by a high-resolution quadrupole-time of flight (q-TOF) mass spectrometer (Impact II, Bruker Daltonics) via electrospray ionization. The mass spectra were collected at a scan rate of 0.5 Hz for all samples being analyzed. Analyses of top-down mass spectra were performed using the vender-specific software DataAnalysis 3.2 (Bruker Daltonics).

Quantification of the sarcomeric protein isoforms was performed as previously described. (Gregorich et al., 2017) Briefly, for a specific protein isoform, the most abundant 3-5 charge state ions that do not overlap with other ions were selected for generating extracted ion chromatogram (EIC). The area under curve (AUC) of the EIC of a specific protein isoform represents the abundance of the selected protein isoform. The protein abundance was further adjusted to account for oxidation and other modifications of the same protein. The same ions were selected for the same protein isoform across all samples to be compared. Relative quantification of protein isoform expression was measured by the ratio of the AUCs.

Seahorse Bioanalyzer Oxidation Consumption Rate Measurements

After hPSC-CM dissociation of day 40-70 lactate-purified hPSC-CMs from the H9 cTnT-GFP reporter cell line, 25,000 cells per well were replated into Synthemax®-coated wells of Seahorse XF96 V3 PS cell culture plates (Agilent). Plates were analyzed for basal and maximal oxygen consumption rate with a Seahorse XF cell mito stress kit according to the manufacturer's instructions (Agilent) using concentrations of 1 µM oligomycin, 2 µM FCCP, and 0.5 µM Rotenone/antimycin A. Purity was determined by dissociating seahorse wells after analysis and doing live cell flow cytometry for cTnT-GFP. To directly compare data between plate runs/biological replicates, the fold change between hPSC-CMs from pI:C− and pI:C+ progenitors was computed for each sample's maximal and basal oxygen consumption rate normalized to total protein estimated after cell lysis in EBC buffer. $Log_2$ of the fold changes was tested for significance in a one-sample t test against a null hypothesis of 0.

Optical Action Potential Measurement

After hPSC-CM dissociation, day 30 to 60 lactate-purified hPSC-CMs from the 19-9-11 cell line were plated as 80 µL drops on areas of cover glass previously coated in drops of Synthemax® working solution of 80 µL (Corning) in the K20/2 dissociation and replating technique described above. After at least two days in K2 medium, the fast-equilibrating voltage-sensitive dye RH237 at 1 µM was added and live cells imaged in the cover glass in a Leica confocal microscope. Video files of individual cells were taken and filtered with the 50th FIR filter at a cutoff frequency of 128 Hz. The resulting action potentials were analyzed for rise time and voltage velocity in MATLAB. Individual cells were considered as replicates for statistical purposes and came from 4 cell preparations.

Bottom-Up Proteomics

Frozen CM pellets from day 30 in the H9 cTnT-GFP reporter cell line with or without pI:C treatment were washed with $Ca^{2+}$-free DPBS and centrifuged at 10,000 g for 10 min and the wash solvent was removed. 10 µl of 4 M urea, 0.5 M ammonium bicarbonate, 1 mM DTT, 10 mM L-methionine was added to the each pellet, and the pellets were vortexed and sonicated for 5 min, followed by incubation with shaking at 50° C. for 10 min. ProteaseMax™ surfactant was added to a final concentration of 0.04% and the pellets were vortexed and incubated at 37° C. for 10 min. 30 µl of water was added to the pellets, and the pellets were incubated at 80° C. for 20 min. After centrifugation at 16,000 g for 10 min, the supernatant was collected for Bradford assay to determine protein concentration. All samples were diluted to 800 ng/µl using 1 M urea and 125 mM ammonium bicarbonate, and 50 µl of the extract was reduced with 10 mM DTT for 30 min at 37° C., followed by alkylation with 25 mM Iodoacetamide for 30 min at room temperature in dark. The pH of the samples were tested to make sure the pH was between 7-8 and Trypsin Gold (Promega®) was added to a final trypsin to substrate ratio of 1:50 and incubated at 37° C. for overnight (16 hrs). Acetic acid was added to a final concentration of 5% (pH~3) and the samples were centrifuged at 16,000 g for 30 min prior to LC-MS analysis.

Label-free quantitative proteomics analysis was performed using a high-resolution q-TOF mass spectrometer (Impact II, Bruker Daltonics). 3.6 µg of the protein digest were injected to a C18 (New Objective) trapping column for desalting at a flow rate of 8 it/min for 5 minutes. The peptides were separated on a 250 mm PicoFrit capillary column packed with 1.9 µm, 175 A Hypersil Gold aQ C18 particles (New Objective) at a flow rate of 300 nl/min by a gradient of 5-45% mobile phase B (0.1% formic acid in acetonitrile) (mobile phase A: 0.1% formic acid in water). The capillary column tip was customized to fit into the CaptiveSpray nanoESI source (Bruker Daltonics) for direct delivery of samples to the mass spectrometer. The most abundant 30 ions were selected for fragmentation by tandem MS (MS/MS) with an active (dynamic) exclusion time of 45 sec. The control group with and without pI:C treatment were analyzed with 5 and 6, respectively, biological replicates. Each sample was analyzed with 3 injection replicates. Protein identification and quantification were performed using the MaxQuant v1.5.7. Proteins were considered identified when at least 1 unique peptide was identified in at least 2 of the biological replicates. Label-free protein quantification was performed by first normalizing the intensity of the proteins (measured by both unique and razer peptides) to the median intensity of the same dataset, and the maximum and minimum of all the non-zero values (if more than 5 values are non-zero) were removed prior to averaging the datasets from the same group. The Welch's modified t-test was performed to evaluate the statistical significance of variation and the protein abundance was considered significantly different when the p value was less than 0.01. Protein-protein interaction analysis was performed using the STRING database.

RNA Isolation and Reverse-Transcription Quantitative Polymerase Chain Reaction (RT-qPCR) for Gene Expression Analysis Frozen cell pellets from progenitors or cardiomyocytes in the 19-9-11 iPS cell line were thawed and RNA isolated using RNeasy spin columns with on-column DNase treatment according to the manufacturer's instructions (Qiagen). 500 ng of isolated RNA was used as template for reverse transcription using Biorad iScript RT supermix according to the manufacturer's instructions. 2.5 ng of derived cDNA was then used as template in qPCR with Taqman® primers bearing FAM-MGB dyes for genes of interest in a 20 µL reaction with Taqman® universal PCR supermix and the manufacturer's recommended cycling conditions (Thermo Fisher Scientific).

RNAseq

Day-5 cells from d3-5 untreated, TGFβ-treated, and pI:C-treated progenitors from the 19-9-11 iPS cell line were separately prepared as above for cell dissociation of progenitors from three different wells of each condition (for 9 total sequencing samples) and isolated as described above for RNA for RT-qPCR. rRNA-reduced Illumina TruSeq™ Stranded total RNA libraries were prepared and 1×100 bp single end sequencing was performed. To map and annotate RNA-seg data, STAR and HTSeq were used, respectively (Anders et al., 2015; Dobin and Gingeras, 2015). Annotated transcript counts were further processed with DeSEq2 for differential gene expression analysis (Love et al., 2014). Gene neighborhood analysis was performed with NEST (Jiang et al., 2015). Top upregulated and downregulated genes are presented in Tables 3-6.

Immunofluorescence on Whole-Mount Embryos

Mice were treated in accordance with Public Law 99-158 as enforced by the University of Wisconsin-Madison. For the collection of staged embryos, timed matings between the B6CBAF1/J inbred hybrid strain (Jackson Laboratory, Bar Harbor, Me.) and embryo dissections were carried out as previously described (Lalit et al., 2017). Immunofluorescence was as previously described (Downs, 2008; Mikedis and Downs, 2013). The following antibody sources, stock concentrations, and dilutions were: Jag1 C-terminal domain (ab192767, Abcam, Cambridge, Mass.; 0.5 mg/ml, goat polyclonal; 1/50-100 dilution), Dylight 550 donkey anti-goat (ab96932, Abcam; 0.5 mg/ml; 1/100 dilution). After 15 minutes of incubation at room temperature with DAPI (D1306, Life Technologies, Fitchburg, Wis.; stock 5 mg/ml; 1/830 dilution) and subsequent washes in blocking solution (phosphate-buffered saline (Sigma-Aldrich, St. Louis, Mo.) containing 5% donkey serum (EMD Millipore, Billerica, Mass.) and 0.1% Triton-X; Downs, 2008), the anterior region of each embryo was bisected from the posterior region with forceps and transferred into a drop of Aqua-Mount (13800, Lerner Laboratories) that was centrally placed on a chrome-alum gelatin-subbed glass slide. Once the desired frontal orientation (anterior up) was achieved, a No. 1.5 cover glass was gently applied over the tissue, and the slides were allowed to set overnight in the dark at 4° C. Within 3 days of mounting, fluorescent images were collected with a Nikon A1R+ confocal microscope (W. M, Keck Laboratory for Biological Imaging, UW-Madison) using the CFI Plan Apo Lambda 20× and 60× (oil) objectives, a pinhole size of 1.2 AU, and lasers at 403, 488, 560 nm.

Western Blotting for Protein Expression Analysis

Frozen cell pellets from cardiac progenitors in the 19-9-11 iPS cell line were thawed and protein isolated in EBC lysis buffer (Boston BioProducts) supplemented with complete protease inhibitor tablets (Roche) rocking on ice for 1 hour to cause cell lysis. After the observation of lysis material and cell debris, protein/debris mixtures were centrifuged at >18,000×g for 15 minutes at 4° C. The protein-containing supernatant was quantified in a plate reader using the Biorad DC protein assay. 40 to 80 µg of protein was loaded in 6× βmercaptoethanol-containing Laemmli sample buffer (Biorad), boiled for 10 minutes at 95° C., then run on a 4-20% Criterion™ TGX™ gel (Biorad) for 30 minutes at 200 V. Proteins were then transferred at 10 V overnight at 4° C. to Immobilon-FL™ PVDF in a Criterion™ plate transfer cassette in Tris-Glycine transfer buffer (Biorad) with 20% methanol. Membranes were blocked for 1 hour at RT in Licor PBS blocking buffer, and then incubated with primary antibodies overnight 4° C. Antibodies were used at a dilution of 1:1000 (goat anti-Jag1, R&D systems) or 1:3000 (GAPDH, sigma) in Licor PBS blocking buffer. After primary (and secondary) antibodies, membranes were washed in PBS with 0.1% tween-20 detergent (Sigma) three times for 10 minutes at RT. Licor secondary donkey anti-rabbit or anti-mouse antibodies were used at 1:15,000 for 1 hour at RT in Licor PBS blocking buffer, and after washing membranes were analyzed in a Licor Odyssey detection system.

Methylcellulose Colony-Forming Assay

Day-5 cardiac progenitors from the 19-9-11 cell line were dissociated as above, but then passed 10 times through a syringe with 18 gauge needle and filtered twice through a 45 µm flow cytometry cell strainer. The cells were then counted and 100,000 cells were then mixed with 2 mL of K20 medium plus 10 µM Y-27632 ROCK-inhibitor (Tocris) containing 1% ES-Cult methylcellulose (Stemcell Technologies) and grown in one 6-well of a corning Ultra Low Attachment plate. ImageJ was used to measure colony diameter four days later and single cells observed the first day and after had diameters less than 35 µm.

Video Edge Detection/Beating Analysis and Calcium Optical Mapping

For quantification of spatial regularity and graphical presentation of time averaged beating in microtissue from the H9-cTnT-GFP (FIGS. 9A, C) or 19-9-11 (FIG. 9B) cell lines, .avi video files of low-powered (2.5× magnification) fields were recorded at a resolution of 1268×720 and a frame rate of 20/second. These videos were exported into a series of sequential .tiff files using Adobe Premiere, and then analyzed in MATLAB using previously described coding algorithms (Huebsch et al., 2015). Calculations of beat rate (before and after ivrabradine, 5 µm for 2 hours, Sigma) were performed manually in the 19-9-11 cell line and multifocal patterns in untreated progenitor-derived sheets were represented as the average rate of beating for all foci present in a field.

For optical calcium mapping of cell sheets, sheets were stained with Rhod-2 AM (10 µmol/L, Abcam, Cambridge, Mass.) for 15 minutes at 37° C. The sheets were then washed out for 15 min before imaging at 37° C. Cells were excited by a constant-current, low-noise halogen lamp at 520±45 nm, and fluorescent signals were filtered through a bandpass filter of 588±15 nm before collection by a Ultima-L CMOS camera (SciMedia, Costa Mesa. Calif.) with high spatial (100 µm/pixel) and temporal resolution (1000 frame/second).

For HCN4-calcium double imaging of cell sheets, alter HCN4 staining (as described in the Immunofluorescent staining section) sheets were stained with Fluo-4 AM (10 µmol/L, Thermo-Fisher Scientific, Waltham, Mass.) for 15 min at 37° C. The sheets were then washed out for 15 minutes before imaging at 37° C. Imaging was applied using Nikon DIAPHOT 300 microscope system under a 10× objective. Cells were sequentially excited using Spectra X light Engine® (Lumencor, Beaverton, Oreg.) and fluorescent signals were collected through green and red light cube sets for calcium and HCN4 respectively.

Mouse Myocardial Infarction Studies

Animal protocols and usage was approved by the University of Wisconsin Research Animal Resource Center Animal Care and Use Committee. Age 8-week male C57BL/6J mice were subjected to myocardial infarction by fixed surgical ligation of the left coronary artery and subsequent intramyocardial injection of 100 µL of K20+10 µM Y-27632 ROCK-inhibitor (Tocris) at the border zone with 1.5 million cells for both pI:C treated and untreated CPC cell groups. Mice were examined by echocardiography at acute (2 days post-infarction) and pre-terminal (3 weeks post-infarction) time points. MIs were verified by day 2 echocardiography, and animals with absolute ejection fraction <40% were chosen for survival analysis. Cyclosporine (Abcam) at 15 mg/kg was given daily beginning the day before surgery and cell transplant.

Immunohistochemistry on Tissue Sections

Tissue was section at 5 µm thickness, mounted on charged slides, and then incubated in an 80° C. oven for 20 minutes to melt the paraffin. Deparaffinization was done in 3 changes of xylene, 5 minutes each. Sections were hydrated through graded ethanols to deionized water, then rinsed for 5 min. in $dH_2O$. Antigen retrieval occurred in Tris-EDTA buffer, pH 9.0 (10 mM Tris Base, 1 mM EDTA, 0.05% Tween® 20), for 3 minutes in a Biocare decloaker (Biocare Medical, Concord, Calif.). Slides were cooled for 30 min, rinsed with phosphate buffered saline (PBS), then blocked in 10% goat serum in PBS 1 hour at RT. Anti-Cardiac Troponin T at 1:200 (Abcam47003), rabbit SLC25A4 (Proteintech, 1:200), rabbit ATP5F1 (Proteintech, 1:200), goat anti-Jag1 (Abcam, 1:200), mouse anti-cardiac actin (Sigma, 1:75), anti-Aurora B Kinase 1:200 (Abcam2254), and mouse anti-human mitochondria at 1:1600 (Millipore, clone 113-1) in PBS with 1% goat serum overnight at 4° C. The next day sections were rinsed for 5 min. in PBS three times. Alexa Fluor 633 goat anti-rabbit (Invitrogen) and Alexa Fluor 568 goat anti-mouse in PBS, each at 1:1000 for 30 min at room temperature, in the dark. Sections were rinsed for 5 min in PBS three times, then rinsed in $dH_2O$ for 5 min. Sections were coverslipped with ProLong® Gold antifade reagent with DAPI (Invitrogen).

Statistics

Independent means of single pair experiments were compared using t tests and multi-group data with ANOVA first and then pairwise post-hoc comparisons having multiple comparison correction by the Holm method. Survival analysis was performed by a non-parametric log-rank test.

NF-κB Assays

Antibodies: NFKappaB (Abcam) and phosphorylated IKappaB (Abcam). Antibodies were used at a dilution of 1:1000. NF-κB inhibitor: 40 nM QNZ (Selleckchem). QNZ (EVP4593) shows potent inhibitory activity toward both NF-κB activation and TNF-α production.

Results pI:C Treatment of Cardiac Progenitors Accelerates hiPSC-CM Maturation

Figures 2A, 2B, 2C, 2D, 2E, 2F, 2G:
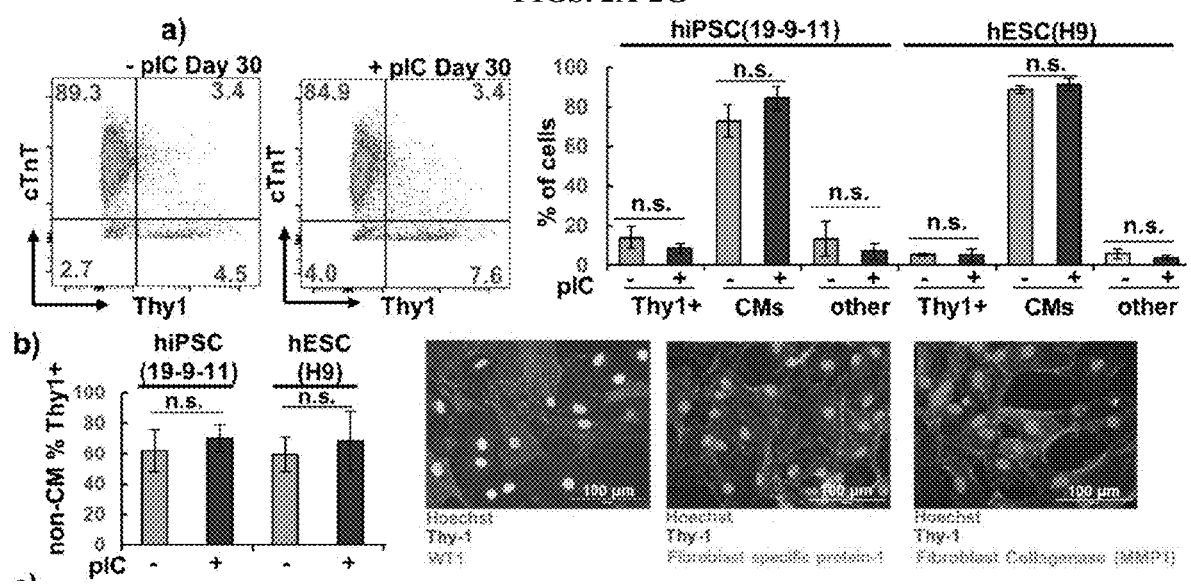
FIGS. 2A-2G—Cell lineages differentiated from cardiac progenitors cells are not changed by pI:C treatment FIG. 2A demonstrates flow cytometry quantification of Thy1$^+$ fibroblasts and hPSC-CMs identified by cTnT-GFP in the reporter H9 ES cell line or SIRPα (Dubois et al., 2011) in the 19-9-11 iPS cell line (Yu et al., 2009) from primed and untreated progenitors showing no significant change in the relative distribution of cell lineages.

In order to test the effect of pI:C on cardiac differentiation of hPSCs, we utilized a defined small molecule cardiac differentiation protocol based on activation of the Wnt pathway by GSK3β inhibition to generate cardiac progenitors followed by Wnt inhibition to promote differentiation of progenitors to hPSC-CMs (GiWi, FIG. 1A). pI:C was added during the progenitor stage of the GiWi protocol (day 3-5). Because prior studies utilized pI:C treatment to promote lineage reprogramming, we first assessed if pI:C treatment of cardiac progenitors altered the cell lineages present in the differentiated progeny. Flow cytometry revealed a comparable purity of cardiomyocytes marked by cardiac troponin T (cTnT) expression (80-95%) differentiated from pI:C-treated and untreated progenitors for both hES and hiPS cell lines (FIG. 2A). On average Thy1$^+$ cells accounted for the majority of non-cardiomyocytes differentiated from the progenitors which were primarily a fibroblast population supported by co-labeling with other markers of cardiac fibroblasts such as WT1, MMP1, FSP1 (FIG. 2B) (Witty et al., 2014). Other cell types were rare (FIG. 2C), and we detected no evidence for chamber-specific lineage changes in the mostly ventricular-fated GiWi cardiomyocytes (FIGS. 2D-2G).

We then assessed whether pI:C treatment of cardiac progenitors impacted the maturation of the resulting hPSC-CMs. Structurally, cardiomyocytes with greater maturity have larger size, longer, more organized sarcomeres, and higher expression of myofilaments found in adult ventricular heart such as cTnI, αMHC, and mlc2v (Kamakura et al., 2013; Kracklauer et al., 2013; Lian et al., 2012; O'Brien et al., 1993; Robertson et al., 2013; Tsuchimochi et al., 1986). Accordingly, day 30 hPSC-CMs from pI:C-treated progenitors were twice as large as untreated progenitors (FIG. 1B), and ultrastructural characterization by electron microscopy showed longer, more regular and compact sarcomeres that contained I-bands (FIG. 1C). A time course experiment of myofilament gene expression revealed that day 9 cells from treated progenitors had increased expression of all myofilament genes studied compared to untreated progenitor-derived cells, suggesting an earlier activation of the cardiomyogenic transcriptional program, and by day 30, these relative increases only remained for cTnI and αMHC, myofilament proteins with greater adult than fetal expression (FIG. 1D). The ventricular-specific myofilament protein mlc2v gradually increases its expression in ventricular-fated cardiomyocytes. Flow cytometry of day 30 cells demonstrated that pI:C treatment of cardiac progenitors markedly increased the percentage of mlc2v$^+$/cTnT$^+$ hPSC-CMs (FIG. 1E). The myofilament protein cTnT is expressed throughout development, but it undergoes developmental changes in protein splice forms based on the presence or absence of embryonic exon 5 (Wei and Jin, 2011), leading to initial expression of fetal isoforms 1 and 10 and subsequently adult isoforms 6 and 11 (Uniprot numbering). We performed top-down mass spectrometry to measure these isoforms of cTnT in hPSC-CMs and found that pI:C treatment of progenitors increased the ratio of adult to fetal isoforms in day 30 cardiomyocytes. During prolonged culture to day 122, the adult to fetal ratio and the relative difference between hPSC-CMs from pI:C treated and untreated progenitors increased dramatically (FIG. 1F). Together these data on hPSC-CM size and myofilament expression patterns indicate that pI:C treatment of cardiac progenitors accelerates cardiomyocyte differentiation and maturation.

Figures 3A, 3B, 3C, 3D, 3E, 3F, 3G:
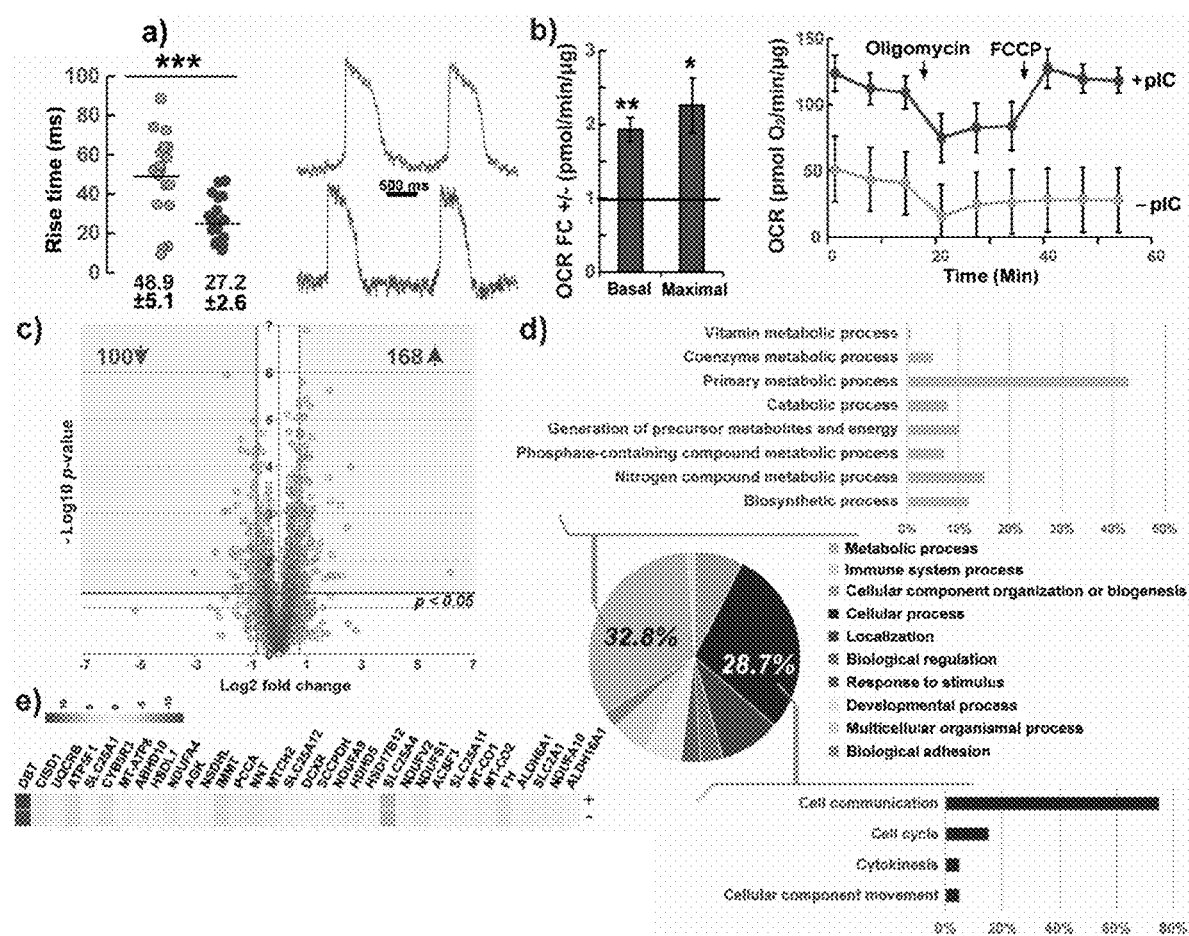
FIGS. 3A-3G—Functional and proteomic analysis of maturation in hPSC-CMs from primed and untreated cardiac progenitors FIG. 3A demonstrates optical upstroke velocity with the voltage-sensitive dye RH237 (quantified by time required to traverse 10 to 90% action potential amplitude, rise time) for hPSC-CMs from primed and untreated progenitors, individual cells plotted from 4 cell preparations.

We also assessed for functional changes in cardiomyocytes resulting from pI:C treatment of cardiac progenitors. For example, mature cardiomyocytes have faster action potential upstroke velocity and increased oxidative metabolism (Hom et al., 2011; Robertson et al., 2013). We recorded spontaneous optical action potentials from day 30 hPSC-CMs using the voltage-sensitive dye RH237. The optical upstroke velocity in hPSC-CMs from pI:C-treated progenitors was significantly faster (FIG. 3A, 4A), quantified as a decreased rise time (the time required to change from 10 to 90% depolarization voltage amplitude) (Lang et al., 2015). There was no difference in the spontaneous rate or other parameters measured for the spontaneous action potentials, except pI:C treatment did decrease APD80 (FIG. 4A). To examine the metabolism of hPSC-CMs, we lactate-purified (Tohyama et al., 2013) hPSC-CMs from both treated and untreated progenitors to high purity (95.9% and 96.1% respectively, n.s.) and used the Seahorse bioanalyzer to measure basal and maximal oxygen consumption in cardiomyocytes. We found that cardiomyocytes from treated progenitors had approximately 2-fold greater basal and maximal oxygen consumption rates (FIG. 3B).

To provide an unbiased assessment of hPSC-CMs from pI:C-treated progenitors relative to hPSC-CMs from untreated progenitors, we performed global label-free quantitative bottom-up proteomics (Yang et al., 2017). In day 30 hPSC-CMs, we detected about 2,600 proteins (FIG. 4B) and found that overall, 168 proteins were significantly upregulated and 100 downregulated in hPSC-CMs from treated relative to untreated progenitors ($p<0.05$ and $>50\%$ change in expression, FIG. 3C). The upregulated proteins were mainly involved in metabolic and cell communication processes (FIG. 3D). Inspection of upregulated metabolic proteins suggested predominant roles in oxidative phosphorylation, mitochondrial transport, and the metabolism of amino acids and lipids (FIGS. 3E-3F, 4C; see also Tables 1 and 2). This was consistent with our functional data showing increased oxygen consumption rates. By quantitative immunostaining, we verified increased expression of three of the top upregulated proteins in the dataset involved in oxidative metabolism: branched chain amino acid dehydrogenase (DBT), ATP synthase subunit (ATP5F1), and the cytoplasmic mitochondrial DNA-stabilizing ATP transporter SLC25A4 (FIG. 3G, 4D). SLC25A4 protein in particular was almost absent from untreated progenitor-derived cardiomyocytes and is a known mediator of mitochondrial function, where its loss in humans results in the mitochondrial myopathy MTDPS type 12 (Echaniz-Laguna et al., 2012). In contrast, down-regulated proteins were often involved in cytoskeletal organization (Myl6, Talin, Transgrelin, and collagens 18a1, 3a1, and 1a2, FIG. 4C). We found proteins involved in ribosomal biogenesis or mRNA synthesis and translation in both up and downregulated protein sets; however, we noticed mitochondrial ribosomal complex proteins MRPL1, MRPL44, and MRPS22 only among upregulated proteins in cardiomyocytes from pI:C-treated progenitors (FIG. 4C).

The combination of these proteomics data and the functional and molecular data support a model of increased metabolic, structural, and electrical maturation in cardiomyocytes from pI:C-treated progenitors, which we therefore refer to as primed cardiac progenitors.

TABLE 1

Top 50 upregulated proteins of cardiomyocytes from pIC-treated progenitors

| Protein | Fold change | P-value |
|---|---|---|
| DBT | 71.67984 | 0.018050159 |
| CISD1 | 6.04708 | 0.000101548 |
| UBE4A | 5.483937 | 0.001959543 |
| RAD54L2 | 4.857487 | 0.020880152 |
| HIST1H2AJ | 4.695769 | 0.000670072 |
| COL2A1 | 4.220905 | 0.020957835 |
| RRAS | 3.820307 | 0.007455635 |
| SMG7 | 3.816828 | 0.021416819 |
| EMC1 | 3.674222 | 0.020449554 |
| UQCRB | 3.664552 | 0.000543909 |
| ATP5F1 | 3.555673 | 2.39509E−06 |
| THBS1, THBS3, THBS2 | 3.482672 | 0.000172209 |
| CLPX | 3.1174 | 0.024294849 |
| ITM2B | 2.860622 | 0.00415839 |
| BMP1 | 2.713608 | 0.006206729 |
| CFC1, CFC1B | 2.610186 | 0.016113851 |
| EPN1 | 2.525022 | 0.008956677 |
| EPS15L1 | 2.414038 | 0.01764903 |
| MAP2K4 | 2.413647 | 0.008981985 |
| SLC25A1 | 2.332696 | 0.000791823 |
| CYB5R3 | 2.279164 | 2.36394E−05 |
| ORF1 | 2.257223 | 0.00542619 |
| NUP85 | 2.248992 | 0.000446959 |
| MT-ATP8 | 2.243951 | 0.003741969 |
| XPO7 | 2.230939 | 0.000834962 |
| AIFM1 | 2.223824 | 0.001342386 |
| ABHD10 | 2.204827 | 0.010809861 |
| TMEM65 | 2.197368 | 0.00425064 |
| SLC25A3 | 2.195133 | 5.30041E−06 |
| LNP | 2.18287 | 0.004288319 |
| HSDL1 | 2.135289 | 6.62748E−05 |
| NDUFA4 | 2.127875 | 5.28541E−05 |
| RAC1 | 2.127803 | 0.001035717 |
| MYO9B | 2.112032 | 0.025799434 |
| USMG5 | 2.084669 | 0.00020653 |
| AGK | 2.084198 | 0.000221757 |
| NSDHL | 2.081485 | 0.002751419 |
| IMMT | 2.058732 | 0.001757321 |
| PCCA | 2.031932 | 0.002609783 |
| LAMA1 | 2.030337 | 0.039428257 |
| ERLIN2 | 2.026234 | 0.001102923 |
| NNT | 1.994192 | 0.001276216 |
| MTCH2 | 1.989789 | 1.26269E−07 |
| MRPS22 | 1.975734 | 0.033856255 |
| ACSF2 | 1.970668 | 3.77188E−06 |
| SLC25A12 | 1.968303 | 0.011031697 |
| UACA | 1.95782 | 0.001885649 |
| CDK9 | 1.953732 | 0.022940211 |
| DCXR | 1.952299 | 0.023954972 |
| PHB2 | 1.952145 | 3.60139E−05 |

TABLE 2

Top 50 downregulated proteins of cardiomyocytes from pIC-treated progenitors

| Protein | Fold change | p-value |
|---|---|---|
| AK4 | 0.122028 | 0.018212 |
| AKAP12 | 0.210756 | 0.00666 |
| ALDH18A1 | 0.258988 | 0.00092 |
| ARL6IP1 | 0.271105 | 1.11E−06 |
| ATP6V1F | 0.283976 | 0.000883 |
| C5orf24 | 0.292699 | 0.0176 |
| CALD1 | 0.309899 | 0.006791 |
| CAPZA1 | 0.329169 | 0.03752 |
| CBWD1 | 0.334068 | 0.008065 |
| CDC37 | 0.334675 | 0.005686 |
| CDKN1B | 0.339312 | 0.021292 |
| CLNS1A | 0.349175 | 0.000341 |
| COL18A1 | 0.35409 | 0.021712 |
| COL1A2 | 0.355351 | 0.000678 |
| COL3A1 | 0.371901 | 0.035632 |
| CPS1 | 0.385735 | 0.044306 |
| CRLF3 | 0.394908 | 0.006722 |
| DKC1 | 0.396203 | 4.39E−05 |
| DSG2 | 0.39913 | 2.64E−05 |
| DYNLL1 | 0.407011 | 0.001469 |
| EDC4 | 0.411116 | 0.010488 |
| EEF1B2 | 0.416046 | 0.013386 |
| EIF3A | 0.423467 | 0.033911 |
| EIF3K | 0.433491 | 0.001352 |
| ELAC2 | 0.453933 | 4.96E−05 |
| EXOSC6 | 0.4623 | 0.015403 |
| FABP5 | 0.474884 | 0.002547 |
| FLNA | 0.475701 | 0.006168 |
| FLNB | 0.476711 | 0.001815 |
| FUBP1 | 0.483953 | 0.012095 |

TABLE 2-continued

Top 50 downregulated proteins of cardiomyocytes
from pIC-treated progenitors

| Protein | Fold change | p-value |
|---|---|---|
| H6PD | 0.484492 | 0.005193 |
| HEATR6 | 0.485749 | 0.000413 |
| HEBP2 | 0.486655 | 0.005458 |
| HMGCS1 | 0.500331 | 0.011316 |
| IQGAP1 | 0.508274 | 0.005037 |
| ISOC1 | 0.511352 | 0.029095 |
| KLC4 | 0.511873 | 0.039359 |
| KRT18, KRT35 | 0.51276 | 0.003513 |
| KRT19 | 0.521079 | 0.010492 |
| LGALS1 | 0.521109 | 0.001898 |
| LMCD1 | 0.522567 | 0.020459 |
| LRRC59 | 0.523499 | 0.022164 |
| MEST | 0.533347 | 0.006896 |
| MYL6 | 0.534037 | 0.000102 |
| NGLY1 | 0.53593 | 1.1E−05 |
| NIT2 | 0.543479 | 0.000278 |
| OGFR | 0.5517 | 0.007742 |
| P4HB | 0.553061 | 0.00011 |
| PDLIM1 | 0.55613 | 0.016318 |
| PDLIM3 | 0.55699 | 0.005988 | pI:C Augments Notch Signaling and Proliferation in Cardiac Progenitors

Figure 6:
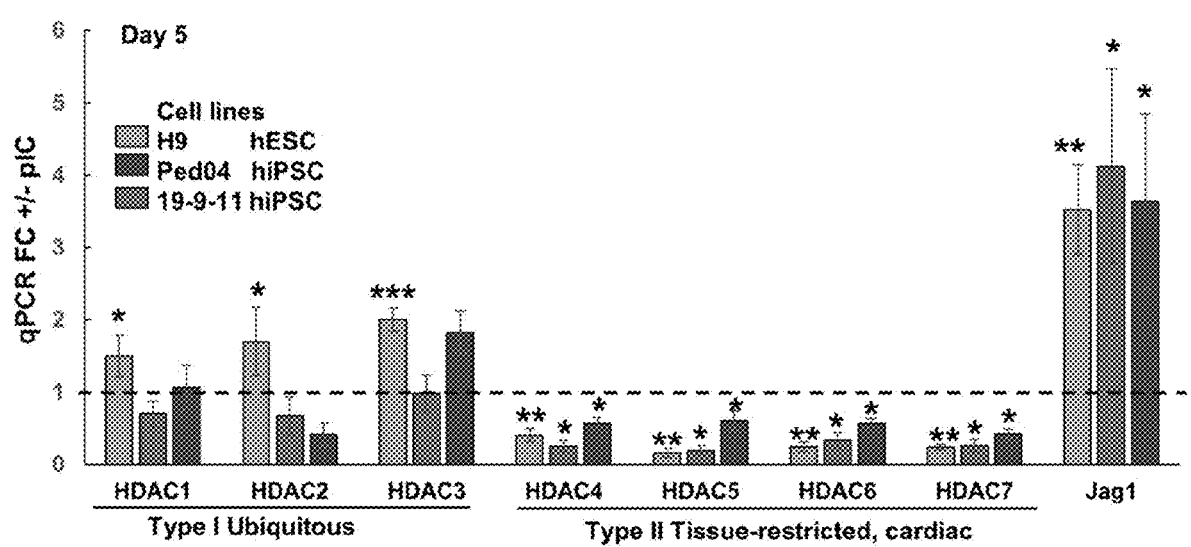
FIG. 6 demonstrates the effect of pI:C treatment of cardiac progenitors on expression of histone deacetylases and genes associated with innate immune system signaling. Images show expression of type I and type II HDACs in pI:C treated and untreated cardiac progenitors from three pluripotent cell lines as measured by RT-qPCR, n=3-4. t TestP*<0.05, <0.01, *<0.001.

We next aimed to understand the mechanisms underlying the effects of pI:C on cardiac progenitors. Previous investigation demonstrated that pI:C-mediated augmentation of fibroblast reprogramming to iPSCs is associated with decreased expression of repressive epigenetic modifiers, including type I and type II histone deacetylases, and this correlated with increased activating marks at the loci of pluripotency factors (Lee et al., 2012). So we examined the expression of type I and II histone deacetylases in cardiac progenitors differentiated from multiple hPSC lines. Interestingly, we found by qPCR that primed progenitors had universally lower levels of type II histone deacetylases (HDAC4-7), but unchanged to unregulated levels of type I HDAC1-3 (FIG. 6). Type I HDACs are ubiquitous enzymes generally present in all cell types, but type II HDACs are specific to a small range of tissues. The heart is the only organ to express all type II HDACs 4-7, and the loss of type II HDACs alone or in combination causes cardiac-specific phenotypes (Haberland et al., 2009; Song et al., 2006). We viewed predominant type II HDAC modulation in primed progenitors compared to the mixed type I and II repression of pI:C treatment in fibroblasts as a distinct cardiac progenitor epigenetic response.

Figures 5A, 5B, 5C, 5D, 5E, 5F, 5G, 5H:
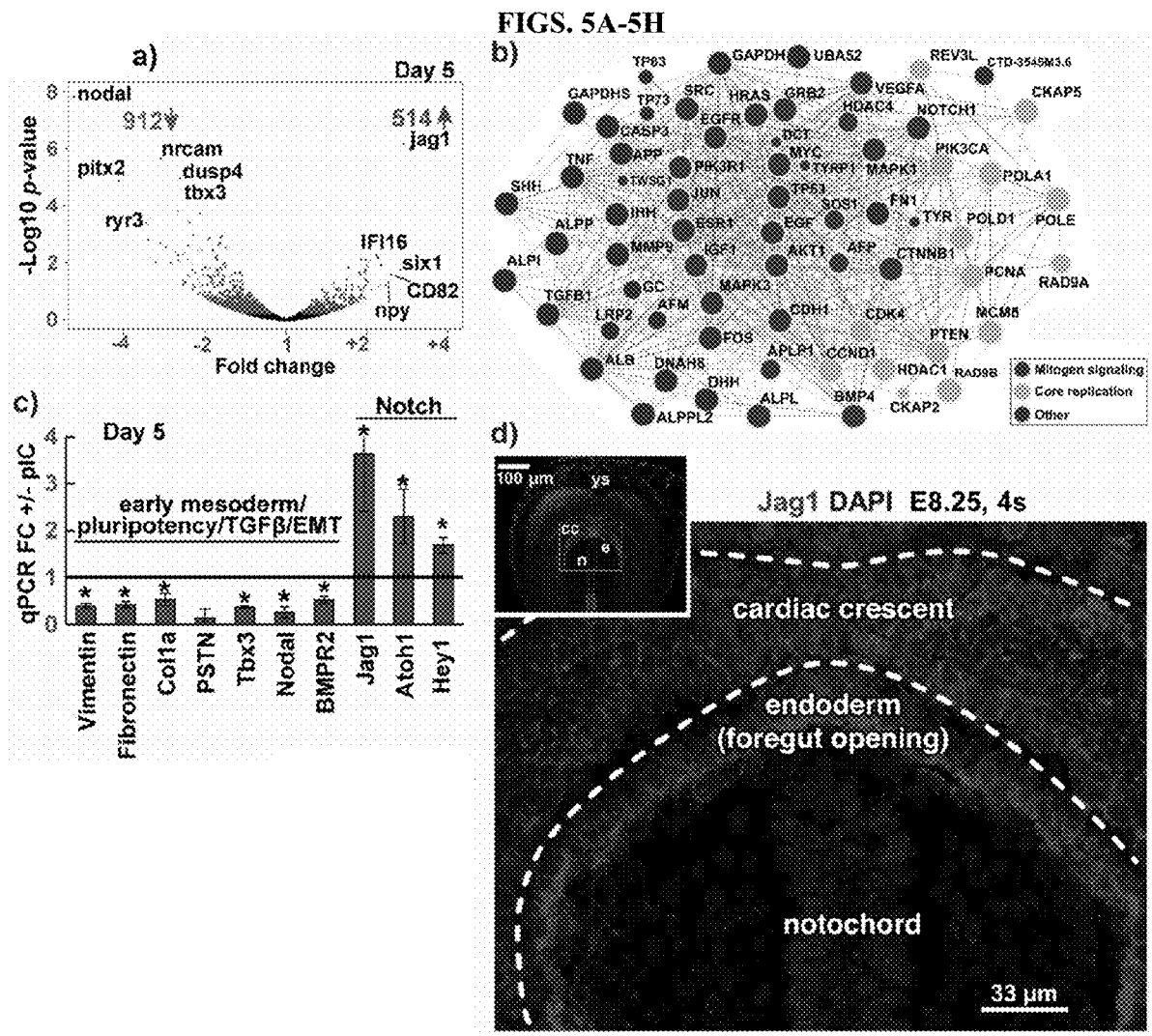
FIGS. 5A-5H—Transcriptomics of primed progenitors reveals TGFβ signaling downregulation and Notch signaling enrichment

To probe for changes in gene expression resulting from pI:C-induced epigenetic modifications of cardiac progenitors, we performed RNA-sequencing. pI:C had an aggregate net negative effect on gene transcription of day 5 progenitors with 912 genes significantly downregulated compared to 514 upregulated out of ~10,500 genes detected (FIG. 5A, Tables 3-6). Gene ontology analysis of pI:C downregulated genes showed TGFβ and pluripotency signaling as top downregulated GO terms (#3 and #4 by p-value in KEGG pathways analysis, Table 5), and we confirmed many of these genes by qPCR (FIG. 5C). We found that the downregulated TGFβ-related genes were either classical epithelial-to-mesenchymal transition (EMT) markers such as fibronectin and vimentin, or found in the GO analysis among "networks involved in pluripotency signaling" (#4 downregulated GO term, Table 5). Two of the top downregulated genes, tbx3 and nodal, are established necessary factors for pluripotency (Camus et al., 2006; Han et al., 2010). And TGFβ also mediates the EMT of primitive streak-like mesendoderm formation in the initial phase of cardiac differentiation protocols (Lian et al., 2012; Zhang et al., 2012). Thus, we interpreted pI:C's downregulation of TGFβ pathways as consistent with inhibiting the residual expression of genes of pluripotency and early EMT/mesendoderm.

pI:C upregulated genes were dominantly associated with cell proliferation in the gene ontology analysis (Tables 3 and 6), including DNA polymerases, DNA repair complexes, and histones. Gene family/neighborhood network interactome analysis (Jiang et al., 2015) equally suggested cell proliferation with multiple nodes for core DNA replication proteins (such as DNA polymerases, repair enzymes, and replication fork proteins) and classical proliferative signaling factors (such as MAP Kinase, Ras, Myc, and Notch, FIG. 5B). We noted that the top-enriched gene in RNA sequencing was the Notch pathway ligand Jag1 (FIG. 5A, Table 1), and qPCR validation of the RNAseq data confirmed upregulation of Jag1 and downstream Notch pathway genes (FIG. 5C). Loss of function mutations in human Jag1 and its receptor Notch2 result in cardiomyopathy in Alagille syndrome with ventricular septal defects and tetralogy of Fallot (Röpke et al., 2003). Thus, as suggested by network analysis, increased Jag1 may contribute to enhanced proliferation.

Figures 7A, 7B, 7C:
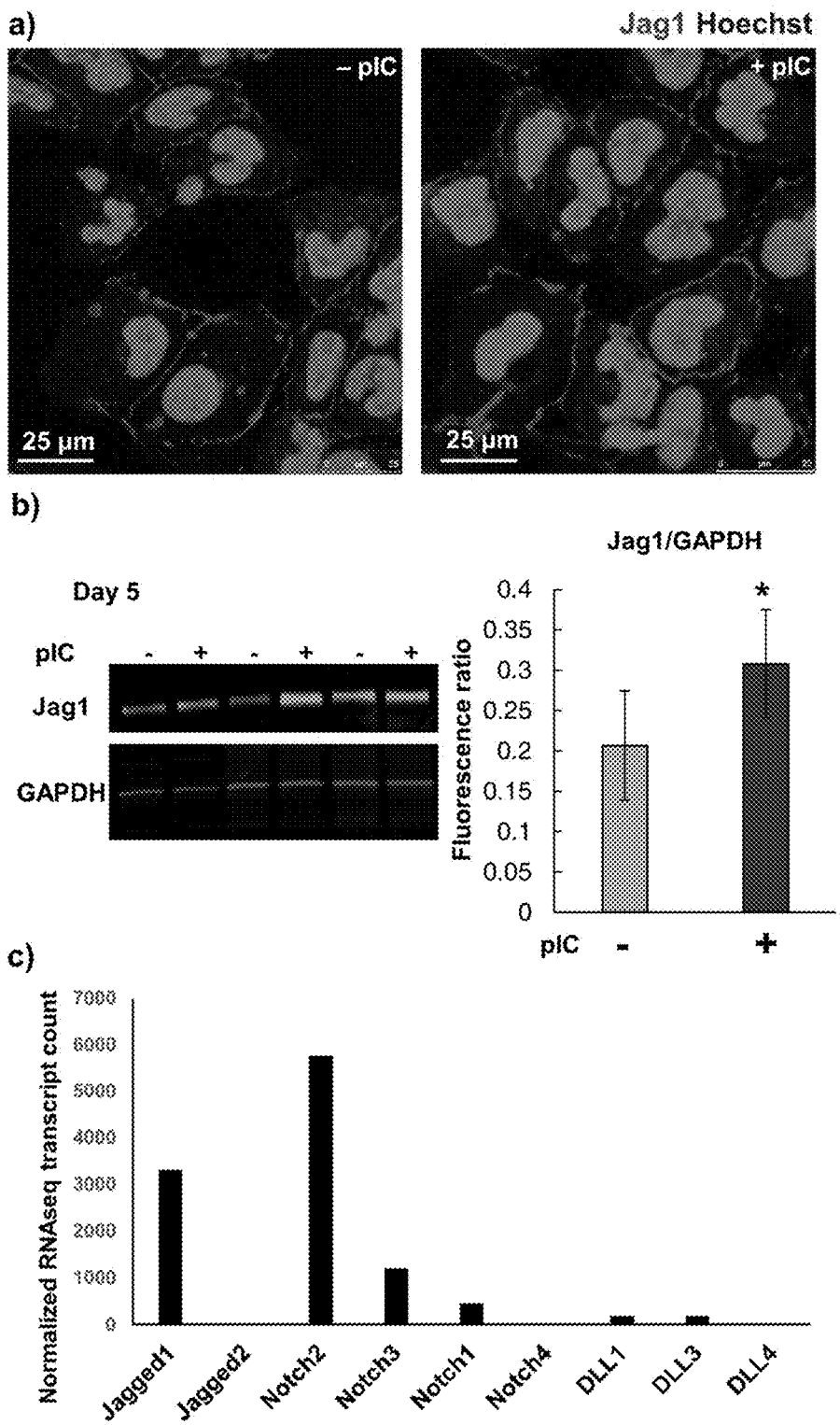
FIGS. 7A-7C—Cardiac progenitor cell Notch signaling

In cardiac development, Jag1 protein expression has not been previously described prior to expression in the early heart tube myocardium (Rutenberg et al., 2006). To determine if Jag1 is expressed in developing cardiac progenitors in vivo, we performed immunostaining for Jag1 in cardiac crescent-stage E8.25/4-somite mouse embryos (FIG. 5D). We found intense Jag1 expression in the cardiac progenitors of the cardiac crescent and the neighboring cells of the endoderm as well as in the yolk sac. We investigated Jag1 protein surface localization on the hPSC-derived cardiac progenitors by flow cytometry and immunostaining and found the majority of both primed and untreated progenitors expressed Jag1, but that both the percentage and median fluorescence of Jag1$^+$ cells in flow cytometry was increased in primed progenitors (FIG. 5E, 7A). This was also confirmed by quantitative, infrared western blotting (FIG. 7B). Jag1 and Notch2 were the most abundant notch ligand/receptor pair in the progenitors in RNAseq (FIG. 7C) and coexpressed on the same cells in flow cytometry, which suggests that primed progenitors with increased expression of Jag1 could mediate intralineage juxtacrine signaling.

We next examined the impact of pI:C on proliferation of day 5 cardiac progenitor cells and the role of Notch signaling. Cell cycle analysis using propidium iodide demonstrated that pI:C treatment of cardiac progenitors increased the fraction of day 5 cardiac progenitor cells in the G2/S phase of the cell cycle consistent with an increase in proliferation (FIG. 5G). Furthermore, the gamma secretase inhibitor of the Notch pathway DAPT blocked the increased cell cycle activity of primed progenitors. In contrast, day 30 hPSC-CMs showed a relatively small fraction of cells in G2/S and decreased Jag1 expression. To confirm that the increases in DNA synthesis in primed cardiac progenitor cells translated into increased proliferation, we dissociated the progenitors to single cells and performed a colony formation assay in 1% methylcellulose medium for four days. We observed abundant multi-cellular colonies from primed progenitors (size >35 μm), but mainly relatively rare, single cells from untreated progenitors (FIG. 5H).

Figures 8A, 8B, 8C, 8D, 8E:
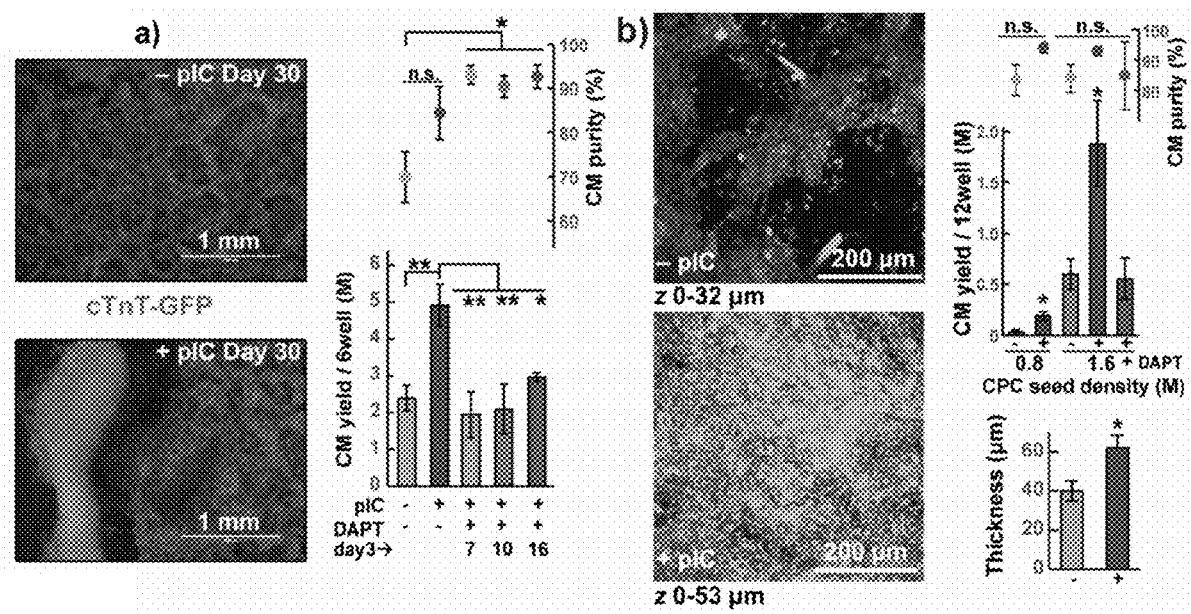
FIGS. 8A-8E—Notch inhibition blocks pI:C-stimulated proliferation and acceleration of hPSC-CM maturation FIG. 8A. Left: Live cell imaging of cTnT-GFP reporter hPSC-CMs showing formation of larger cardiomyocyte aggregations from primed progenitors. Right: Yield and purity by flow cytometry for day 30 hPSC-CMs from primed and untreated progenitors, or dual treated with Notch inhibitor DAPT, n=3-6.

The effect of pI:C treatment of cardiac progenitors on the resulting yield of cardiomyocytes and its regulation by Notch signaling was next assessed. The Notch inhibitor DAPT was administered either at an early time window when cardiac progenitors are present (day 3-5 or 3-7) or an extended window including progenitor and early cardiomyocyte stages (day 3-10 or 3-16). Congruent with pI:C's effect on cell cycle and growth of progenitors, progenitors given pI:C alone formed large aggregates of cardiomyocytes during differentiation and had more than double the yield of cardiomyocytes at day 30 despite statistically similar purities (FIG. 8A). Similar to the effect of Notch signaling on the cell cycle of progenitors at day 5, Notch inhibition via DAPT blocked pI:C's effect on hPSC-CM yield for both early and extended administration. Because the Notch pathway works by juxtacrine cell-cell contact signaling, we tested the effect of dissociation and replating of cardiac progenitors at different densities to determine whether the increased cardiomyocyte yield by pI:C treatment could be accentuated. We replated progenitors in basal medium and found that primed progenitors formed thicker sheets of densely packed cTnT-GFP$^+$ cardiomyocytes compared to untreated progenitors that formed porous sheets of patchy aggregations of cardiomyocytes. As in the GiWi protocol, primed progenitors generated cardiomyocytes with similar purity, but the yield of cardiomyocytes from primed progenitors increased 4-fold at high reseeding density and 6-fold at lower density (FIG. 8B). These experiments also showed that Notch inhibition with DAPT blocked this increased yield and that for both untreated and primed progenitors a 2-fold increase in seeding density produced a ~10-fold increase in cardiomyocyte yield, findings that provide more evidence to support a role for juxtacrine Notch signaling.

We next tested if the cardiomyocyte maturation effect of pI:C treatment of cardiac progenitors is dependent on Notch signaling. At the RNA level, DAPT reversed the increased expression of genes that are enriched as cardiomyocytes mature, such as αMHC, cardiac troponin I, cardiac actin, ATP synthase (ATP5a), ryanodine receptor (RYR2), and SERCA (FIG. 8C), whether it was applied acutely at day 3-5 or extended from day 3-16. In contrast, we noted that genes associated with cardiac fibroblasts—Thy1, Fibroblast Collagenase (MMP1), Collagen 1a, and WT1 were downregulated by pI:C treatment and this downregulation was accentuated by Notch inhibition (FIG. 8C).

Although Notch inhibition at the progenitor stage was sufficient to decrease the pI:C stimulation of genes associated with cardiac maturation, we found that post-transcriptional phenotypes were blocked only with extended Notch inhibition. The increase in optical upstroke velocity in cardiomyocytes from primed progenitors (decreased rise time) was blocked only with DAPT treatment from day 3-16 (FIG. 8D). And the protein isoform change toward adult cTnT 6 and 11 caused by pI:C was similarly abrogated only by Notch inhibition with DAPT extended to include early CM window (day 3-16, FIG. 8E). That Notch signaling has both progenitor and later phase effects in promoting cardiac maturation is consistent with previous reports in vivo in which Jag1 deletion driven by the cardiomyocyte-specific cTnT promoter decreases maturation (D'Amato et al., 2016). It is also possible that the changes in epigenetic modifiers with pI:C treatment (FIG. 6) lead to acute Notch-dependent effects on transcriptional phenotypes, but that post-transcriptional phenotypes of primed progenitors have temporally-extended Notch mechanistic requirements.

Primed Cardiac Progenitors Form Ventricular Conduction Microtissue

Figures 9A, 9B, 9C, 9D, 9E, 9F, 9G:
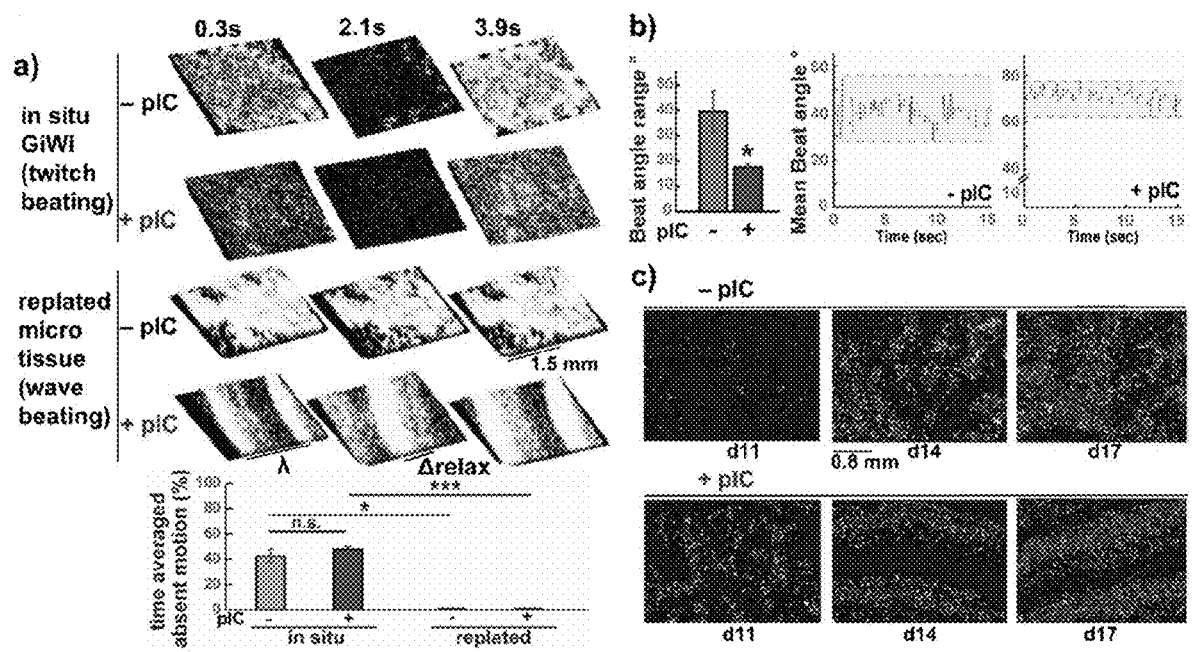
FIGS. 9A-9G—Formation of ventricular conduction microtissue from replated primed progenitors FIG. 9A. (Top) Video edge detection analysis of time-averaged motion velocity (z) over video image space (x and y). The replated primed progenitor sheets revealed waves of contraction compared to multifocal beating patterns of sheets from untreated progenitors. Sheets of cardiomyocytes from the in situ protocol exhibit "all or nothing" beating patterns with periods of complete absence of motion alternating with periods of uniform beating, quantified by (bottom) time averaged periods of absent motion, n=3.

During our cell dilution experiments (FIG. 8B), we visually observed that dissociated and replated cardiac progenitors generated cardiomyocyte sheets with a different pattern of contraction than the standard (non-replated) GiWi protocol with or without pI:C treatment. Video edge detection analysis showed that in situ hPSC-CMs beat in an "all-or-nothing" pattern, in which there are discrete periods of absent motion alternating with uniform contraction (FIG. 9A). In contrast, cell sheets generated from dissociated progenitors had motion evident throughout the video which in primed progenitors took the form of highly organized, propagating waves of contraction, whereas dissociated, untreated progenitors produced disorganized, multifocal patterns (FIG. 9A). We performed video motion analysis of contraction in the sheets from replated progenitors which confirmed more uniform motion in sheets from primed progenitors relative to untreated based on the lower range of the angle of the mean vector of contraction over time ("beat angle range," FIG. 9B).

The stark differences in contraction patterns of these cardiomyocyte sheets suggested fundamental differences in the organization of the cells. To evaluate these differences, we first characterized the development of the contraction of the cultures over earlier time points. We found the replated cultures of primed progenitors started to exhibit robust but disorganized multifocal contraction by day 11, whereas untreated progenitor cultures showed little contraction (FIG. 9C). By day 12-13, hPSC-CM sheets from untreated progenitors began to contract robustly but in similarly disorganized/multifocal areas of contraction that persisted throughout differentiation (as quantified in FIG. 9B). In contrast, the beating pattern of hPSC-CM sheets from primed progenitors transitioned to organized waves of contraction by day 13-14. Given that our prior results showed that Notch inhibition can block the increase in cardiomyocyte yield from pI:C treatment (FIG. 8B), we examined the effect of DAPT on the contraction pattern of hPSC-CM sheets from pI:C-primed progenitors and found that the contractions were multifocal and disorganized without forming waves of contraction if DAPT was present day3-day20. Thus, at least part of the impact of pI:C treatment on forming organized waves of contraction is due to increased cell proliferation and yield of cardiomyocytes that is dependent on continued Notch signaling through differentiation. Because Jag1 expression influenced proliferation at the progenitor stage, we characterized the expression of Jag1 in these differentiating cardiomyocytes. We surprisingly found that only after progenitor dissociation and replating do cardiomyocytes express Jag1 at day 30 in contrast to the in situ GiWi differentiation protocol (FIG. 9D). This striking difference in the expression of Jag1 is reminiscent of Jag1 expression being maintained and enhanced in the developing ventricular trabeculae during cardiac development (de la Pompa and Epstein, 2012). Another marker of the ventricular trabeculae, irx3 (Christoffels et al., 2000), was also predominantly expressed in cardiomyocytes from replated progenitors (FIG. 9D). Prior development studies have demonstrated that Jag1 and Notch signaling are required for ventricular trabeculation, compaction, and maturation in vivo (D'Amato et al., 2016; Han et al., 2016). Thus, we postulate that dissociation and replating of cardiac progenitors induces an in vitro process of trabeculation and generates Jag1$^+$ proliferative cardiomyocytes.

Conduction system cells develop from trabecular myocardium, and gain of function studies have shown that increased Notch signaling in adult or neonatal cardiomyocytes in vivo can reprogram cardiomyocytes toward a conduction system cell-like phenotype (Rentschler et al., 2012). To assess conduction system cell formation, we stained cardiomyocyte sheets for the conduction cell surface marker HCN4 (Später et al., 2013). HCN4 expression was completely absent in cardiomyocytes generated from nondissociated progenitors in the GiWi protocol, whereas HCN4 positive cells were clearly present in hPSC-CM sheets from both primed and untreated dissociated progenitors (FIG. 9E). Because HCN4 encodes a hyperpolarization activated channel responsible for $I_f$ and is integral in the automaticity of conduction system cardiomyocytes, we tested the effect of the $I_f$ blocker ivrabradine. Remarkably, ivrabradine blocked the spontaneous contractions of cardiomyocyte sheets from primed progenitors but had little effect on the rate of cardiomyocyte sheets from untreated progenitors (FIG. 9F). Because sinoatrial nodal cells can express HCN4 as well but do not express Nkx2.5 (Protze et al., 2017), we evaluated for the expression of Nkx2.5 in HCN4$^+$ cells and observed coexpression of Nkx2.5 consistent with a conduction system phenotype. HCN4$^+$ cardiomyocytes also expressed Cx40 which is a Cx isoform enriched in the conduction system (FIG. 9G).

Figures 10A, 10B:
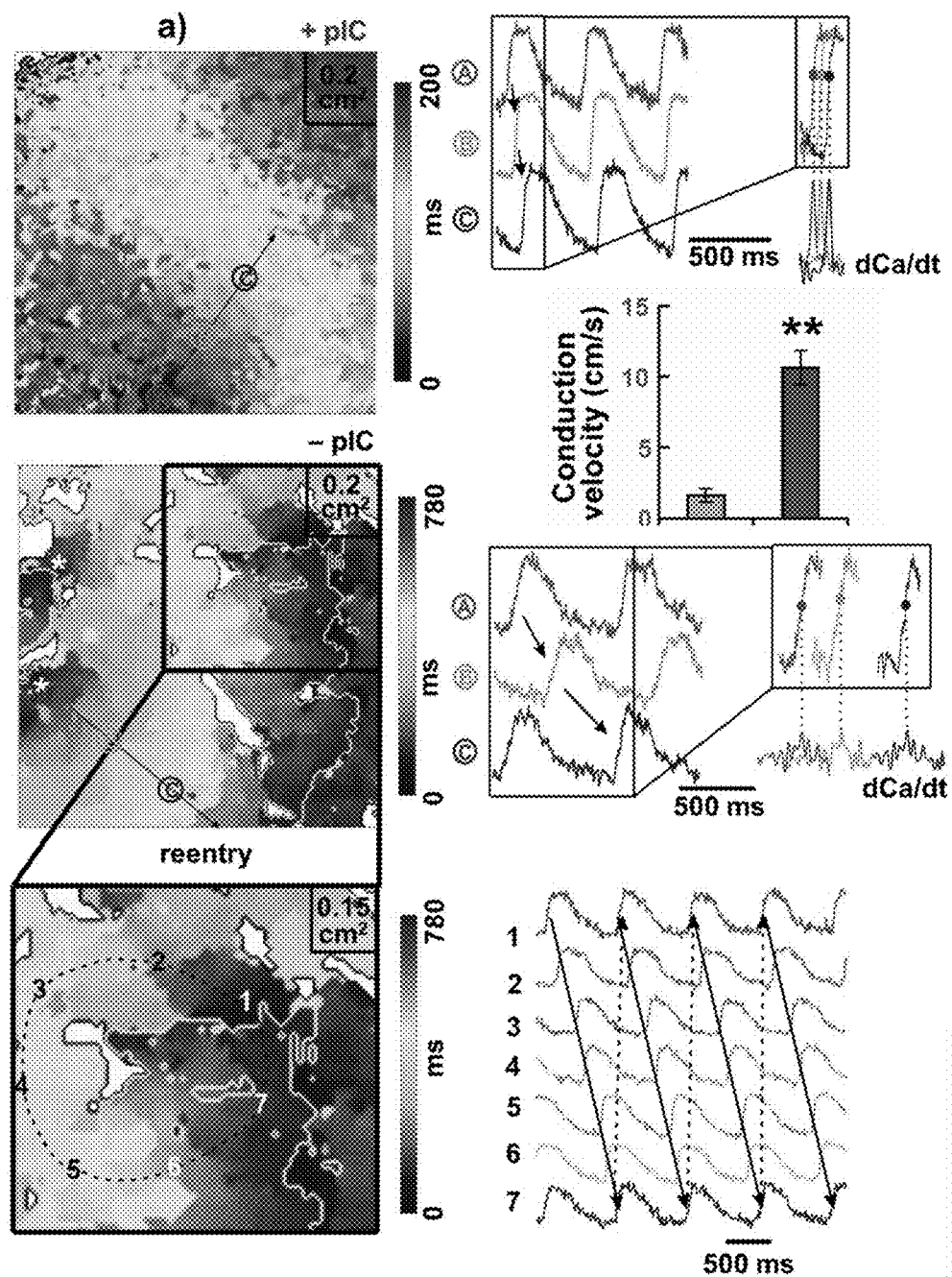
FIGS. 10A-10B—Ventricular conduction microtissue from pI:C primed dissociated progenitors exhibits organized conduction patterns associated with HCN4+ conduction system-like cells FIG. 10A demonstrates Rhod-2 Ca imaging of the wave-like motion of primed progenitor derived sheets vs untreated cells showing increased conduction velocity in microtissues from pI:C treated progenitors (n=3) and multifocal or reentrant circuits of conduction in microtissues from untreated progenitors.

Intracellular calcium optical mapping with Fluo4 was used to functionally characterize the pattern of conduction in the cardiac sheets generated from dissociated progenitors. As suggested from the characterization of contraction patterns, primed progenitor-derived sheets showed uniform waves of Ca transients in contrast to the multifocal patterns of excitation generated from cardiac sheets from untreated progenitors (FIG. 10A). Interestingly, the untreated progenitors often showed areas of continuous reentry which was not observed in sheets from primed progenitors. In addition, the average conduction velocity was 5-fold faster in sheets from primed progenitors. If the HCN4$^+$ cells are cells of the conduction system, then they are predicted to exhibit faster conduction relative to surrounding cardiomyocytes, so we performed live cell labeling for HCN4 together with intracellular calcium mapping. We found that areas of the sheets with high HCN4 immunolabeling did exhibit faster conduction velocities (FIG. 10B).

Thus, we conclude that dissociation and replating of cardiac progenitors initiates a process mimicking trabeculation and conduction system formation in embryonic development which in the setting of pI:C treatment produces networks of conduction system cells with more rapid conduction compared to the surrounding cardiomyocytes and thus enable organized wave propagation. We refer to these self-organizing cell sheets as ventricular conduction microtissue.

Primed Cardiac Progenitors Aid Infracted Mouse Hearts

Figures 11A, 11B, 11C, 11D:
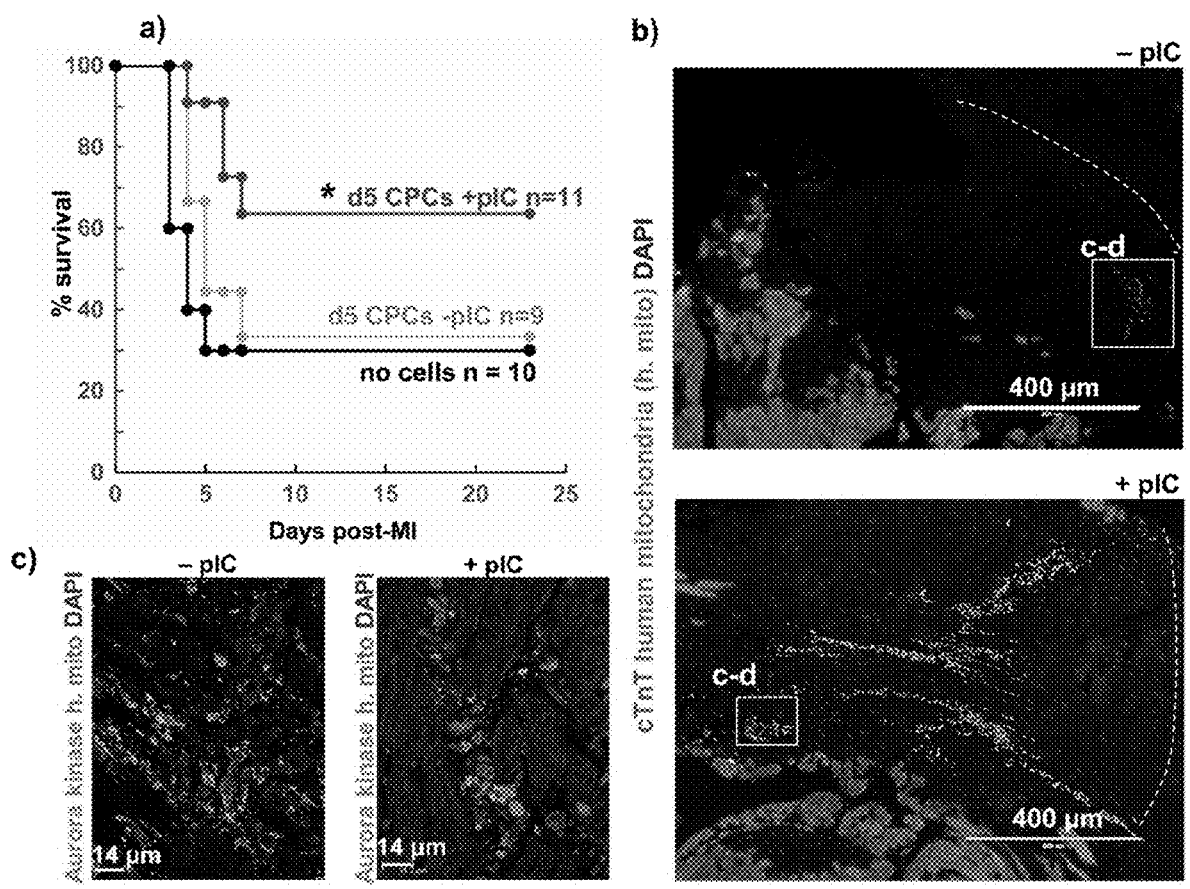
FIGS. 11A-11D—Improved survival in a mouse myocardial infarct model treated with primed progenitors FIG. 11A demonstrates that survival analysis showed a benefit in mortality to mice with infarcts that received primed progenitors compared to no cell treatment (p=0.04, log-rank survival analysis), but no benefit from untreated progenitors (p=0.42).

Given that primed progenitors have greater proliferation capacity and generate cardiomyocyte progeny with accelerated maturation, we hypothesized that primed cardiac progenitors could effectively promote repair of the adult heart following injury. Eight-week old C57BL/6J male mice were treated with cyclosporine for immunosuppression and then underwent surgical, permanent left coronary artery ligation. Primed day 5 cardiac progenitor cells, untreated day 5 cardiac progenitor cells, or saline placebo intramyocardial injections were delivered to the border zone of the infarct. We observed that primed progenitor delivery significantly improved survival of mice compared to PBS control over a three-week follow-up, but untreated progenitors did not have statistically significant impact on survival (FIG. 11A).

All mortality in the mouse groups occurred within the first week after infarction, consistent with peri-infarct complications such as ventricular rupture as the cause of death. Mice surviving at 3 weeks were sacrificed and evaluated with histology and immunofluorescence. To detect human cells we used an antibody to human mitochondria, but we did not observe human mitochondrial positive cells in the myocardium of animals at the 3 week time point. The loss of transplanted human cells at 3 weeks post-delivery is consistent with prior reports that the majority of human cells transplanted as xenografts in mice are lost after the first week of transplantation (Huber et al., 2013). However, we were able to detect human mitochondria positive cells in mice receiving progenitors that died during the first week of the study located in the infarct region (FIG. 11B). In co-labeling experiments primed and untreated progenitor human mitochondria$^+$ cells in the infarct had positive staining for Jag1, HCN4, and Mlc2v. Jag1$^+$ cells also expressed cardiac actin, which suggested that the cells differentiated to Jag1$^+$ cardiomyocytes as in the in vitro dissociated cell experiments above (FIG. 11D). In addition, we noticed that transplanted cells were often positive for the marker of cell division Aurora B kinase suggesting that the transplanted cells continue to proliferate at least initially (FIG. 11C).

pI:C Activates NFκB Signaling which Promotes hPSC-CM Maturation by Priming CPCs

Figures 12A, 12B, 12C:
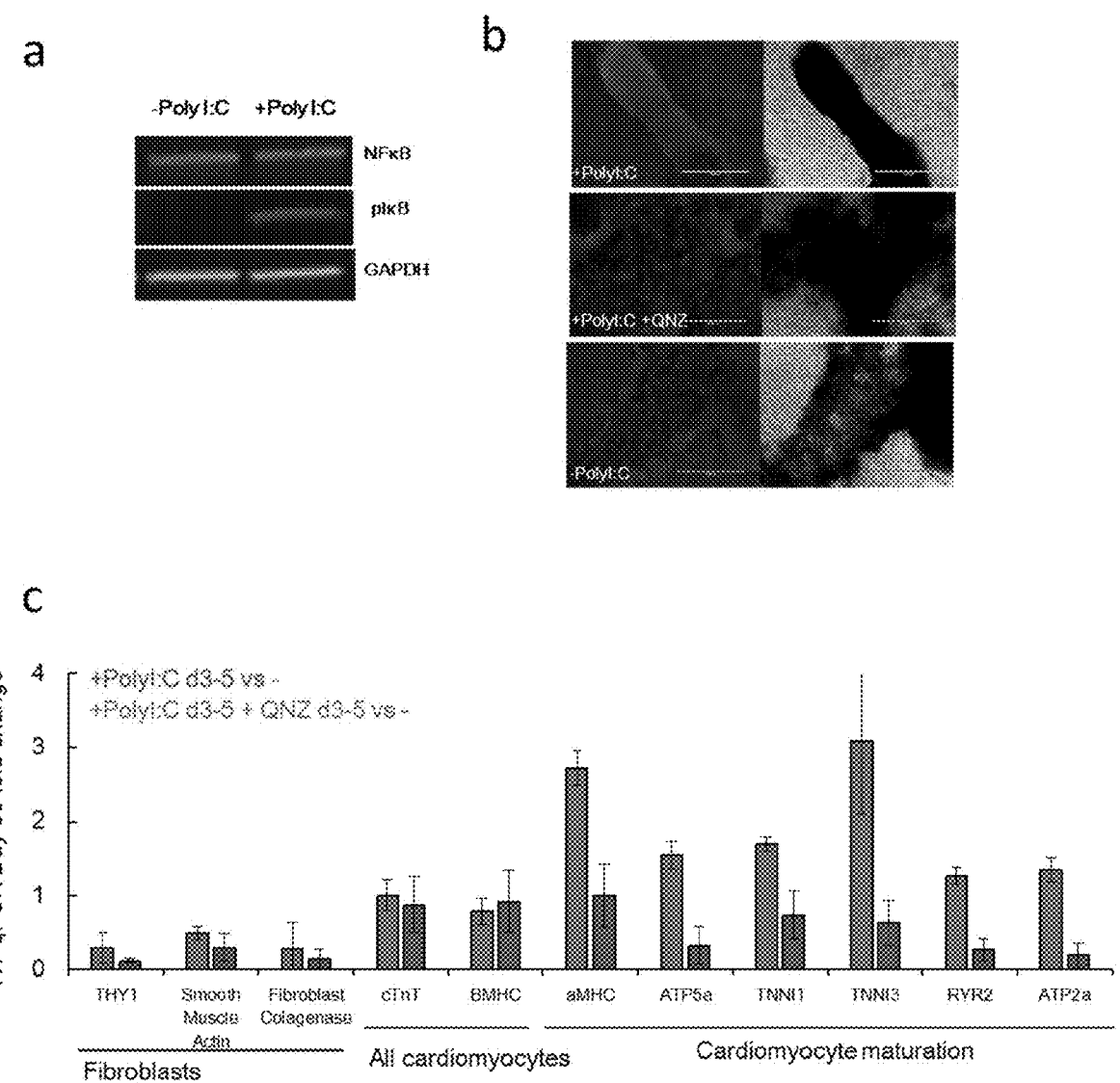
FIGS. 12A-12C—pI:C activates NFκB signaling which promotes hPSC-CM maturation

A previous study demonstrated that the enhanced reprogramming efficiency secondary to pI:C treatment of fibroblasts was secondary innate immune signaling through the NFκB pathway (Lee, J. et al. Activation of Innate Immunity is Required for Efficient Nuclear Reprogramming. Cell 151, 547-558 (2012)). To determine if pI:C treatment on days 3-5 of differentiation activated NFκB signaling, we performed a Western blot of day 5 cardiac progenitors using antibodies for NFκB (Abcam) and phosphorylated IKappaB (Abcam). Both pI:C treated and untreated cardiac progenitors expressed NFκB but only pI:C treated progenitors showed expression of phosphorylated (inactivated) inhibitor IκB, an indicator of activation of the NFκB signaling pathway (FIG. 12A). Next we tested the effect of the NFκB inhibitor, QNZ (Selleckchem), applied day 3-5 concurrent with p I:C treatment, and found that QNZ blocked the generation of large collections of TnT-GFP positive cardiomyocytes typically found after pIC treatment (FIG. 12B). We examined changes in day 20 pPSC-CM gene expression as a result of pI:C treatment and tested the sensitivity to the NFκB inhibitor, QNZ. In general, pI:C treatment increased the expression levels for genes associated with cardiomyocyte maturation such as cTnI and αMHC, and this increase was reversed by QNZ treatment (FIG. 12C). These results suggest that pI:C treatment of day 3-5 differentiating cells activates NFκB signaling to promote enhanced hPSC-CM maturation. These data further suggest that primed cardiac progenitors can be obtained using activators of NFκB signaling as well as TLR3 ligands.

Discussion

Here we describe the striking effects of pI:C in priming hPSC-derived cardiac progenitor cells for increased cellular proliferation and accelerated maturation of cardiomyocytes. Gene expression analysis and inhibitor studies demonstrated an essential role for Notch signaling in progenitor priming. We further discovered that dissociation and replating of cardiac progenitor cells lead to a new pattern of self-organization mimicking trabeculation of cardiac tissue with the formation of cardiac conduction system-like cells. In this process primed cardiac progenitors generated ventricular conduction microtissue with highly organized waves of contraction. Finally, we show that primed cardiac progenitor cells can improve survival after myocardial infarction in a mouse model.

Previous studies aiming to advance the maturation of hPSC-CMs have focused interventions on differentiated cardiomyocytes (Yang et al., 2014), but in this study we demonstrate that intervention at the cardiac progenitor stage can promote the maturation of hPSC-CMs. These results suggest that the pI:C treatment impacts a developmental clock regulating the kinetics of maturation. Developmental clocks have been described in other mesodermal-derived progenitors to regulate the precisely timed formation of somites and segmentation of the vertebrate body. This segmentation clock results from cell autonomous cyclic activation of Notch, Wnt/β-catenin and FGF signaling leading to phasic expression of downstream genes (Oates et al., 2012). Species-specific differences in developmental kinetics also suggest intrinsic clock function in various progenitor populations (Barry et al., 2017). In cardiac development, an intrinsic clock regulating differentiation and maturation of cardiomyocytes has not been well defined, but our results suggest that Notch signaling is involved in this function. This is consistent with a recent study demonstrating that loss of Jag1 disrupts the proliferation of ventricular cardiomyocytes in the early heart leading to a thin and immature ventricular myocardium (D'Amato et al., 2016). Further studies will be needed to define clock mechanisms in cardiac development and how pI:C treatment impacts clock function. Whether pI:C has similar effects on other tissue-specific progenitors is also an intriguing question for future studies. Finally, future studies combining pI:C treatment of progenitors with interventions on differentiated hPSC-CMs may yield synergistic effects on maturation.

The surprising finding that dissociation and replating of cardiac progenitors under defined conditions promotes a trabeculation-like process with proliferative Jag1$^+$ cardiomyocytes and formation of ventricular conduction system-like cells provides a new in vitro model system to study these critical events in human cardiac development and investigate forms of congenital heart disease. These methods provide the first access to hPSC-CMs that display the properties of ventricular conduction system-like cells, which are a critical cell type in enabling rapid conduction throughout the ventricular myocardium and also an important cell population in disease serving as a trigger for various arrhythmias. Previous studies have isolated conduction system cells from differentiating mouse PSCs using genetic reporters (Maass et al., 2015), but these results provide the first description of this cell type from human PSCs. Furthermore, primed progenitors in this system self-organize to form ventricular conduction microtissue with areas of HCN4$^+$ cells generating rapid conduction relative to the surrounding hPCS-CMs mimicking organized patterns of conduction in the native heart. This ventricular conduction microtissue provides a new testbed for screening small molecules for impact on ventricular conduction tissue which is a vulnerable area for the genesis of arrhythmias and an excellent target for antiarrhythmic drugs.

Our initial studies show primed progenitors exert a positive benefit post-MI improving survival in a mouse model relative to placebo and unprimed progenitors. pI:C has undergone safety evaluation as an FDA-approved agent for use as an adjuvant in chemotherapy or certain vaccines. Therefore, treating cardiac progenitors with pI:C is also practical to implement for clinical applications, especially relative to other approaches to engineer cells such as genetic modification. Future studies in larger animal models with longer follow-up are needed to fully optimize this cellular product and define its mechanisms of benefit.

TABLE 3 pI:C top 100 upregulated genes

|  | baseMean | log2FoldChange | lfcSE | stat | pvalue | padj |
|---|---|---|---|---|---|---|
| JAG1 | 3321.811503 | 1.452893612 | 0.087343 | 16.63425 | 3.94E−62 | 1.92E−58 |
| SIX1 | 134.1773882 | 1.396620182 | 0.160299 | 8.712572 | 2.97E−18 | 8.78E−16 |
| CD82 | 164.8646356 | 1.288329056 | 0.155151 | 8.303716 | 1.01E−16 | 2.39E−14 |
| NPY | 96.89515991 | 1.254024293 | 0.164911 | 7.60427 | 2.87E−14 | 5.06E−12 |
| FOXL1 | 65.3100214 | 1.222958285 | 0.17288 | 7.074029 | 1.50E−12 | 1.93E−10 |
| PPP1R1A | 415.1064733 | 1.171301333 | 0.128563 | 9.110686 | 8.19E−20 | 2.93E−17 |
| ANKRD18A | 96.49802936 | 1.148287416 | 0.159851 | 7.183482 | 6.80E−13 | 9.49E−11 |
| PANX2 | 68.80814056 | 1.106667008 | 0.173713 | 6.370665 | 1.88E−10 | 1.90E−08 |
| ALDH1A2 | 121.7555741 | 1.066606795 | 0.159271 | 6.696824 | 2.13E−11 | 2.42E−09 |
| IFI16 | 669.2681992 | 1.021049625 | 0.107104 | 9.53327 | 1.52E−21 | 6.38E−19 |
| FAM98B | 434.0297862 | 1.007657946 | 0.110915 | 9.08494 | 1.04E−19 | 3.62E−17 |
| PDE1B | 246.8061052 | 0.999516602 | 0.132362 | 7.551413 | 4.31E−14 | 7.51E−12 |
| PAPPA | 787.7231589 | 0.980829454 | 0.115923 | 8.461035 | 2.65E−17 | 6.70E−15 |
| MMP16 | 1317.064133 | 0.977236517 | 0.10201 | 9.579816 | 9.72E−22 | 4.19E−19 |
| PRSS23 | 248.5086496 | 0.976532847 | 0.13709 | 7.123272 | 1.05E−12 | 1.42E−10 |
| NKX3-1 | 321.5572484 | 0.97349361 | 0.12487 | 7.796028 | 6.39E−15 | 1.22E−12 |
| C20orf103 | 89.62794964 | 0.967432705 | 0.172781 | 5.599176 | 2.15E−08 | 1.46E−06 |
| COL2A1 | 2595.640538 | 0.966558187 | 0.111631 | 8.658541 | 4.78E−18 | 1.37E−15 |
| ADCY5 | 244.9197204 | 0.9552148 | 0.142843 | 6.687154 | 2.28E−11 | 2.55E−09 |
| SYT4 | 105.0341306 | 0.936342468 | 0.156847 | 5.969789 | 2.38E−09 | 2.01E−07 |
| RARB | 802.3120204 | 0.92906639 | 0.096097 | 9.668007 | 4.12E−22 | 2.01E−19 |
| EYA1 | 86.5442159 | 0.92695465 | 0.164654 | 5.629716 | 1.81E−08 | 1.26E−06 |
| NETO1 | 612.8444943 | 0.917959552 | 0.108383 | 8.469607 | 2.46E−17 | 6.45E−15 |
| IRX5 | 216.3437495 | 0.917427215 | 0.13804 | 6.646086 | 3.01E−11 | 3.30E−09 |
| KIAA1324 | 78.99130077 | 0.914047646 | 0.161932 | 5.644655 | 1.66E−08 | 1.16E−06 |
| FOXC1 | 804.2958498 | 0.907721535 | 0.111092 | 8.170922 | 3.06E−16 | 6.50E−14 |
| MN1 | 343.9045695 | 0.893852737 | 0.126312 | 7.076553 | 1.48E−12 | 1.92E−10 |
| HLA-DQA2 | 58.07523529 | 0.880982611 | 0.174219 | 5.056758 | 4.26E−07 | 2.25E−05 |
| AQP3 | 73.25098249 | 0.87780228 | 0.166202 | 5.281528 | 1.28E−07 | 7.45E−06 |
| KCNH7 | 33.88192226 | 0.86267205 | 0.171309 | 5.035764 | 4.76E−07 | 2.47E−05 |
| HAPLN3 | 113.5729944 | 0.846784014 | 0.154719 | 5.473036 | 4.42E−08 | 2.81E−06 |
| FOXC2 | 26.67087006 | 0.820348439 | 0.171914 | 4.771848 | 1.83E−06 | 8.01E−05 |
| CTNNA2 | 363.381045 | 0.819886731 | 0.114088 | 7.186464 | 6.65E−13 | 9.37E−11 |
| PPFIA2 | 95.62986777 | 0.818866154 | 0.166257 | 4.925308 | 8.42E−07 | 4.12E−05 |
| PRSS12 | 403.5301344 | 0.817009769 | 0.121435 | 6.727955 | 1.72E−11 | 2.00E−09 |

TABLE 3-continued pI:C top 100 upregulated genes

|  | baseMean | log2FoldChange | lfcSE | stat | pvalue | padj |
|---|---|---|---|---|---|---|
| MYO7A | 144.502176 | 0.815042628 | 0.143603 | 5.675672 | 1.38E−08 | 9.83E−07 |
| DKK1 | 338.0815438 | 0.808404688 | 0.137611 | 5.874572 | 4.24E−09 | 3.49E−07 |
| TXNIP | 292.3676924 | 0.805015957 | 0.151324 | 5.319827 | 1.04E−07 | 6.16E−06 |
| CNTFR | 165.2980976 | 0.803761536 | 0.139672 | 5.754645 | 8.68E−09 | 6.39E−07 |
| MT1X | 57.07715879 | 0.786676309 | 0.171017 | 4.599981 | 4.23E−06 | 0.000168 |
| RHBDL3 | 122.8603488 | 0.786127241 | 0.155633 | 5.051149 | 4.39E−07 | 2.31E−05 |
| DKFZp686D0853 | 163.834116 | 0.781999597 | 0.140704 | 5.557763 | 2.73E−08 | 1.80E−06 |
| STAR | 165.0774349 | 0.780631963 | 0.160517 | 4.863242 | 1.15E−06 | 5.42E−05 |
| PTPN12 | 1384.625703 | 0.763096824 | 0.085358 | 8.939916 | 3.89E−19 | 1.30E−16 |
| PTN | 597.2226023 | 0.753642954 | 0.096304 | 7.82563 | 5.05E−15 | 9.74E−13 |
| IRX3 | 749.7322637 | 0.745176119 | 0.106669 | 6.985873 | 2.83E−12 | 3.58E−10 |
| SLC24A3 | 36.42124455 | 0.739695623 | 0.173533 | 4.262558 | 2.02E−05 | 0.00067 |
| NR2F1 | 46.30974963 | 0.735577788 | 0.172198 | 4.271706 | 1.94E−05 | 0.000646 |
| CRNDE | 404.7473032 | 0.734655122 | 0.111121 | 6.611327 | 3.81E−11 | 4.10E−09 |
| DLL3 | 177.4689061 | 0.728492051 | 0.140103 | 5.199679 | 2.00E−07 | 1.13E−05 |
| NFKBIZ | 302.4967472 | 0.724647968 | 0.129665 | 5.588599 | 2.29E−08 | 1.54E−06 |
| NRXN1 | 385.5750331 | 0.72401607 | 0.119937 | 6.036651 | 1.57E−09 | 1.36E−07 |
| SCGB1A1 | 20.88971004 | 0.702836048 | 0.165002 | 4.259555 | 2.05E−05 | 0.000678 |
| SPOCK3 | 327.5652396 | 0.696081039 | 0.17445 | 3.990154 | 6.60E−05 | 0.00184 |
| IP6K3 | 31.95574192 | 0.695334527 | 0.17439 | 3.987235 | 6.68E−05 | 0.001856 |
| USP27X | 347.0778262 | 0.694600536 | 0.115859 | 5.994205 | 2.04E−09 | 1.76E−07 |
| RERG | 44.29888323 | 0.691325037 | 0.172847 | 3.999633 | 6.34E−05 | 0.001778 |
| CHRNA3 | 112.4155321 | 0.686453111 | 0.15318 | 4.481363 | 7.42E−06 | 0.000276 |
| FHDC1 | 82.06509842 | 0.683120193 | 0.161394 | 4.232617 | 2.31E−05 | 0.000749 |
| SYT6 | 177.5317719 | 0.675156829 | 0.154195 | 4.378589 | 1.19E−05 | 0.00042 |
| HEY1 | 852.6717775 | 0.670566009 | 0.119691 | 5.602494 | 2.11E−08 | 1.44E−06 |
| NELL2 | 733.283829 | 0.669633915 | 0.116261 | 5.759725 | 8.43E−09 | 6.24E−07 |
| NEFL | 36.86364821 | 0.664676251 | 0.173814 | 3.824063 | 0.000131 | 0.003294 |
| GPC3 | 1532.487458 | 0.664660801 | 0.100065 | 6.645594 | 3.02E−11 | 3.30E−09 |
| PDGFD | 107.1246217 | 0.661897682 | 0.154426 | 4.286191 | 1.82E−05 | 0.00061 |
| ARL15 | 158.9573892 | 0.645903657 | 0.141107 | 4.57741 | 4.71E−06 | 0.000185 |
| TOX | 138.7924574 | 0.643730758 | 0.151593 | 4.246451 | 2.17E−05 | 0.000715 |
| PPM1J | 87.32748951 | 0.636404889 | 0.159663 | 3.985938 | 6.72E−05 | 0.001862 |
| TMEM132E | 56.85471797 | 0.636149651 | 0.174132 | 3.653256 | 0.000259 | 0.005893 |
| LIX1 | 5757.272989 | 0.636060492 | 0.094881 | 6.70378 | 2.03E−11 | 2.33E−09 |
| ADCY8 | 103.7068866 | 0.634230081 | 0.167525 | 3.78589 | 0.000153 | 0.00376 |
| DPYSL5 | 175.710085 | 0.625376163 | 0.138243 | 4.523762 | 6.08E−06 | 0.000231 |
| ACTN3 | 279.2094968 | 0.619347188 | 0.140447 | 4.409824 | 1.03E−05 | 0.00037 |
| ROBO3 | 170.389872 | 0.617432007 | 0.16065 | 3.843344 | 0.000121 | 0.003083 |
| CDC25B | 325.8802665 | 0.617328028 | 0.13993 | 4.411695 | 1.03E−05 | 0.000368 |
| KIAA0319 | 45.27042225 | 0.61417588 | 0.172971 | 3.550736 | 0.000384 | 0.008113 |
| EPHB3 | 1588.209395 | 0.612231247 | 0.089803 | 6.817507 | 9.26E−12 | 1.10E−09 |
| TMPRSS13 | 53.7421452 | 0.608592875 | 0.171433 | 3.550027 | 0.000385 | 0.008123 |
| CHRNB4 | 52.68798934 | 0.608540102 | 0.173506 | 3.507321 | 0.000453 | 0.009266 |
| RND3 | 799.4647455 | 0.605313752 | 0.101551 | 5.960667 | 2.51E−09 | 2.12E−07 |
| BAI2 | 196.7476937 | 0.604603871 | 0.142278 | 4.249448 | 2.14E−05 | 0.000707 |
| ARSI | 38.0913847 | 0.60430438 | 0.174427 | 3.464518 | 0.000531 | 0.010507 |

TABLE 4 pI:C top 100 downregulated genes

|  | baseMean | log2FoldChange | lfcSE | stat | pvalue | padj |
|---|---|---|---|---|---|---|
| NODAL | 228.16 | −2.608 | 0.138756 | −18.7931 | 8.59E−79 | 6.30E−75 |
| PITX2 | 264.03 | −2.05 | 0.139175 | −14.7282 | 4.25E−49 | 1.04E−45 |
| SERPINE2 | 5707.4 | −1.834 | 0.071821 | −25.5293 | 9.33E−144 | 1.37E−139 |
| RYR3 | 202.09 | −1.699 | 0.138545 | −12.2647 | 1.40E−34 | 1.87E−31 |
| SLC5A9 | 182.06 | −1.697 | 0.151994 | −11.1626 | 6.22E−29 | 6.07E−26 |
| GPR55 | 55.471 | −1.691 | 0.17279 | −9.78688 | 1.28E−22 | 6.48E−20 |
| TRPA1 | 75.849 | −1.599 | 0.169629 | −9.42733 | 4.21E−21 | 1.67E−18 |
| ATP8B4 | 197.73 | −1.545 | 0.142876 | −10.8138 | 2.96E−27 | 2.55E−24 |
| NRCAM | 883.24 | −1.533 | 0.096046 | −15.9615 | 2.37E−57 | 8.69E−54 |
| SLC28A2 | 279.84 | −1.472 | 0.138513 | −10.6244 | 2.29E−26 | 1.68E−23 |
| TMOD1 | 130.47 | −1.407 | 0.151932 | −9.26116 | 2.02E−20 | 7.60E−18 |
| ADAMTS18 | 281.68 | −1.365 | 0.1331 | −10.2552 | 1.12E−24 | 6.85E−22 |
| HAND1 | 975.5 | −1.326 | 0.102772 | −12.9071 | 4.10E−38 | 7.52E−35 |
| RASSF10 | 196.13 | −1.321 | 0.132004 | −10.0066 | 1.43E−23 | 7.74E−21 |
| MXRA5 | 174.59 | −1.313 | 0.138077 | −9.51186 | 1.87E−21 | 7.63E−19 |
| DUSP4 | 848.48 | −1.302 | 0.087144 | −14.9413 | 1.78E−50 | 5.20E−47 |
| TBX3 | 1312.9 | −1.289 | 0.090278 | −14.2764 | 3.07E−46 | 6.43E−43 |
| VEPH1 | 78.915 | −1.26 | 0.167376 | −7.5282 | 5.14E−14 | 8.67E−12 |
| KCNJ16 | 50.064 | −1.26 | 0.174284 | −7.22683 | 4.94E−13 | 7.17E−11 |

TABLE 4-continued pI:C top 100 downregulated genes

| | baseMean | log2FoldChange | lfcSE | stat | pvalue | padj |
|---|---|---|---|---|---|---|
| CD300E | 46.209 | −1.257 | 0.173349 | −7.25235 | 4.10E−13 | 6.13E−11 |
| HNF4A | 291.73 | −1.257 | 0.124132 | −10.1274 | 4.18E−24 | 2.35E−21 |
| SLCO2A1 | 70.194 | −1.248 | 0.165509 | −7.5398 | 4.71E−14 | 8.02E−12 |
| ACTC1 | 1365.1 | −1.232 | 0.166334 | −7.40945 | 1.27E−13 | 2.02E−11 |
| CYP4X1 | 236.63 | −1.23 | 0.150149 | −8.19076 | 2.60E−16 | 5.76E−14 |
| KIAA1024 | 393.24 | −1.206 | 0.125143 | −9.63518 | 5.68E−22 | 2.60E−19 |
| DENND2C | 655.8 | −1.203 | 0.113095 | −10.634 | 2.07E−26 | 1.60E−23 |
| ITIH5 | 196.15 | −1.197 | 0.148761 | −8.04945 | 8.32E−16 | 1.67E−13 |
| DOK4 | 3183.8 | −1.188 | 0.096264 | −12.3362 | 5.78E−35 | 8.48E−32 |
| NPNT | 261.02 | −1.156 | 0.13422 | −8.61393 | 7.06E−18 | 1.95E−15 |
| CRLF1 | 82.889 | −1.153 | 0.16787 | −6.86574 | 6.61E−12 | 8.01E−10 |
| S100A14 | 263.31 | −1.152 | 0.12356 | −9.32059 | 1.16E−20 | 4.46E−18 |
| RIMBP2 | 23.791 | −1.14 | 0.170312 | −6.69238 | 2.20E−11 | 2.48E−09 |
| BMP6 | 100.79 | −1.131 | 0.156799 | −7.21037 | 5.58E−13 | 7.94E−11 |
| MSX2 | 603.67 | −1.13 | 0.098205 | −11.5114 | 1.16E−30 | 1.41E−27 |
| HS3ST1 | 85.497 | −1.124 | 0.160126 | −7.01912 | 2.23E−12 | 2.85E−10 |
| ESRRG | 282.91 | −1.104 | 0.131747 | −8.37875 | 5.35E−17 | 1.31E−14 |
| SMAD6 | 999.49 | −1.083 | 0.10646 | −10.1745 | 2.58E−24 | 1.51E−21 |
| FMOD | 263.94 | −1.082 | 0.137313 | −7.88094 | 3.25E−15 | 6.35E−13 |
| LRRK2 | 38.358 | −1.07 | 0.174497 | −6.13257 | 8.65E−10 | 7.73E−08 |
| F2RL2 | 188.66 | −1.068 | 0.14332 | −7.45135 | 9.24E−14 | 1.50E−11 |
| SLC24A2 | 51.052 | −1.063 | 0.171893 | −6.18176 | 6.34E−10 | 5.81E−08 |
| ADAM19 | 2143.7 | −1.052 | 0.081807 | −12.8568 | 7.88E−38 | 1.28E−34 |
| ST3GAL1 | 1629.9 | −1.042 | 0.100621 | −10.3584 | 3.83E−25 | 2.55E−22 |
| SHROOM4 | 303.05 | −1.04 | 0.11918 | −8.72991 | 2.55E−18 | 7.78E−16 |
| HNF1B | 165.11 | −1.032 | 0.144919 | −7.1204 | 1.08E−12 | 1.42E−10 |
| CNR1 | 95.636 | −1.019 | 0.158178 | −6.43949 | 1.20E−10 | 1.24E−08 |
| SPTLC3 | 73.492 | −1.015 | 0.173285 | −5.85496 | 4.77E−09 | 3.89E−07 |
| DIO2 | 85.523 | −1.012 | 0.169439 | −5.97115 | 2.36E−09 | 2.01E−07 |
| PMEPA1 | 47.806 | −1.009 | 0.173104 | −5.83066 | 5.52E−09 | 4.40E−07 |
| SYTL5 | 1414.9 | −1.009 | 0.173318 | −5.81938 | 5.91E−09 | 4.63E−07 |
| GADL1 | 70.783 | −1.006 | 0.164986 | −6.0969 | 1.08E−09 | 9.55E−08 |
| SLC7A7 | 292.23 | −1.001 | 0.121904 | −8.20857 | 2.24E−16 | 5.13E−14 |
| S100A10 | 1233.1 | −0.988 | 0.110763 | −8.92022 | 4.65E−19 | 1.52E−16 |
| TFCP2L1 | 70.204 | −0.979 | 0.168674 | −5.80594 | 6.40E−09 | 4.94E−07 |
| SOX 17 | 483.47 | −0.973 | 0.134217 | −7.24675 | 4.27E−13 | 6.32E−11 |
| CRHBP | 64.998 | −0.963 | 0.173344 | −5.55803 | 2.73E−08 | 1.80E−06 |
| DPP4 | 32.607 | −0.96 | 0.165201 | −5.81306 | 6.13E−09 | 4.78E−07 |
| FZD8 | 293.46 | −0.96 | 0.117414 | −8.17726 | 2.90E−16 | 6.35E−14 |
| SOST | 154.47 | −0.955 | 0.150768 | −6.33367 | 2.39E−10 | 2.40E−08 |
| SRC | 1058.4 | −0.952 | 0.084446 | −11.2748 | 1.75E−29 | 1.83E−26 |
| PPARGC1A | 41.564 | −0.948 | 0.1744 | −5.43637 | 5.44E−08 | 3.38E−06 |
| MSX1 | 318.72 | −0.94 | 0.116201 | −8.09057 | 5.94E−16 | 1.23E−13 |
| HHEX | 444.47 | −0.938 | 0.106936 | −8.76744 | 1.83E−18 | 5.70E−16 |
| APOA1 | 376.09 | −0.934 | 0.172495 | −5.41407 | 6.16E−08 | 3.78E−06 |
| PTK2B | 142.74 | −0.933 | 0.154256 | −6.04753 | 1.47E−09 | 1.28E−07 |
| DTNA | 127.89 | −0.932 | 0.145928 | −6.38393 | 1.73E−10 | 1.76E−08 |
| FRY | 491.5 | −0.911 | 0.115527 | −7.88622 | 3.11E−15 | 6.17E−13 |
| GYPB | 68.958 | −0.909 | 0.1743 | −5.21738 | 1.81E−07 | 1.03E−05 |
| APOBEC3G | 111.94 | −0.909 | 0.159476 | −5.70223 | 1.18E−08 | 8.54E−07 |
| FADS6 | 34.203 | −0.909 | 0.173685 | −5.2356 | 1.64E−07 | 9.45E−06 |
| EXPH5 | 731.56 | −0.906 | 0.120052 | −7.54355 | 4.57E−14 | 7.89E−12 |
| DIO3 | 74.483 | −0.899 | 0.16864 | −5.32841 | 9.91E−08 | 5.95E−06 |
| ATP8A1 | 374.89 | −0.897 | 0.121108 | −7.40256 | 1.34E−13 | 2.11E−11 |
| BMPR2 | 1411.3 | −0.888 | 0.086082 | −10.3115 | 6.25E−25 | 3.99E−22 |
| EEF1A2 | 84.891 | −0.887 | 0.161825 | −5.48396 | 4.16E−08 | 2.65E−06 |
| FLI1 | 101.62 | −0.884 | 0.163916 | −5.39171 | 6.98E−08 | 4.24E−06 |
| ARHGAP24 | 324.12 | −0.882 | 0.126939 | −6.9486 | 3.69E−12 | 4.58E−10 |
| GPR133 | 135.01 | −0.882 | 0.158553 | −5.56024 | 2.69E−08 | 1.79E−06 |
| DGKB | 50.634 | −0.881 | 0.171455 | −5.13816 | 2.77E−07 | 1.52E−05 |
| MAL2 | 585 | −0.879 | 0.108192 | −8.12102 | 4.62E−16 | 9.68E−14 |
| PCSK2 | 34.119 | −0.868 | 0.174483 | −4.97453 | 6.54E−07 | 3.29E−05 |
| PRKCE | 127.57 | −0.868 | 0.155474 | −5.58234 | 2.37E−08 | 1.59E−06 |
| C21orf129 | 95.26 | −0.859 | 0.157543 | −5.45243 | 4.97E−08 | 3.11E−06 |
| SLC39A8 | 988.44 | −0.858 | 0.098531 | −8.7117 | 2.99E−18 | 8.78E−16 |
| CNTN3 | 23.424 | −0.857 | 0.169057 | −5.0722 | 3.93E−07 | 2.09E−05 |
| EPAS1 | 156.05 | −0.855 | 0.148277 | −5.76366 | 8.23E−09 | 6.12E−07 |
| OXTR | 39.937 | −0.854 | 0.174185 | −4.90148 | 9.51E−07 | 4.57E−05 |
| PEG10 | 7088.1 | −0.854 | 0.086544 | −9.86224 | 6.07E−23 | 3.18E−20 |
| SMAD7 | 1140.7 | −0.852 | 0.088551 | −9.62112 | 6.51E−22 | 2.89E−19 |
| SAMSN1 | 43.775 | −0.851 | 0.174241 | −4.88296 | 1.05E−06 | 4.99E−05 |
| GLIPR2 | 1547.8 | −0.848 | 0.087907 | −9.65153 | 4.84E−22 | 2.29E−19 |
| SLC22A3 | 139.93 | −0.845 | 0.153219 | −5.51725 | 3.44E−08 | 2.23E−06 |
| FGFR4 | 796.95 | −0.843 | 0.097653 | −8.62996 | 6.14E−18 | 1.73E−15 |
| NDRG2 | 368.91 | −0.838 | 0.118276 | −7.08442 | 1.40E−12 | 1.83E−10 |
| GREM2 | 34.66 | −0.837 | 0.170558 | −4.90516 | 9.34E−07 | 4.50E−05 |

TABLE 4-continued

| | pI:C top 100 downregulated genes | | | | | |
|---|---|---|---|---|---|---|
| | baseMean | log2FoldChange | lfcSE | stat | pvalue | padj |
| ERBB4 | 1117 | −0.836 | 0.098755 | −8.46957 | 2.46E−17 | 6.45E−15 |
| PPFIBP2 | 906.78 | −0.835 | 0.098643 | −8.46633 | 2.53E−17 | 6.51E−15 |
| GJA4 | 57.365 | −0.828 | 0.172651 | −4.79658 | 1.61E−06 | 7.19E−05 |
| COL19A1 | 625.23 | −0.827 | 0.100932 | −8.193 | 2.55E−16 | 5.75E−14 |

TABLE 5 pI:C top downregulated GO terms (to FDR = 1)

| Category | Term | Count | % | PValue | Genes |
|---|---|---|---|---|---|
| KEGG_PATHWAY | ptr05200:Pathways in cancer | 45 | 0 | 1.73E−06 | DCC, FGFR2, FGFR1, ADCY1, FGFR3, WNT5B, ADCY7, XIAP, MITF, FOXO1, NFKBIA, CDH1, KIT, CXCL12, TGFB1, TPM3, ITGAV, PLCB2, PIK3R1, FN1, BMP4, FZD8, COL4A2, BCR, COL4A1, EPAS1, VHL, SMAD3, ITGA3, HGF, APPL1, ARHGEF12, COL4A6, COL4A5, HSP90B1, LAMA3, PLCG1, LAMC3, NTRK1, PLCG2, VEGFA, PTCH1, MAPK8, LAMC1, F2R |
| KEGG_PATHWAY | ptr04015:Rap1 signaling pathway | 28 | 0 | 2.29E−05 | FGFR2, FGFR1, ADCY1, FGFR4, FGFR3, ADCY7, TLN2, EFNA1, CDH1, KIT, SRC, CNR1, TEK, RAPGEF6, RAPGEF5, RAPGEF2, THBS1, ANGPT2, PLCB2, PIK3R1, PARD6B, MAGI3, SIPA1L2, HGF, KDR, PLCG1, VEGFA, F2R |
| KEGG_PATHWAY | ptr04350:TGF-beta signaling pathway | 16 | 0 | 3.04E−05 | BMP4, SMAD9, SMAD7, SMAD6, NODAL, BMPR2, SMAD3, TGFB1, ACVR1B, ID2, THBS1, BMP7, BAMBI, PITX2, BMPR1A, BMP6 |
| KEGG_PATHWAY | ptr04550:Signaling pathways regulating pluripotency of stem cells | 21 | 0 | 3.75E−05 | BMP4, FGFR2, FZD8, FGFR1, FGFR4, FGFR3, SMAD9, WNT5B, TBX3, NODAL, BMPR2, LIFR, SMAD3, ACVR1B, PCGF5, ID2, HAND1, SKIL, PIK3R1, KAT6A, BMPR1A |
| KEGG_PATHWAY | ptr04512:ECM-receptor interaction | 16 | 0 | 6.13E−05 | COL4A2, COL4A1, DAG1, ITGA3, SDC4, COL5A2, COL4A6, COL4A5, ITGA9, LAMA3, LAMC3, ITGAV, COL6A3, LAMC1, THBS1, FN1 |
| KEGG_PATHWAY | ptr04974:Protein digestion and absorption | 15 | 0 | 1.39E−04 | COL18A1, COL4A2, ATP1B1, COL4A1, SLC3A2, MME, ATP1A1, COL5A2, COL4A6, SLC7A7, COL4A5, COL9A2, KCNK5, COL6A3, DPP4 |

TABLE 5-continued pI:C top downregulated GO terms (to FDR = 1)

| Category | Term | Count | % | PValue | Genes |
|---|---|---|---|---|---|
| KEGG_PATHWAY | ptr05205:Proteoglycans in cancer | 24 | 0 | 4.32E−04 | FZD8, FGFR1, WNT5B, ERBB4, ERBB3, LUM, HGF, SDC4, CD63, ARHGEF12, ITPR3, SRC, TGFB1, KDR, EZR, PLCG1, ITGAV, PLCG2, VEGFA, CAMK2D, PTCH1, THBS1, PIK3R1, FN1 |
| KEGG_PATHWAY | ptr04750:Inflammatory mediator regulation of TRP channels | 15 | 0 | 0.00105 | ADCY1, ADCY7, TRPV2, TRPA1, F2RL1, ITPR3, PRKCE, SRC, PLCG1, NTRK1, PLCG2, CAMK2D, MAPK8, PLCB2, PIK3R1 |

TABLE 6 pI:C top upregulated GO terms (to FDR = 1)

| Category | Term | Count | % | PValue | Genes |
|---|---|---|---|---|---|
| KEGG_PATHWAY | hsa05322:Systemic lupus erythematosus | 36 | 0.047978 | 4.45E−22 | HIST1H2AC, HIST1H4L, HIST1H4K, HIST1H2AG, HIST1H2AE, SNRPD1, HIST1H2BO, HIST2H2AB, HIST1H2BN, HIST1H2BK, HIST1H4B, HIST2H2AC, HIST1H2BI, HIST1H2BJ, H2AFZ, HIST1H4E, HIST1H4F, HIST1H4C, HIST1H4D, HLA-DOA, HIST1H4J, HIST1H4H, HIST1H2BC, HIST1H2BD, HIST1H2BH, ACTN3, HLA-DQA2, HIST2H2BE, HIST1H3B, HIST1H2AH, HIST1H2AJ, HIST1H3F, HIST1H2AM, HIST1H3G, HIST1H3H, HIST1H3I |
| KEGG_PATHWAY | hsa05034:Alcoholism | 35 | 0.046645 | 5.78E−17 | HIST1H2AC, HIST1H4L, HIST1H4K, HIST1H2AG, ADCY5, HIST1H2AE, HAT1, HIST1H2BO, HIST2H2AB, HIST1H2BN, HIST1H2BK, HIST1H4B, HIST2H2AC, HIST1H2BI, HIST1H2BJ, H2AFZ, HIST1H4E, HIST1H4F, HIST1H4C, HIST1H4D, HIST1H4J, HIST1H4H, HIST1H2BC, HIST1H2BD, HIST1H2BH, NPY, HIST2H2BE, HIST1H3B, HIST1H2AH, HIST1H2AJ, HIST1H3F, HIST1H2AM, HIST1H3G, HIST1H3H, HIST1H3I |
| KEGG_PATHWAY | hsa03030:DNA replication | 18 | 0.023989 | 3.31E−16 | POLA1, MCM2, RNASEH2A, MCM3, MCM4, MCM5, RPA3, MCM6, POLD3, PRIM1, RPA2, RFC3, RFC4, MCM7, RFC2, PRIM2, PCNA, FEN1 |

TABLE 6-continued pI:C top upregulated GO terms (to FDR = 1)

| Category | Term | Count | % | PValue | Genes |
|---|---|---|---|---|---|
| KEGG_PATHWAY | hsa05203:Viral carcinogenesis | 24 | 0.031985 | 4.37E−07 | HIST1H4L, HIST1H2BC, HIST1H2BD, HIST1H4K, PIK3CB, HIST1H2BH, CHEK1, ACTN3, CDK2, HIST1H2BO, CCNE2, HIST1H2BN, HIST1H2BK, HIST2H2BE, HIST1H4B, JUN, HIST1H2BI, HIST1H2BJ, HIST1H4E, HIST1H4F, HIST1H4C, HIST1H4D, HIST1H4J, HIST1H4H |
| KEGG_PATHWAY | hsa03430:Mismatch repair | 8 | 0.010662 | 7.83E−06 | EXO1, POLD3, RPA2, RFC3, RFC4, RFC2, PCNA, RPA3 |
| KEGG_PATHWAY | hsa03460:Fanconi anemia pathway | 10 | 0.013327 | 6.69E−05 | RPA2, POLI, BLM, FANCD2, FANCI, BRIP1, RMI2, BRCA1, RAD51, RPA3 |
| KEGG_PATHWAY | hsa04110:Cell cycle | 15 | 0.019991 | 8.02E−05 | E2F1, CDC6, E2F2, CHEK1, MCM2, MCM3, MCM4, CDK2, MCM5, CDC25B, MCM6, CCNE2, MCM7, PCNA, ORC1 |
| KEGG_PATHWAY | hsa05218:Melanoma | 10 | 0.013327 | 6.57E−04 | E2F1, E2F2, FGF8, PDGFA, PIK3CB, MET, PDGFRA, PDGFRB, FGF10, PDGFD |

Although the invention has been described in connection with specific embodiments, it is understood that the invention is not limited to such specific embodiments but encompasses all such modifications and variations apparent to a skilled artisan that fall within the scope of the appended claims.

We claim:

1. A method for producing a population of cardiac progenitors from human pluripotent stem cells, comprising the steps of:

(i) culturing human pluripotent stem cells in the presence of a small molecule activator of Wnt/β-catenin signaling for 24 hours;

(ii) culturing the cells obtained in step i) in the absence of a small molecule activator of Wnt/β-catenin signaling for 48 hours; and (iii) culturing the cells obtained in step (ii) in the presence of a small molecule inhibitor of Wnt/β-catenin signaling and polyinosinic-polycytidylic acid (pI:C) for 48 hours such that cardiac progenitors that express increased JAG1 compared to cells obtained in step (ii) that are cultured for 48 hours in the presence of a small molecule inhibitor of Wnt/β-catenin signaling and without pI:C are obtained.

2. An in vitro method for generating a population of developmentally mature cardiomyocytes from human pluripotent stem cells, comprising the steps of:
   (i) culturing human pluripotent stem cells for 24 hours in the presence of a small molecule activator of Wnt/β-catenin signaling;
   (ii) removing the small molecule activator of Wnt/β-catenin signaling from the culture at the end of step (i) and maintaining the resulting culture for 48 hours in the absence of a small molecule activator of Wnt/β-catenin signaling;
   (iii) culturing the cells obtained in step (ii) in the presence of a small molecule inhibitor of Wnt/β-catenin signaling and polyinosinic-polycytidylic acid (pI:C) for 48 hours such that a cell population comprising cardiac progenitors that express increased JAG1 compared to cells obtained in step (ii) that are cultured for 48 hours with a small molecule inhibitor of Wnt/β-catenin signaling and without pI:C are obtained; and
   (iv) culturing the cell population obtained in step (iii) for about 9 to about 140 days until developmentally mature cardiomyocytes are obtained.

3. The method of claim 2, wherein the developmentally mature cardiomyocytes are characterized by one or more of:
   (i) an increased ratio of adult myofilament isoforms to fetal myofilament isoforms;
   (ii) increased expression of Jagged-1 (Jag1);
   (iii) increased expression of branched chain amino acid dehydrogenase (DBT), ATP synthase subunit (ATP5F1), or cytoplasmic mitochondrial DNA-stabilizing ATP transporter SLC25A4;
   (iv) increased expression of cardiac troponin I (cTnI), alpha-myosin heavy chain (αMHC), and myosin light chain 2v (MLC2v); and
   (v) longer sarcomeres;
as compared to cells obtained in step (ii) that are cultured with a small molecule inhibitor of Wnt/β-catenin signaling and without pI:C.

4. The method of claim 3, wherein the adult myofilament isoforms comprise cTnT6+cTnT11 isoforms and the fetal myofilament isoforms comprise cTnT1+cTnT10 isoforms.

5. The method of claim 2, wherein the small molecule activator of Wnt/β-catenin signaling is a small molecule Gsk3 inhibitor.

6. The method of claim 5, wherein the small molecule Gsk3 inhibitor is selected from CHIR 99021, CHIR 98014, BIO-acetoxime, BIO, LiCl, SB 216763, SB 415286, AR A014418, 1-Azakenpaullone, and Bis-7-indolylmaleimide, or a combination thereof.

7. The method of claim 2, wherein the cells obtained in step (iii) have increased expression of Jag-1, Notch2, Atoh1, and Hey1 and reduced expression of fibronectin, vimentin, tbx3, and nodal relative to cardiac progenitors produced by the same method without culturing in the presence of pI:C.

8. A method of making a conductive human microtissue in vitro, the method comprising
   (i) culturing human pluripotent stem cells in the presence of a small molecule activator of Wnt/β-catenin signaling for 24 hours;
   (ii) culturing the cells obtained in step (i) in the absence of a small molecule activator of Wnt/β-catenin signaling for 48 hours;
   (iii) culturing the cells obtained in step (ii) in the presence of a small molecule inhibitor of Wnt/β-catenin signaling and polyinosinic-polycytidylic acid (pI:C) for 48 hours until cells comprising cardiac progenitors that express increased JAG1 compared to cells obtained in step (ii) that are cultured for 48 hours with a small molecule inhibitor of Wnt/β-catenin signaling and without pI:C are obtained; and
   (iv) dissociating the cells obtained in step (iii) and replating the dissociated cells on a substrate whereby the replated cells self-organize into a conductive human microtissue comprising sheets of developmentally mature cardiomyocytes and HCN4$^+$ ventricular conduction system-like cells.

9. The method of claim 8, wherein the substrate is a coated tissue culture plate.

10. The method of claim 8, further comprising isolating HCN4$^+$ ventricular conduction system-like cells from the conductive microtissue.

* * * * *